(12) United States Patent
Cook et al.

(10) Patent No.: US 6,610,663 B2
(45) Date of Patent: Aug. 26, 2003

(54) COMPOSITIONS AND METHODS FOR MODULATING RNA

(75) Inventors: Phillip Dan Cook, Carlsbad, CA (US); Thomas Bruice, Carlsbad, CA (US); Charles John Guinosso, Vista, CA (US); Andrew Mamoru Kawasaki, Oceanside, CA (US); Richard Griffey, San Marcos, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 261 days.

(21) Appl. No.: 09/974,326

(22) Filed: Oct. 10, 2001

(65) Prior Publication Data

US 2002/0160972 A1 Oct. 31, 2002

Related U.S. Application Data

(60) Division of application No. 08/295,744, filed as application No. PCT/US93/02057 on Mar. 5, 1993, now Pat. No. 6,358,931, which is a continuation-in-part of application No. 07/942,961, filed on Sep. 10, 1992, now Pat. No. 5,514,786, which is a continuation-in-part of application No. 07/846,556, filed on Mar. 5, 1992, now Pat. No. 5,359,051, which is a continuation-in-part of application No. PCT/US91/00243, filed on Jan. 11, 1991, which is a continuation-in-part of application No. 07/566,977, filed on Aug. 13, 1990, now abandoned, and a continuation-in-part of application No. 07/463,358, filed on Jan. 11, 1990, now abandoned.

(51) Int. Cl.$^7$ .......................... A61K 48/00; C07H 21/04; C12Q 1/68

(52) U.S. Cl. .......................... 514/44; 536/23.1; 536/24.5; 536/221; 435/6

(58) Field of Search .............................. 536/23.1, 24.5, 536/221; 514/44; 435/6

(56) References Cited

U.S. PATENT DOCUMENTS

| | | | |
|---|---|---|---|
| 4,814,438 A | 3/1989 | Armour et al. | 536/23 |
| 4,816,569 A | 3/1989 | Miyoshi | 536/29 |
| 4,868,103 A | 9/1989 | Stavrianopoulos | 435/5 |
| 5,138,045 A | 8/1992 | Cook et al. | 536/27 |
| 5,212,295 A | 5/1993 | Cook et al | 536/26.7 |
| 5,223,618 A | 6/1993 | Cook et al. | 544/276 |
| 5,359,044 A | 10/1994 | Cook et al. | 536/23.1 |
| 5,359,051 A | 10/1994 | Cook et al. | 536/26.7 |
| 5,378,825 A | 1/1995 | Cook et al. | 536/25.34 |
| 5,514,786 A | 5/1996 | Cook et al. | 536/23.1 |
| 5,658,731 A | 8/1997 | Sproat et al. | 435/6 |

FOREIGN PATENT DOCUMENTS

| | | |
|---|---|---|
| EP | 0042348 A1 | 12/1981 |
| EP | 214908 | 3/1987 |
| EP | 0260032 | 8/1987 |
| WO | WO 91/15499 | 10/1991 |

OTHER PUBLICATIONS

Akabori, V. S. et al., "Syntheses von imidazolderivaten aus x–aminosauren III syntheses von zwei hoheren homologen des histamins," *Eingegang am 4*, 1935, 11(3), 208–213.

Anisuzzaman, A.K.M. et al., "Synthesis of a Carboranyl Nucleoside for Potential Use in Neutron Capture Therapy of Cancer," *Polyhedron*, 1990, 9, 891–892.

Auchter, G. et al., "Stereochemie de Homopropargylumlagerung: Solvolyse von 1,2–Dimethy1–3–pentinytriflat," *Tetrahedron Letters*, 1983, 24(6), 577–580.

Auerbach J. et al., "Synthesis of Terrein, a Metabolite of *Aspergillus terreus*," *J.C.S. Chem. Comm.*, 1974, 298–299.

Bashkin, J. K. et al., "Synthesis and Characterization of Nucleoside Peptides: Toward Chemical Ribonucleases. 1," *J. Org. Chem.*, 1990, 55, 5125–5132.

Beaucage, S. L. et al., "Advances in the Synthesis of Oligonucleotides by the Phosphoramidite Approach," *Tetrahedron*, 1992, 48, 2223–2311.

Beaucage, S. L. et al., "Deoxynucleoside Phosphoramidites—A New Class of Key Intermeidates for Deoxypolynucleotide Synthesis" *Tetrahedron Letters*, 1981, 22, 1859–1862.

Bergstrom et al., "Organoiron mediated alkylation of phosphite esters: Synthesis of dicarbonyl (n5–cyclopentadienyl)iron–derived nucleoside phosphonate esters", *J. Org. Chem.*, 1992, 57, 873–876.

Breslow, R. et al., "Ribonuclease Mimics" *Tetrahedron Letters*, 1991, 47(14/15), 2365–2376.

Burch, R. M. et al., "Oligonucleotides Antisense to the Interleukin 1 Receptor mRNA Block the Effects of Interleukin 1 in Cultured Murine and Human Fibroblasts and in Mice," *J. Clin. Invest.*, 1991, 88, 1190–1196.

Caruthers, M. H., "Synthesis of Oligonucleotides and Oligonucleotide Analogues," *Oligonucleotides: Antisense Inhibitors of Gene Expression*, 1989, Chapter 1, Cohen, J.S. (Ed.), CRC Press, Boca Raton, FL, 7–24.

Cazenave, C. et al., "Enzymatic amplification of translation inhibition of rabbit β–globin mRNA mediated by antimessenger oligodexynucleotides covalently linked to intercalating agents," *Nucl. Acids Res.*, 1987, 15, 4717–4736.

Cimino, G. D. et al., "Psoralens as Photoactive Probes of Nucleic Acid Structure and Function: Organic Chemistry, Photochemistry, and Biochemistry," *Ann.Rev.Biochem.*, 1985, 54, 1151–1193.

(List continued on next page.)

*Primary Examiner*—Jeffrey Fredman
(74) *Attorney, Agent, or Firm*—Woodcock Washburn LLP

(57) ABSTRACT

Compositions and methods for modulating the activity of RNA are disclosed. In accordance with preferred embodiments, antisense compositions are prepared comprising targeting and reactive portions. The reactive portions preferably comprise one or two imidazole functionalities conjugated to the targeting oligonucleotide via linkers with or without intervening intercalating moieties. Therapeutics, diagnostics and research methods also are disclosed, as are synthetic nucleosides and nucleoside fragments that can be elaborated into oligonucleotides.

6 Claims, 23 Drawing Sheets

OTHER PUBLICATIONS

Constant, J. F. et al., "Heterodimeric Molecules Including Nucleic Acids Bases and 9–Aminoacridine. Spectroscopic Studies, Conformations, and Interactions with DNA," *Biochem.,* 1988, 27, 3997–4003.

Cooper, C. et al., "Sites of single–strand breaks in DNA treated with a diol–epoxide of benz[a]anthracene," *Carcinogenesis,* 1983, 4(12), 1645–1649 (Abstract only).

Cowart, M. et al., "A Novel Combined Chemical—Enzymatic Synthesis of Cross–Linked DNA Using a Nucleoside Triphosphate Analogue," *Biochem.,* 1991, 30, 788–796.

Demuynck, M. et al., "(±)–Hysterin: Revised Structure and Total Synthesis," *J. Org. Chem.,* 1979, 44(26), 4863–4866.

Denny, W. A. "DNA–Intercalating Ligands as Anti–Cancer Drugs: Prospects for Future Design," *Anticancer Drug Design,* 1989, 4, 241–263.

Dreyer, G. B. et al., "Seqeunce–specific cleavage of single–stranded DNA: Oligodeoxynucleotide–EDTAFe(II)," *Proc. Natl. Acad. Sci.,* 1985, 82, 968–972.

Gopalakrishnan et al., "Spectroscopic and enzymatic characterization of 2'–5' and 3'–5' RNA hexamers AACCCU synthesized by phosphotriester approach in solution using 2'–t–butyldimethylsilyl protection", *Tetrahedron,* 1991, 47(6), 1075–1090.

Griec, P. A. et al., "Sesquiterpene Lactones: Total Synthesis of (±)–Vernolepin and (±)–Vernomenin[1,2]," *J. of Amer. Chem. Soc.,* Aug. 17, 1977, 99(17), 5773–5780.

Guilard, R. et al., "Synthesis and Characterization of Novel Cobalt Aluminum Cofacial Porphyrins. First Crystal and Molecular Structure of a Heterobimetallic Biphenylene Pillard Cofacial Diporphyrin," *J. of Amer. Chem. Soc.,* 1992, 114, 9877–9889.

Guo, X. et al., "β–Deuterium kinetic isotope effects in the purine nucleoside phosphorylase reaction," *Biochem. J.,* 1991, 278, 487–491.

Hagiwara, Hisahiro, et al., "A Total Synthesis of (+)–Perrottetianal Am" *J. Chem. Soc. Chem. Comm.,* 1987, 1351–1353.

Halmos, T. et al., "Studies of the Selective Silylation of Methyl α–And β–D–Aldohexopyranosides: Stability of the Partially Protected Derivatives in Polar Solvents", *Carbohydrate Research,* 1987, 170, 57–69.

Hashimoto, S. et al., "DNA Strand Scissions by Hydoxamic Acids–Cooper(II) Ion under Aerobic Conditions," *Chemistry Letters,* 1992, 1639–1642.

Helene, C. et al., "Oligodeoxynucleotides covalently linked to intercalating agents: a new family of gene regulatory substances," *Biochemical Society Transactions,* 1986, 14, 201–202.

Helene C. et al., "Control of Gene Expression by Oligodeoxynucleotides Covalently Linked to Intercalating Agents and Nucleic Acid–cleaving Reagent," *Oligonucleotides. Antisense Inhibitors of Gene Expression,* 1989, 137–162.

Helene, C. et al., "Sequence–specific artificial endonucleases," *TIBTECH,* Nov. 1989, 7, 310–315.

Helene, C. et al., "Control of gene expression by oligonucleotides covalently linked to intercalating agents," *Genome,* 1989, 31, 413–421.

Higgins, K. A. et al., "Antisense inhibition of p65 subunit of NF–KB blocks tumorigenicity and causes tumor regression," *Proc. Natl. Acad. Sci. USA,* 1993, 90, 9901–9905.

Hünig, S. et al., "Einfluβ der Umpolungsgruppe auf die Diastereoselektivität der nucleophilen Acylierung α–chiraler Carbonylverbindugen," *Chem. Ber.,* 1989, 122, 1329–1339.

Inouye, M. et al., "Antisense RNA: its functions and applications in gene regulation–a review," *Gene,* 1988, 72, 25–34.

Iribarren, A. M. et al., "2'–O–Alkyl oligoribonucleotides as antisense probes" *Proc. Natl. Acad. Sci.* 1990, 87, 7747–7751.

Iyer, R. P. et al., "3H–1,2–Benzodithiole–3–one 1,1–Dioxide as an Improved Sulfurizing Reagent in the Solid–Phase Synthesis of Oligodeoxyribonucleoside Phosphorothioates," *J. Am. Chem. Soc.,* 1990, 112, 1253–1254.

Jung, M. E. et al., "Facile Synthesis of a Substituted Bicyclo [4.2.1]Nonane via an Anionic [1,3]–Sigmatropic Shift: Use of Long Range 2D Hector and Difference Noe in Structure Determination," *Tetrahedron Letters,* 1989, 30(6), 641–644.

Kitajima, I. et al., "Ablation of Transplanted HTLV–I Tax-Transformed Tumors in Mice Antisense Inhibition of NF–κB," *Science,* 1992, 258, 1792–1795.

Knorre, D. G. et al., "Complemetary–Addressed (Sequence–Specific) Modification of Nucleic Acids," 1985, 32, 291–321.

Knorre, D. G. et al., "Oligonucleotides Linked to Reactive Groups," Chapter 8 in *Oligodeoxynucleotides. Antisense Inhibitors of Gene Expression,* J.S. Cohen ed., CRC Press, Boca Raton, FL, pp. 171–196, 1989.

Kochetkov N. K. et al., *Organic Chemistry of Nucleic Acids, Part B.,* Plenun Press, New York, pp. 487–490, 1972.

Kohn, K. W. et al., "Mechanisms of DNA sequence selective alkylation of guanine–N7 positions by nitrogen mustards," *Nucleic Acids Research,* 1987, 15(24), 10531–10549.

Kunitake, T. et al., "Multifunctional Hydrolytic Catalyses. 8. Remarkable Acceleration of the Hydrolysis of p–Nitropheny Acetate by Micellar Bifunctional Catalysts[1]," *J. of the Amer. Chem. Soc.,* Nov. 24, 1976, 98(24) 7799–7806.

Le Doan, T. et al., "Sequence–targeted chemical modification of nucleic acids by complementary oligonucleotides covalently linked to porphyrins," *Nucl. Acids Res.,* 1987, 15, 8643–8659.

Lipshutz, B. H. et al., "Progress Toward Roflamycoin; Synthesis of the C–12 to C–35 Section in Homochiral Form," *Tetrahedron Letters,* 1989, 30(1), 15–18.

Loose–Mitchell, D. S., "Antisense nucleic acids as a potential class of pharmaceutical agents," *TiPS,* 1996, 9, 45–47.

Luo, et al., "Palladium–catalyzed cyclization and cross–coupling of acetylenic aryl triflates with organotin reagents," *Tetrahedron Letters,* 1991, 32(52), 7703–7706 (Abstract only).

March, J., *Advanced Organic Chemistry,* 4th Edition, Wiley Interscience, New York, 1992, p. 378.

Marcus–Sekura, C. J., "Techniques for Using Antisense Oligodeosyribonucleotides to Study Gene Expression," *Analyt. Biochem.,* 1988, 172, 289–295.

Marshall, J. A. et al., "Heterolytic Fragmentation of 1,3–Dithianyl Tosylates," *Tetrahedron Letters,* 1971, (13), 871–878.

Meyer, R.B. et al., "Efficient, Specific Cross–Linking and Cleavage of DNA by Stable, Synthetic Complementary Oligodeoxynucleotides," *J. Am. Chem. Soc.,* 1989, 111, 8517–8519.

Meyers, A. I. et al., "Synthesis via 2–Oxazolines. II. A Versatile Synthesis of Aliphatic Carboxylic Acids and Esters. Mono–and Dialkylation of Acids Masked by a Simple Protecting Group," *J. of Am. Chem. Soc.,* Nov. 4, 1970, 92(22), 6644–6646.

Mitchell, M.J. et al., "Boron trifluoride–methanol complex as a non–depurinating detritylating agent in DNA Synthesis," *Nucl. Acids Res.,* 1990, 18, 5321.

Mitsunobu, O., "The Use of Diethyl Azodicarboxylate and Triphenylphosphine in Synthesis and Transformation of Natural Products," *Synthesis,* 1981, 1–28.

Nair, V. et al., "Isodideoxynucleosides: A Conceptually New Class of Nucleoside Antiviral Agents," *J. Am. Chem. Soc.,* 1992, 114, 7951–7953.

Ortiz, C. et al., "The Total Synthesis of ±–Isoretronecanol from Pyrrole+," *Tetrahedron Letters,* 1985, 2831–2832.

Rosowsky, A. et al., "Synthesis of 3'–O–Propargylthymidine As a Candidate Antiretroviral Agent," *Nucleosides & Nucleotides,* 1989, 8(4), 491–497.

Rothenberg, M. et al., "Oligdeoxynucleotides as Anti–Sense Inhibitors of Gene Expression: Therapeutic Implications," *J. Natl. Cancer Inst.,* 1989, 81, 1539–1544.*

Seebach, D., "Methods of Reactivity Umpolung," *Angew. Chem. Int. Ed. Engl.,* 1979, 18, 239–258.*

Sigman, D. S. et al., "Nuclease Activity of 1,10–Phenanthroline–Copper Ion," *Acc. Chem. Res.,* 1986, 19, 180–186.*

Simons, M. et al., "Antisense c–myb oligonucleotides inhibit intimal arterial smooth muscle cell accumulation in vivo," *Nature,* 1992, 359, 67–70.*

Soloway, A. H. et al., "The development of carboranyl nucleic acid precursors for use in neutron capture therapy of turmors," *Pure & Appl. Chem.,* 1991, 63(3), 411–413.*

Spalholz, B. A. et al., "Bovine Papillomavirus Transcriptional Regulation: Localization of the E2–Responsive Elements of the Long Control Region," *J. Virology,* 1987, 61, 2128–2137.*

Sproat, B. S. et al., "New synthetic routes to synthons suitable for 2–O–allyloligoribonucleotide assembly," *Nucl. Acids Res.,* 1991, 19, 733–738.*

Stein, C. A. et al., "Antisense Oligonucleotides as Therapeutic Agents—Is the Bullet Really Magical?," *Science,* 1993, 261, 1004–1012.*

Stein, C. A. et al., "Oligodeoxynucleotides as Inhibitors of Gene Expression: A Review," *Cancer Res.,* 1988, 48, 2659–2668.*

Stork, G. et al., "Chiral Synthesis of Prostaglandins ($PGE_1$) from D–Glyceraldehyde," *J. Amer. Chem. Soci.,* 1977, 99(4), 1275–1276.*

Takano, S. et al., "A New Route to the Olivacine Type Alkaloid Ring System via The Fischer Base Intermediate," *Tetrahedron Letters,* ©1979, 4, 369–372.*

Thuong, N. T. et al., "Oligodeoxynucleotides Covalently Linked to Intercalating and Reactive Substances: Synthesis, Characterization and Physicochemical Studies," Ch. in 2 in *Oligodeoxynucleotides. Antisense Inhibitors of Gene Expression,* J.S. Cohen, ed., CRC Press, Boca Raton, FL, pp. 24–51, 1989.*

Toulme, J. J. et al., "Specific inhibition on mRNA translation by complementary oligonucleotides covalently linked to intercalating agents," *Proc. Natl. Acad. Sci. USA,* 1986, 83, 1227–1231.

Tramontano, A. et al., "Chemical reactivity at an antibody binding site elicited by mechanistic design of a synthetic antigen," *Proc. Natl. Acad. Sci. USA,* 1986, 83, 6736–6740.

van der Krol, A. R. et al., "Antisense genes in plant: an overview (Natural plant anti–mRNA; gene inactivation; artificial antisense gene; electroporation)," *Gene,* 1988, 72, 45–50.

van der Krol, A. R. et al., "Modulation of Eukaryotic Gene Expression by Complementary RNA or DNA Sequences," *BioTechniques,* 1988, 6, 958–979.

Vasseur, J. J. et al., "Oligonucleosides: Synthesis of a Novel Methylhydroxylamine–linked Nucleoside Dimer and Its Incorporation into Antisense Sequences," *J. Am. Chem. Soc.,* 1992, 114, 4006–4007.

Vlassov, V. V. et al., "Complementary addressed modification and cleavage of a single stranded DNA fragment with alkylating oligonucleotide derivatives," *Nucl. Acids Res.,* 1986, 14(10), 4065–4076.

Vlassov, V. V. "Inhibition of Tick–Borne Viral Encephalitis expression using Covalently Linked Oligonucleotide Analogs," *Natl. Cancer Inst.,* Jun. 18–21, 1989, *Oligodeoxynucleotides as Antisense Inhibitors of Gene Expression: Therapeutic Implications.*

Walder, "Antisense DNA and RNA: progress and prospects," *Genes & Dev.,* 1988, 2, 502–504.

Wehrmeister, H. L., "Periodate Oxidations of Oxazolines," *J. Org. Chem.,* 1967, 26, 3821–3824.

Whitesides, G. M. et al., "Cooper(I) Alkoxides. Synthesis, Reactions, and Thermal Decomposition[1]," *J. Amer. Chem. Soci.,* 1974, 96(9), 2829–2835.

Yeung, A. T. et al., "Photoreactivities and Thermal Properties of Psoralen Cross–Links," *Biochemistry,* 1988, 27, 3204–3210.

Zon, G., "Oligonucleotide Analogues as Potential Chemotherapeutic Agents," *Pharm. Res.,* 1988, 5, 539–547.

Zon, G., "Synthesis of Backbone–Modified DNA analogues for Biological Applications," *J. Protein Chem.,* 1987, 6, 131–145.

Zuckermann, R. N. et al., "A Hybrid Sequence–Selective Ribonuclease S," *J.Am.Chem.Soc.,* 1988, 110, 6592–6594.

* cited by examiner

18 cis,cis
19 trans, trans

COMPOSITIONS AND METHODS FOR MODULATING RNA

RELATED APPLICATIONS

This application is a divisional of application Ser. No. 08/295,744 filed Aug. 30, 1994, now U.S. Pat. No. 6,358, 931, which is a 371 of PCT/US93/02057, filed Mar. 5, 1933, which is a continuation-in-part of application Ser. No. 07/942,961 filed Sep. 10, 1992 now U.S. Pat. No. 5,514,786, which is a continuation-in-part of application Ser. No. 07/846,556, filed Mar. 5, 1992, now U.S. Pat. No. 5,359,051, which is a continuation-in-part of application Ser. No. PCT/US91/00243, filed Jan. 11, 1991, which is a continuation-in-part of application Ser. No. 07/463,358, filed Jan. 11, 1990 now abandoned and application Ser. No. 07/566,977, filed Aug. 13, 1990 now abandoned. These applications are assigned to the assignee of this invention. The entire disclosure of each is incorporated herein by reference.

FIELD OF THE INVENTION

This invention relates to materials and methods for detecting and modulating the activity of RNA. The invention generally relates to the field of "antisense" compounds which are capable of specific hybridization with a nucleotide sequence of an RNA. In accordance with preferred embodiments, this invention is directed to the design, synthesis, and application of oligonucleotides and to methods for achieving therapeutic treatment of disease, regulating gene expression in experimental systems, assaying for RNA and for RNA products through the employment of antisense interactions with such RNA, diagnosing diseases, modulating the production of proteins, and cleaving RNA in a site specific fashion.

BACKGROUND OF THE INVENTION

It is well known that most of the bodily states in mammals, including most disease states, are effected by proteins. Such proteins, either acting directly or through their enzymatic or other functions, contribute in major proportion to many diseases in animals and man. Classical therapeutics has generally focused upon interactions with such proteins in efforts to moderate their disease-causing or disease-potentiating functions. Recently, however, attempts have been made to modulate the actual production of such proteins by interactions with the intracellular RNA molecules that code for their synthesis. By interfering with the production of proteins, it has been hoped to effect therapeutic results with maximum effect and minimal side effects. It is the general object of such therapeutic approaches to interfere with or otherwise modulate gene expression which would lead to undesired protein formation.

One method for inhibiting specific gene expression is the use of oligonucleotides as "antisense" agents. The oligonucleotides complementary to a specific target messenger RNA (mRNA) sequence are used. A number of workers have reported such attempts. Pertinent reviews include Stein, et al., *Cancer Research* 1988, 48, 2659; Walder, *Genes & Development* 1988, 2, 502; Marcus-Sekura, *Anal. Biochemistry* 1988, 172, 289; Zon, *Journal of Protein Chemistry* 1987, 6, 131; Zon, *Pharmaceutical Research* 1988, 5, 539; Van der Krol, et al., *BioTechniques* 1988, 6, 958; and Loose-Mitchell, *TIPS* 1988, 9, 45. Each of the foregoing provide background concerning general antisense theory and prior techniques.

Thus, antisense methodology has been directed to the complementary hybridization of relatively short oligonucleotides to single-stranded mRNA or single-stranded DNA such that the normal, essential functions of these intracellular nucleic acids are disrupted. Hybridization is the sequence specific hydrogen bonding of oligonucleotides via Watson-Crick base pairs to RNA or single-stranded DNA. The bases of such base pairs are said to be complementary to one another.

Prior attempts at antisense therapy have provided oligonucleotides which are designed to bind in a specific fashion to—i.e., which are specifically hybridizable with—a specific mRNA by hybridization. Such analogs are intended to inhibit the activity of the selected mRNA—e.g., to interfere with translation reactions by which proteins coded by the mRNA are produced—by any of a number of mechanisms. It has been hoped to provide therapeutic benefits by inhibiting the formation of the specific proteins which are coded for by the mRNA sequences.

A number of chemical modifications have been introduced into antisense oligonucleotides to increase their therapeutic activity. Such modifications are designed to increase cell penetration of the antisense oligonucleotides, to stabilize them from nucleases and other enzymes that degrade or interfere with the structure or activity of the oligonucleotides in the body, to enhance their binding to targeted RNA, to provide a mode of disruption (terminating event) once sequence-specifically bound to targeted RNA, and to improve their pharmacokinetic properties. At present, however, no generalized antisense oligonucleotide therapeutic or diagnostic scheme has been found. The most serious deficiency of prior efforts has been the complete lack of a termination event once appropriate hybridization takes place or the occurrence of a termination event that is so inefficient that a useful potency cannot be achieved due to the inability of oligonucleotides to be taken into cells at effective concentrations. The activity of the antisense oligonucleotides presently available has not been sufficient for effective therapeutic, research reagent, or diagnostic use in any practical sense. Accordingly, there has been and continues to be a long-felt need for oligonucleotides which are capable of effective therapeutic and diagnostic antisense use.

This long-felt need has not been satisfied by prior work in the field of antisense oligonucleotide therapy and diagnostics. Others have failed to provide materials which are, at once, therapeutically or diagnostically effective at reasonable concentrations.

Initially, only two mechanisms or terminating events have been thought to operate in the antisense approach to therapeutics. These are the "hybridization arrest" mechanism (i.e., arrest of translation via antisense hybridization) and the cleavage of hybridized RNA by the cellular enzyme, ribonuclease H (RNase H). It is likely that additional "natural" events may be involved in the disruption of targeted RNA, however. Other terminating events also have been studied in an attempt to increase the potency of oligonucleotides for use in antisense diagnostics and therapeutics. Thus, an area of research has developed in which a second domain of the oligonucleotide, generally referred to as a pendant group, has been introduced.

The pendant group is not involved with the specific Watson-Crick hybridization of the oligonucleotide with the mRNA but is carried along by the oligonucleotide to serve as a reactive functionality. The pendant group is intended to interact with the mRNA in some manner to more effectively inhibit translation of the mRNA into protein. Such pendant groups have also been attached to molecules targeted to either single or double stranded DNA.

The type of pendant group known as an intercalating agent has been disclosed by Cazenave, et al., *Nucleic Acid Research* 1987, 15, 4717 and Constant, et al., *Biochemistry* 1988, 27, 3997. The disclosed purpose of such intercalating agents is to add binding stability to the hybrid formed between the oligonucleotide and the target nucleic acid by binding to the duplex formed between them.

It has also been disclosed to provide a pendant group to oligonucleotides which is capable of cross-linking. Thus, a pendant agent such as psoralen has been disclosed by Yeung, et al., *Biochemistry* 1988, 27, 2304. It is believed that after hybridization of the oligonucleotide to the target mRNA, the psoralen is photoactivated to cross-link with the mRNA forming a covalent bond between the oligonucleotide and the mRNA, thereby permanently inactivating the mRNA molecule and precluding the further formation of protein encoded by that particular portion of RNA.

It has also been proposed to employ a cross-linking alkylating agent as a pendant group for oligonucleotides for use in antisense approaches to diagnostics and therapeutics, as disclosed by Meyer, *J. Am. Chem. Soc.* 1989, 111, 8517 and Knorre and Vlassov, *Progress in Nucleic Acid Research and Molecular Biology* 1985, 32, 291.

The object of employing alkylating agents as pendant groups in oligonucleotides in antisense approaches is to cause the alkylating agent to react irreversibly with the target mRNA. Such irreversible binding between the antisense oligonucleotide and the mRNA is generally covalent and leads to permanent inactivation of the mRNA with a concomitant halt in protein production from the portion of mRNA thus inactivated.

A further strategy which has been proposed is to use chemical reagents which, under selected conditions, can generate a radical species for reaction with the target nucleic acid to cause cleavage or otherwise to inactivate it. Proposed pendant groups of this category include coordination complexes containing a metal ion with associated ligands. A metal ion can change oxidation state to generate reactive oxygen-containing radical ions or other radical species. Doan, et al, *Nucleic Acids Research* 1987, 15, 8643 have disclosed iron/EDTA and iron/porphyrin species for this purpose. Copper/phenanthroline complexes have been disclosed by Sigman, *Accounts of Chemical Research* 1986, 19, 180. Dreyer, et al., *Proceedings of the National Academy of Sciences, U.S.A.* 1985, 82, 968 have investigated the EDTA/Fe moiety to cleave nucleic acids.

Prior approaches using cross-linking agents, alkylating agents, and radical-generating species as pendant groups on oligonucleotides for antisense diagnostics and therapeutics have several significant shortcomings. The sites of attachment of the pendant groups to oligonucleotides play an important, yet imperfectly known, part in the effectiveness of oligonucleotides for therapeutics and diagnostics. Prior workers have described most pendant groups as being attached to a phosphorus atom which, as noted above, affords oligonucleotides with inferior hybridization properties. Prior attempts have been relatively insensitive in that the reactive pendant groups have not been effectively delivered to sites on the messenger RNA molecules for alkylation or cleavage in an effective proportion. Moreover, even if the reactivity of such materials were perfect, i.e. if each reactive functionality were to actually react with a messenger RNA molecule, the effect would be no better than stoichiometric. That is, only one mRNA molecule would be inactivated for each molecule of oligonucleotide. It is also likely that the non-specific interactions of the modified oligonucleotides with molecules other than the target RNA, for example with other molecules that may be alkylated or which may react with radical species, as well as possible self-destruction of the oligonucleotides, not only diminishes the diagnostic or therapeutic effect of the antisense treatment but also leads to undesired toxic reactions in the cell or in vitro. This is especially acute with the radical species which are believed to be able to diffuse beyond the locus of the specific hybridization to cause undesired damage to non-target materials, other cellular molecules, and cellular metabolites. This perceived lack of specificity and stoichiometric limit to the efficacy of such prior alkylating agent and radical generating-types of antisense oligonucleotides is a significant drawback to their employment.

Accordingly, there remains a great need for antisense oligonucleotide formulations which are capable of improved specificity and effectiveness both in binding and in mRNA modulation or inactivation without the imposition of undesirable side effects.

OBJECTS OF THE INVENTION

It is one object of this invention to provide oligonucleotides for use in antisense oligonucleotide diagnostics and therapeutics.

It is a further object of this invention to provide such oligonucleotides which are effective in modulating the activity of an RNA.

A further object of this invention is to provide such oligonucleotides which are less likely to evoke undesired or toxic side reactions.

A further object is to provide research and diagnostic methods and materials for assaying bodily states in animals, especially diseased states.

A further object is to provide means for modifying nucleic acids for effecting substitutions on selective portions thereof.

Yet another object is to provide therapeutic and research methods and materials for the treatment of diseases through modulation of the activity of DNA and RNA.

Still another object is to provide means for the selective cleavage of RNA.

These and other objects will become apparent to persons of ordinary skill in the art from a review of the present specification and appended claims.

SUMMARY OF THE INVENTION

In accordance with the present invention, compositions for modulating the activity of DNA and RNA are provided. The compositions useful for modulating the activity of an RNA or detecting its presence in accordance with this invention generally comprise three portions. The first portion, the targeting portion, is a portion which is specifically hybridizable with a preselected nucleotide sequence of the RNA. The compositions further comprise intercalating portions capable of intercalating between bases or base pairs formed upon hybridization with RNA. The compositions further comprise a reactive portion capable of catalyzing or otherwise effecting the cleavage of RNA, especially of its phosphodiester bonds.

In one embodiment of the invention, preferred compositions according to the present invention comprise at least one ribofuranosyl unit which bears at its 2' position both an intercalating portion and a reactive portion. The compositions may also include a tether or some other means for connecting the targeting and reactive portions together to form the composition. In a further embodiment of the invention, preferred compositions comprise an oligonucleotide or oligonucleoside including a tether extending from an inter-nucleoside linkage of the oligonucleotide or oligonucleoside An intercalating portion and a reactive portion portion are connected to the tether. A further tether may be used to connect the intercalating portion to the reactive portion.

The targeting portion of the compositions of this invention preferably comprises oligonucleotides and oligonucleosides including from about 3 to about 50 base units with 8 to 40 subunits being preferred and 12 to 25 being still more preferred. Oligonucleotides and oligonucleosides having about 15 base units are preferable for the practice of certain embodiments of the present invention.

For therapeutic use, preferably, the targeting portion is an analog of an oligonucleotide wherein at least some of the phosphodiester bonds of the oligonucleotide have been substituted with a structure which functions to enhance nuclease resistance and/or to enhance the ability of the compositions to penetrate into the intracellular region of cells where the RNA whose activity is to be modulated is located. In certain preferred embodiments such substitutions comprise phosphorothioate bonds or short chain alkyl or cycloalkyl structures. In accordance with other preferred embodiments, the phosphodiester bonds are substituted with other structures having hetero atoms therein forming oligonucleosides.

In certain preferred embodiments, the intercalating portions of the compositions are known, non-carcinogenic types of polycyclic aromatic hydrocarbons or heterocyclic moieties capable of intercalating between predetermined bases and base pairs formed by a hybrid antisense/RNA target sequence duplex.

In accordance with other preferred embodiments the reactive portion of the composition comprises a functionality capable of catalyzing the hydrolysis or cleavage of phosphodiester bonds in RNA. Such functionalities may either be basic, acidic, amphoteric, ionic, or hydrophobic. Heteroatomic species can be formulated to be either basic or acidic or, indeed, to be amphoteric for such purposes. In certain preferred embodiments of the invention, the reactive portion includes multiple ligands capable of coordinating certain metals such as divalent metals including magnesium, calcium and zinc.

This invention also comprehends the employment of alkylating and free-radical-forming functionalities as the reactive portions of the subject compositions, particularly where said alkylating or free-radical-forming materials are delivered into the minor groove of the hybrid formed between the compositions of the invention and the RNA to be modulated.

In accordance with other embodiments, the compositions of the invention for modulating the activity of RNA comprise heterocyclic structures having at least one RNA cleaving moiety or some other moiety capable of interacting with an RNA appended thereto. Certain of these compositions are adapted for delivery of the RNA cleaving (i.e., intercalating or minor-groove-binding) moiety to a predetermined portion of the RNA strand, in part by carefully selecting the sites for attachment of the heterocyclic RNA cleaving moieties to the antisense oligonucleotide or analog. Compositions of the invention may include naturally occurring or non-naturally occurring sugar portions, as well as naturally occurring or non-naturally occurring base portions. Accordingly, novel nucleosides and nucleoside analogs are provided. Such nucleosides and nucleoside analogs may be incorporated into oligonucleotides which are useful in the practice of the invention.

The invention also is directed to methods for modulating the activity of an RNA comprising contacting an organism having the RNA with a composition formulated in accordance with the foregoing considerations. It is preferred that the RNA which is to be modulated be preselected to comprise preferably messenger RNA which codes for a protein whose formation is to be modulated. The invention may also be applied to pre-messenger RNA and, indeed, to RNA generically and to single-stranded DNA. The targeting portion of the composition to be employed is selected to be complementary to the preselected portion of RNA or single stranded DNA, that is, to be an antisense oligonucleotide for that portion.

This invention is also directed to methods for treating an organism having a disease characterized by the undesired production or overproduction of a protein, comprising contacting the organism with a composition in accordance with the foregoing considerations, preferably a composition which is designed to specifically bind with messenger RNA which codes for the protein whose production is to be modulated or inhibited.

The invention is also directed to the utilization of groups in addition to the reactive functional groups that are further appended to oligonucleotides. Such pendant groups may lead to enhanced oligonucleotide uptake, enhanced resistance of oligonucleotide to degradation by nucleases, and stronger binding of the oligonucleotides to targeted RNA. Further functionalities may serve to attach reporter groups such as biotin and various fluorophores to sequence-specific oligonucleotides for diagnostic purposes. More than one non-reactive functionality may be attached to each oligonucleotide, two or more non-reactive functionalities may be attached to a single nucleoside unit, and a combination of non-reactive functionalities and reactive functionalities may be attached to a single nucleoside unit or a single oligonucleotide.

Nuclease resistant oligonucleotides of this invention consist of a single strand of nucleic acid bases linked together through linking groups. The target portion of the nuclease resistant oligonucleotide may range in length from about 5 to about 50 nucleic acid bases. However, in accordance with the preferred embodiment of this invention, a target sequence of about 15 bases in length is believed to be optimal.

The bases of the individual nucleotides comprising the oligonucleotides of the invention may be pyrimidines such as thymine, uracil or cytosine, or purines such as guanine or adenine, or both, arranged in a specific sequence. Additionally, they may be any of the synthetic bases known in the art. The sugar moiety of the nucleotides may be of the deoxyribose or ribose type or may be a synthetic sugar known in the art. The phosphate linking groups of the oligonucleotides of the invention may be native or wild type phosphodiester linkages or synthetic linking groups such as, for example, phosphorothioate, phosphorodithioate, methylphosphonate, or alkylphosphonate. Other synthetic linkages that substitute for the phosphate linking groups can also be utilized. For nuclease resistance synthetic linkages are preferred.

The resulting novel oligonucleotides are resistant to nuclease degradation and exhibit hybridization properties of higher quality relative to wild type (DNA-DNA and RNA-DNA) duplexes and the phosphorus modified oligonucleotide antisense duplexes containing phosphorothioates, methylphosphonates, phophoramidates and phosphorotriesters.

The invention further is directed to diagnostic methods for detecting the presence or absence of abnormal RNA molecules or abnormal or inappropriate expression of normal RNA molecules in organisms or cells. It is also directed to methods for the selective cleaving of RNA useful in research and diagnostics. Such selective cleaving is accomplished by interacting RNA with compositions of the invention which have reactive portions capable of effecting such cleavage and targeting portions designed to enforce selectivity.

The invention is also directed to methods for modulating the production of a protein by an organism comprising contacting the organism with a composition formulated in accordance with the foregoing considerations. It is preferred that the RNA or DNA portion which is to be modulated be preselected to comprise that portion of DNA or RNA which codes for the protein whose formation is to be modulated. The targeting portion of the composition to be employed is, thus, selected to be complementary to the preselected portion of DNA or RNA, that is, to be an antisense oligonucleotide for that portion.

This invention is also directed to methods of treating an organism having a disease characterized by the undesired production of a protein. This method comprises contacting the organism with a composition in accordance with the foregoing considerations. The composition is preferably one which is designed to specifically bind with messenger RNA which codes for the protein whose production is to be inhibited.

The invention further is directed to diagnostic methods for detecting the presence or absence of abnormal RNA molecules or abnormal or inappropriate expression of normal RNA molecules in organisms or cells.

The invention is also directed to methods for the selective binding of RNA for research and diagnostic purposes. Such selective, strong binding is accomplished by interacting such RNA or DNA with compositions of the invention which are resistant to degradative nucleases and may hybridize more strongly and with greater fidelity than any other known oligonucleotide.

The invention is also directed to in vitro use of certain compounds of the invention as artificial restriction enzymes. Such artificial restriction enzymes are rendered site specific by selection of the appropriate base sequence of the oligonucleotide or oligonucleoside portion of the compound. When so used as in vitro artificial restriction enzymes, the compounds of the inventions can further include a metal ion coordinated to the remainder of the compound via one or more ligand groups selected for specific coordination of a selected metal. Preferred metals are those forming octahedral or tetrahedral coordination complexes. Other metals that can penta-coordinate might also be selected.

In accordance with a further embodiment of the invention, novel processes are provided for the synthesis of novel nucleoside analogs that are substituted in the 2' position and which are useful for incorporation into oligonucleotides of the invention. Such process provides for introduction of a 2' substituent in the absence of blocking of either the 3' or 5' hydroxyl groups of a ribofuranosyl nucleoside. For adenosine and cytidine, such processes utilize treatment with sodium hydride followed by use of an alkyl halide. For uridine, such processes utilize treatment with stannous chloride and an alkyl halide. For guanosine, such processes treat 2,6-diamino purine riboside with sodium hydride and alkyl halide followed by deamination to the guanosine compound as is disclosed in U.S. patent application Ser. No. 918,362, filed Jul. 23, 1992, the entire disclosure of which is herein incorporated by reference. The reactions are conducted at or near room temperature. These conditions are contrasted to prior known processes that require strong alkylating agents, for instance diazomethane. Such strong alkylating agents necessitate the complete protection of all reactive sites on the nucleoside bases and the 3' and 5' sugar hydroxyls.

Certain compositions useful for modulating the activity of an RNA or DNA molecule in accordance with this invention generally comprise a sugar modified oligonucleotide containing a targeting sequence which is specifically hybridizable with a preselected nucleotide sequence of single stranded or double stranded DNA or RNA molecule and which is nuclease resistant.

It is generally desirable to select a sequence of DNA or RNA which is involved in the production of proteins whose synthesis is ultimately to be modulated or inhibited in entirety. The oligonucleotide sequence is synthesized, typically through solid state synthesis of known methodology, to be complementary to or at least to be specifically hybridizable with the preselected nucleotide sequence of the RNA or DNA. Nucleic acid synthesizers are commercially available and their use is generally understood by persons of ordinary skill in the art as being effective in generating nearly any oligonucleotide of reasonable length which may be desired.

BRIEF DESCRIPTION OF THE DRAWINGS

The numerous objects and advantages of the present invention may be better understood by those skilled in the art by reference to the accompanying figures, in which.

DETAILED DESCRIPTION OF THE INVENTION

Figure 1A:
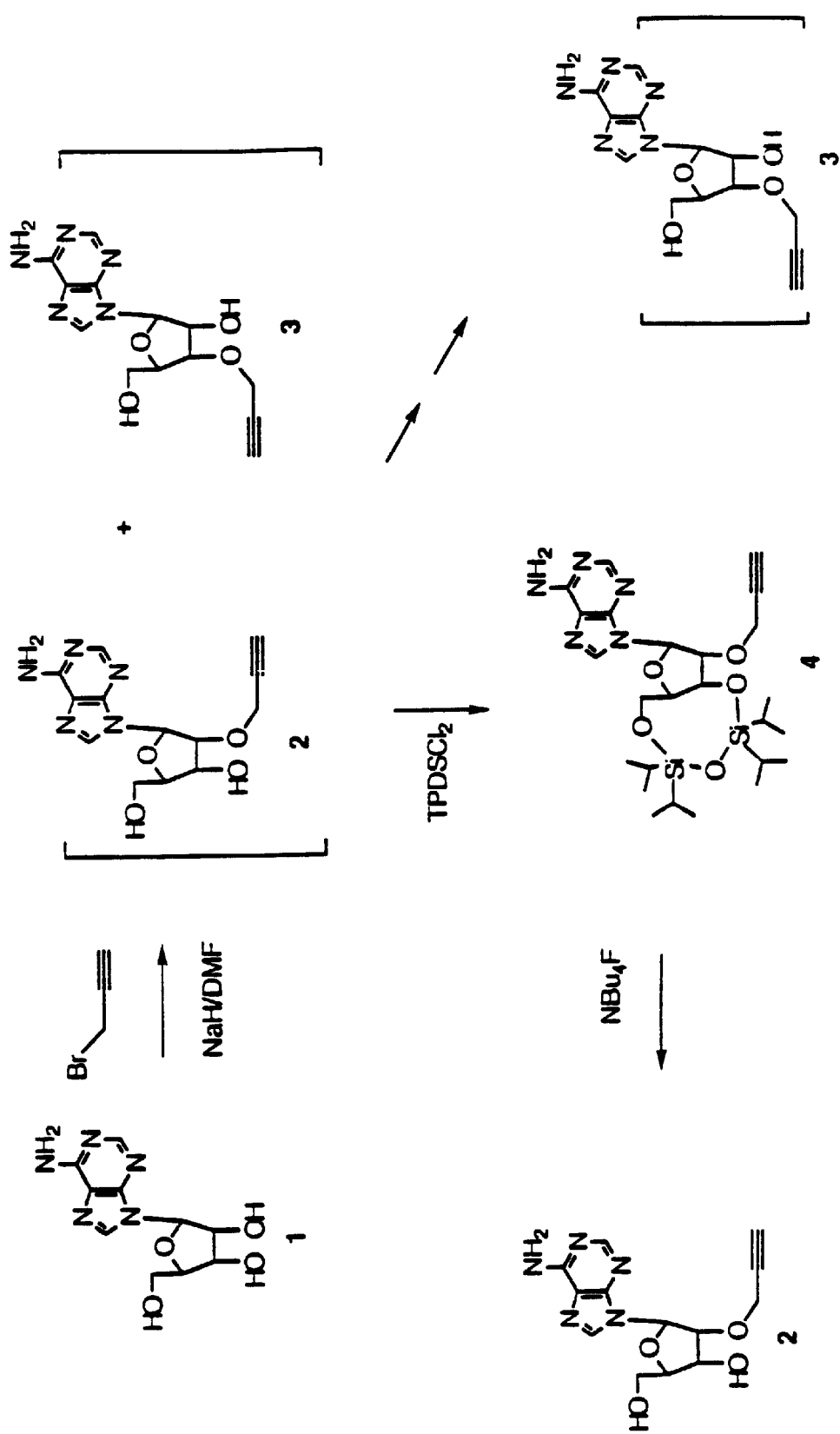
FIG. 1 provides a general synthetic scheme for compound 14.

In the context of this invention, the term "oligonucleotide" refers to polynucleotides formed from a plurality of nucleotide units that contain naturally-occurring bases and pentofuranosyl sugars and that are joined by phosphodiester linkages. The term "oligonucleotide" thus includes naturally occurring species or synthetic species formed from naturally occurring nucleotide units.

The term "oligonucleotide" also includes polynucleotides formed from non-naturally occurring or modified subunits. These modifications can occur on the base portion of a nucleotide, on the sugar portion of a nucleotide or on the linkage joining one nucleotide to the next. In addition, modification can be made wherein nucleoside units are joined through groups that substitute for the inter-nucleoside phosphate or sugar phosphate linkages. Such linkages include those disclosed in U.S. patent application Ser. No. 566,836, filed Aug. 13, 1990, entitled Novel Nucleoside Analogs; Ser. No. 703,619, filed May 21, 1991, entitled Backbone Modified Oligonucleotide Analogs; Ser. No. 903,160, filed Jun. 24, 1992, entitled Heteroatomic Oligonucleoside Linkages; Ser. No. PCT/US92/04294, filed May 21, 1992, entitled Backbone Modified Oligonucleotides; and Ser. No. PCT/US92/04305, all assigned to the assignee of this invention. When other than phosphate linkages are utilized to link the nucleoside units, such structures have also been described as "oligonucleosides."

Other modifications can be made to the sugar, to the base, or to the phosphate group of the nucleotide. Exemplary modifications are disclosed in U.S. patent application Ser. No. 463,358, filed Jan. 11, 1990, entitled Compositions And Methods For Detecting And Modulating RNA Activity; Ser. No. 566,977, filed Aug. 13, 1990, entitled Sugar Modified Oligonucleotides That Detect And Modulate Gene Expression; Ser. No. 558,663, filed Jul. 27, 1990, entitled Novel Polyamine Conjugated Oligonucleotides; Ser. No. 558,806, filed Jul. 27, 1991, entitled Nuclease Resistant Pyrimidine Modified Oligonucleotides That Detect And Modulate Gene Expression; and Ser. No. PCT/US91/00243, filed Jan. 11, 1991, entitled Compositions and Methods For Detecting And Modulating RNA Activity; Ser. No. 777,670, filed Oct. 15, 1991, entitled Oligonucleotides Having Chiral Phosphorus Linkages; Ser. No. 814,961, filed Dec. 24, 1991, entitled Gapped 2' Modified Phosphorothioate Oligonucleotides; Ser. No. 808,201, filed Dec. 13, 1991, entitled Cyclobutyl Oligonucleotide Analogs; and Ser. No. 782,374, filed 782,374, entitled Derivatized Oligonucleotides Having Improved Uptake & Other Properties, all assigned to the assignee of this invention. The disclosures of all of the above noted patent applications are incorporated herein by reference.

Thus, the term oligonucleotide can refer to structures that include modified portions (e.g., modified sugar moieties, modified base moieties or modified sugar linking moieties) that function in a manner similar to natural bases, natural sugars and natural phosphodiester linkages. Representative modifications include phosphorothioate, phosphorodithioate, methyl phosphonate, phosphotriester or phosphoramidate inter-nucleoside linkages in place of phosphodiester inter-nucleoside linkages; deaza or aza purines and pyrimidines in place of natural purine and pyrimidine bases; pyrimidine bases having substituent groups at the 5 or 6 position; purine bases having altered or replacement substituent groups at the 2, 6 or 8 positions; sugars having substituent groups at, for example, their 2' position; or carbocyclic or acyclic sugar analogs. Other modifications consistent with the spirit of this invention are known to those skilled in the art. Such oligonucleotides are best described as being functionally interchangeable with, yet structurally different from, natural oligonucleotides (or synthetic oligonucleotides along natural lines). All such oligonucleotides are comprehended by this invention so long as they can effectively mimic the structure of a desired RNA or DNA strand.

The targeting portions of the compositions of the invention preferably are oligonucleotides having from about 3 to about 50 base units. It is preferred that such oligonucleotides have from about 8 to about 40 base units, more preferably from about 12 to about 25 base units, even more preferably about 15 base units. The targeting portion should be adapted to be specifically hybridizable with the preselected nucleotide sequence of the RNA selected for modulation.

The oligonucleotides believed to be suitable for the practice of the invention comprise one or more subunits having general structure (1a).

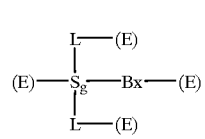

(1a)

wherein Bx is any of the purine or pyrimidine bases, including those which are known for naturally occurring and non-naturally occurring oligonucleotides or which exhibit similar functions; (E) is attached at one or more of the indicated positions and is an RNA cleaving moiety, a group for improving the pharmacokinetic properties of said oligonucleotide, a group for improving the pharmacodynamics of said oligonucleotide, H, OH, or other substituent groups; $S_g$ is a naturally-occurring or non-naturally occurring sugar; and L is a sugar-linking group. The sugar-linking group L may be any of those structures either naturally occurring, described herein, or otherwise known which are capable of linking sugar moieties of oligonucleotides, oligonucleosides or sugar analogs to form the targeting portion of the compositions of this invention. In certain embodiments of this invention, it is preferred that these sugar-linking functions comprise either a phosphodiester structure; a phosphodiester structure wherein at least some of the phosphodiester bonds of said oligonucleotide are substituted with phosphorothioate, methyl phosphonate, or alkyl phosphate; or a structure described in one of the patent applications incorporated above by reference. In other embodiments it is preferred that these sugar-linking functions comprise one or more heteroatoms combined with methylene or other carbon based groups such as are disclosed in the above referenced patent application Ser. Nos. 703,619, 903,160, 566,835, PCT/US92/04294 or PCT/US92/04305.

Persons skilled in the art will recognize that variations in the structures of the sugar moieties of the subject compositions can be made without deviating from the spirit of the invention. It is not necessary that every sugar-linking function be in a modified form. A substantial number and even a predominance of such linking groups can exist in the native, phosphodiester form as long as the overall targeting portion of the composition exhibits an effective ability to specifically bind with a target to form a hybrid capable of detecting and modulating the RNA activity. Of course, fully unmodified, native phosphodiester structures can be used as well.

It is not necessary to tether more than one or perhaps two RNA cleaving functionalities in order to provide the benefits of the invention. Thus, an RNA cleaving moiety preferably is tethered to a relatively small proportion of the subunits, generally only one or two, that together comprise the oligonucleotide or oligonucleoside that is the targeting portion of a composition of the invention. In other embodiments, however, all of the nucleotides in an oligonucleotide or oligonucleoside can be modified to include one or more RNA cleaving moieties. In even further embodiments, one or more or even all of the nucleotides (including those that also carry an RNA cleaving functionality) include pharmacodynamic improving groups or pharmacokinetic improving groups tethered thereto.

It is believed desirable in accordance with certain preferred embodiments to attach the RNA cleaving portion and the intercalating portion of a compositions of this invention to one of the nucleosides forming a subunit of the targeting portion. Such an attachment is depicted by expanding structure (1a) to structure (1b):

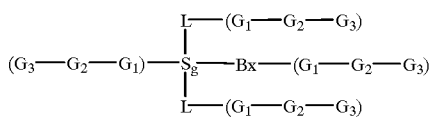

wherein $G_1$ is a bivalent linker, $G_2$ is an aryl or heteroaryl or aryl or heteroaryl containing group and $G_3$ is an RNA cleaving moiety having, for example, general acid/base properties. In certain further preferred embodiments of the inventions, $G_3$ further includes an electrophilic catalyst.

Bivalent linker $G_1$ preferably contains a heteroatom ($G_{1'}$) and an alkyl, alkenyl or alkynyl group ($G_{1''}$) directly in the atomic backbone that leads from the $S_g$, Bx or L group to the $G_2$ group. Preferred heteroatoms include O, S, and N—H or N-alkyl. In certain embodiments of the invention it is preferred that $G_1$ connects to a 2' sugar position of internucleoside linkage thereof. In other preferred embodiments of the invention it is preferred that $G_1$ connects to the internucleoside linkage, i.e. the sugar linking group.

$G_2$ preferably is a polycyclic moiety having from 2 to 6 rings, at least 2 of said rings being joined to form an electronically conjugated system. Representative $G_2$ groups include naphthalene, anthracene, phenanthrene, benzonaphthalene, fluorene, carbazole, pyrido[4,3-b]carbazole, acridine, pyrene, anthraquinone, quinoline, phenylquinoline, xanthene or 2,7-diazaanthracene groups. Structures of this type preferably act as intercalators. Other intercalators believed to be useful are described by Denny, *Anti-Cancer Drug Design* 1989, 4, 241.

RNA-cleaving group $G_3$ can be a functionality that has both general acid and general base characteristics. It also can possess electrophilic catalytic characteristics. It can further possess metal ion coordinating characteristics.

While we do not wish to be bound by any particular theory, general acid/base moieties are believed to function by first deprotonating a target (the general base function). The deprotonated target then can attack a phosphodiester linkage between adjacent nucleotides. The general acid properties are manifested by protonation of an oxygen atom within the phosphodiester linkage. A 2'-hydroxyl group typically is the target of the general base such that a 2'-oxygen-centered anion serves as a nucleophile towards the phosphodiester linkage. The 5'-hydroxyl or the phosphate oxygen is protonated by the general acid and serves as a leaving group. The overall result is cleavage of a phosphodiester linkage between a phosphate group and a 5' hydroxyl group. This process can be further assisted by the provision of an appropriate electrophilic catalytic group or groups in close proximately to the phosphate. Such electrophilic catalytic groups are described by H. Dugas, *Bioorganic Chemistry, A Chemical Approach to Enzyme Action*, 2nd Ed., Springer-Verlag, NY, 1989.

The above-described general acid/base mechanism and the general acid/base mechanism augmented with electrophilic catalysis thus excludes the nitrogen mustards (see, e.g., Kohn, et al., *Nucleic Acid Research* 1987, 24, 10531 for a review of nitrogen mustard type molecules), photoactive molecules such as psoralens (see, e.g., Cimino, et al., *Ann Rev. Biochem.* 1985, 54, 1151 for a review of photoactive psoralens), and the alkylating agents described by Vlassov, et al., *Nucleic Acids Research* 1986, 14, 4065.

In certain preferred embodiments, $G_3$ includes a 5- or 6-membered heterocyclic ring, preferably a heterocyclic ring that contains at least one nitrogen atom, more preferably at least one imidazole group. A more preferred group for $G_3$ for this embodiment includes an imidazole, a C2-substituted imidazole, an imidazole substituted at one of its C4 or C5 positions with an electrophilic catalyst, a bis-imidazole, a C2-substituted bis-imidazole, a bis-imidazole wherein at least one C4 or C5 position is substituted with an electrophilic catalyst, a bis-imidazole wherein both of its C4 positions or both of its C5 positions are substituted with electrophilic catalyst or a bis-imidazole wherein the linkage connecting the individual imidazole rings of the bis-imidazole is substituted with an electrophilic catalyst. The electrophilic catalyst preferably includes a nitrogen functionality that can be protonated, preferably an amine, a nitrogen heterocycle, guanidine or amidine. In preferred embodiments of the invention, these nitrogen functionalities are "preorganized" for optimal interactions with one or any of the four oxygen atoms of a phosphate backbone and neighboring 2'-hydroxyl of a target nucleic acid.

Bis-imidazoles are also preferred general acid/base RNA cleavers. Bis-imidazole moieties are those wherein two imidazole rings are joined via a linking group. Bis-imidazoles can be prepared utilizing the general procedures described by Tang, et al., *J. Am. Chem. Soc.* 1978, 100, 3918. The linking groups connecting bis-imidazoles will include one or more tethering groups for connecting the bis-imidazole to other functionality. Preferred tethering groups are hydroxyl, carboxy, amine and thiol groups; hydroxyl and carboxy groups are particularly preferred. Other tethering groups include planar aromatic ring systems. The carboxy moiety allows for tethering the bis-imidazole via ester and amide linkages.

$G_2$ and $G_3$ can be connected by a single covalent bond or by a mono- or polyatomic bivalent linker. Covalent bonds and bivalent linkers also can be used in tandem to connect between the $G_2$ and $G_3$ groups through, for example, two different atomic positions on each group. The bivalent linker can include an electrophilic catalyst directly in the atomic backbone leading from $G_2$ to $G_3$ or attached to the backbone in a pendant fashion. In preferred embodiments, $G_3$ includes at least one imidazole group and a single covalent bond and/or bivalent linker at position C4 and/or C5 of such imidazole group leading to the $G_2$ group. With use of both a single covalent bond and a bivalent linker, two tandem points of connections are provided between the $G_3$ and the $G_2$ groups.

In other preferred embodiments, $G_3$ includes two imidazole rings linked to $G_2$ via one or more one of an acyl, an amine, a thiol, an aryl, a substituted aryl, an alkyl or a substituted alkyl or combinations of these groups. As used herein acyl groups include keto, carboxyl, ester and amide linkages and combinations of amines and thiol includes sulfamides. Amides are particularly preferred since they are stable to the reactions conditions normally utilized during oligonucleotide synthesis utilizing commercial DNA synthesizers and commercial reagents.

In even further preferred embodiments, $G_3$ will include one or more carbocyclic, heterocyclic or aromatic ring (both single and multiple ring) structures that together with further linear tethers and linkers define structures that position one or more ligands in a three dimensional array to coordinate with one or more metal ions. Further, $G_3$ will be linked to $G_2$ to then fix those ligands and metal ions they coordinate with in preferred spacial configurations with respect to target strands.

Certain preferred compounds according to the invention have structure (1c):

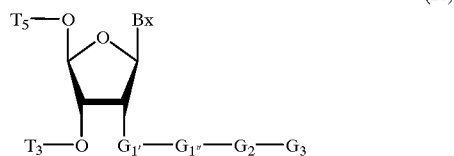

wherein $G_{1'}$, $G_{1''}$, $G_2$ and $G_3$ are as defined above and $T_5$ is H, a hydroxyl protecting group, a phosphate group, a nucleotide or an oligonucleotide; $T_3$ is H, a hydroxyl protecting group, a nucleotide, an oligonucleotide, a phosphate group, an activated phosphate group or a solid phase support; and Bx is a heterocyclic base moiety, preferably a purine. In certain useful synthetic intermediates of the invention, $G_1$—$G_2$—$G_3$ is alkynyl, preferably propargyl, provided that when Bx is uracil then $T_3$ and $T_5$ are not H or acetyl. 2'-O-propargyl moieties have been used as intermediates in the synthesis of certain caged borane compounds or as structural analogs to AZT (see, Anisuzzaman, et al., *Polyhedron* 1990, 9, 891; Solway, *Pure & appl. Chem.* 1991, 63, 411; and Rosowsky, et al., *Nucleosides & Nucleotides* 1989, 8, 491). As shown in the examples below, the propargyl linkage can be stepwise reduced to a propene and then a propyl linkage. The propargyl, propene or propyl nucleoside intermediates are potentially useful as antiviral agents.

Compounds having structure (1c) wherein $T_5$ and $T_3$ are hydroxyl protecting groups and $G_{1''}$ is alkynyl preferably are prepared by contacting a compound having structure (1d) with a compound having structure $T_6O$—$G_2$—$OT_6$ in the presence of a nucleophile and a palladium catalyst to produce a compound having structure (1e). In this structure $T_6$ is a hydroxyl activating group such as trifluoromethylsulfonyl (a triflate or trf group).

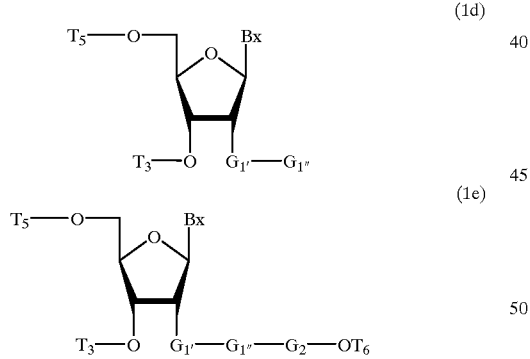

In treating compound (1d) to form compound (1e) use of the $T_3$ and $T_5$ hydroxyl blocking groups is optional. Use of such blocking groups allows for the initial preparation of the compound (1d) under more rigorous reaction conditions since concurrent substitution of either the 3' or 5' hydroxyl group during substitution of the 2'-hydroxyl group need not be considered. If blocking groups are not utilized, in preparing compound (1d), 2'-O substitution is conducted in a regioselective manner to selectively substitute (or predominantly selectively substitute) the 2' position in preference to the 3' or 5' positions. If $T_3$ and/or $T_5$ blocking groups are selected, since essentially pH neutral reaction conditions are utilized in converting compound (1d) to compound (1e), consideration of acid or base stability of the $T_3$ and $T_5$ hydroxyl blocking groups is not necessary. Thus, various of the known hydroxyl blocking groups can be utilized. Such blocking groups can be selected from those known to the art skilled. A recent review of such blocking groups is found in Beaucage, et al., *Tetrahedron* 1992, 48, 2223. A particularly useful blocking groups is the tetraisoproyldisiloxanyl group since it concurrently blocks both the 3' and the 5' hydroxyl positions. Thus in preferred embodiments, $T_3$ and $T_5$ together form a 3',5'-O-tetraisoproyldisiloxanyl group.

$T_6$ is selected such that $T_6O$ is a good leaving group. Preferably, $T_6$ is trifluoromethylsulfonyl. Other suitable leaving groups include iodo and bromo. Displacement of the $T_6$ leaving group is conducted in the presence of a catalyst, preferably a palladium catalyst. One preferred palladium catalyst is $Pd(PPh_3)_4$. A further palladium catalyst in $PdCl_2(PPh_3)_2$.

Compound (1e) then is contacted with a compound having structure $T_7$-$G_3$-M-$T_8$ to form compound (1c). This reaction also is effected in the presence of a catalyst. As with the above-described catalytic reaction, palladium (preferably $Pd(PPh_3)_4$) is selected as the catalyst. In palladium-catalyzed reactions M preferably is selected to be Sn. $T_8$ should be a poly-alkyl group with alkyl being from about 1 to about 5 carbon atoms. Preferably $T_8$ is tris-butyl. $T_7$ is a regio protecting group or is $R_C$ as outlined below. Such $R_C$ groups also can include appropriate protecting groups. Presently preferred regio protecting groups include a t-butyldimethylsilyl or t-butyldimethylsilyl group.

A number of particularly preferred compounds of the invention have structures (2a)–(5c):

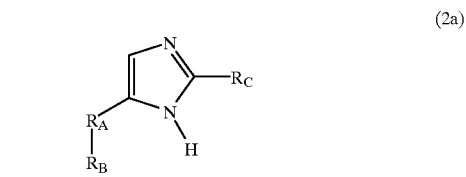

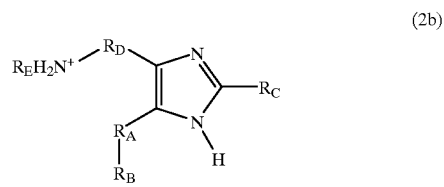

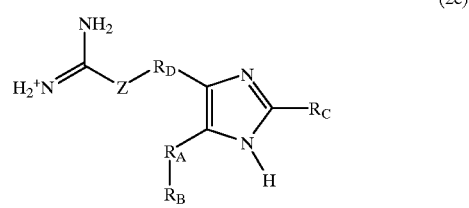

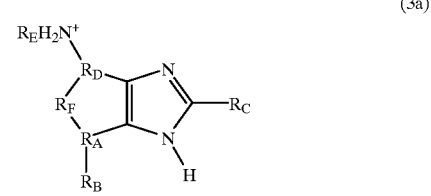

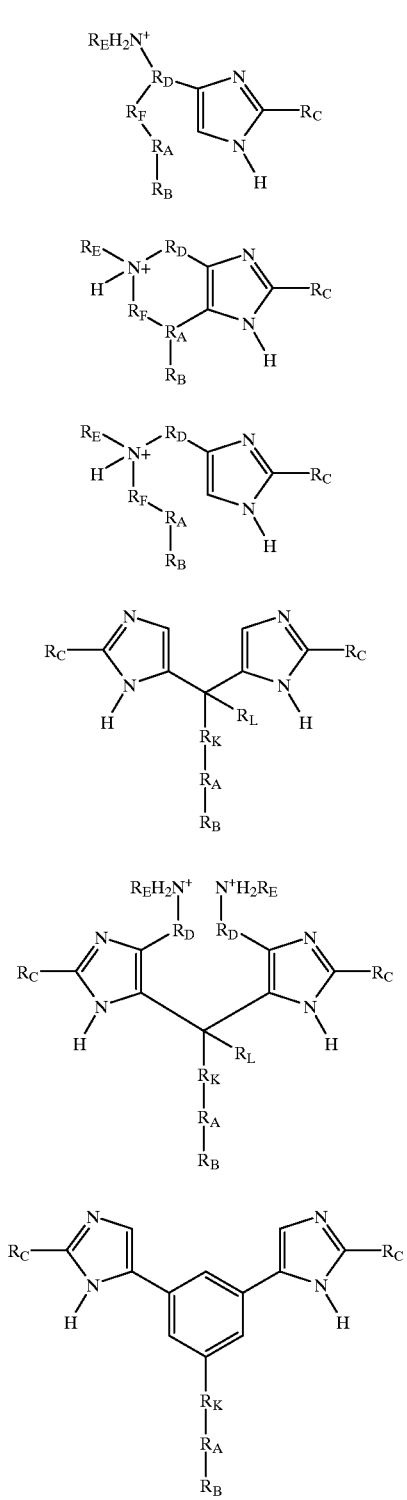

wherein:

$R_A$ is aryl, substituted aryl, or nitrogen heterocyclic;

$R_B$ is $S_g$—$G_{1'}$—$G_{1''}$, $S_g$—, Bx-, or L-;

$R_C$ is H, O$^-$, COO$^-$, OR$_G$, NH$_2$, C(R$_G$)(R$_H$)(R$_I$), N(R$_G$)(R$_H$)(R$_I$), Cl, Br, F, CF$_3$, SR$_G$, NHC(O)R$_G$, OC(O)R$_G$, NO, nitrogen heterocyclic or another electron donating group;

$R_D$ is (CH$_2$)$_q$;

$R_E$ is H, (CH$_2$)$_n$—R$_J$, or a chemical functional group comprising R$_J$;

$R_F$ is C$_1$–C$_{20}$ alkyl, C$_2$–C$_{20}$ alkenyl or C$_2$–C$_{20}$ alkynyl, aryl, or cycloalkyl;

$R_G$, $R_H$, and $R_I$ are, independently, H, C$_1$–C$_{10}$ alkyl, or substituted alkyl;

$R_J$ is H, nitrogen heterocyclic, a positively charged group, or a phosphoryl hydrogen bond donating group;

$R_K$ is alkyl, acyl or acyl-alkyl;

$R_L$ is H or OH;

Z is NH$_2$ or CH$_2$;

Bx is a purine or pyrimidine base or a derivative thereof;

L is a sugar-linking group;

$S_g$ is a naturally occurring or non-naturally occurring sugar;

$G_{1'}$ is O, S, NH or N-alkyl;

$G_{1''}$ is C$_1$–C$_{20}$ alkyl, C$_2$–C$_{20}$ alkenyl or C$_2$–C$_{20}$ alkynyl;

n is from about 1 to about 5; and q is from about 0 to about 5.

$R_A$ preferably is selected to promote intercalation between the base pairs of the oligonucleotide/RNA target sequence heteroduplex. $R_A$ is selected such that it will make a major contribution to the net intercalative binding energy. The other contributions to the net intercalation energy is derived from the imidazole ring portion of structures (2a)–(5c). Representative $R_A$ include phenyl, substituted phenyl, naphthyl, anthracenyl, 2,7-diaza-anthracenyl, pyrenyl, acridinyl, 9-aminoacridinyl, quinolinyl, pyrido-quinolinyl and pyridinyl moieties. $R_A$ preferably is a polycyclic aromatic hydrocarbon such as a naphthyl residue. Preferred polycyclic aromatic hydrocarbons are non-carcinogenic moieties that do not bind RNA or DNA with either high affinity or a strong sequence dependence, i.e. so-called "minimal" intercalators.

According to the present invention, $R_B$ is a covalent linker joining $R_A$ to a sugar moiety, to a base moiety, or to a sugar-linking moiety. In certain preferred embodiments, $R_B$ is $S_g$-2'—O—CH$_2$—CH$_2$— or $S_g$-2'—O—(CH$_2$)$_3$—NH—CO—.

$R_C$ preferably is electron donating, through inductive and/or resonance effects. It is believed that $R_C$ serves to upwardly adjust the pK$_a$ of the imidazole residue in structures (2a)–(5c). In a steric sense, $R_C$ is intended to lie in the RNA minor groove without affecting RNA hybridization or intercalative binding via $R_A$ and/or the imidazole residue. $R_C$ may be designed to contain a proton-accepting group to assist deprotonation of the 2' hydroxyl of a target RNA.

$R_D$ preferably is a covalent linker joining the 5-position of the imidazole residue and the amine function, H$_2$R$_E$N$^+$. $R_D$ preferably comprises about 1–5 carbon atoms. However, R$_D$—N$^+$H$_2$R$_E$ need not be present. As will be recognized, the existence of the amine function in either protonated or neutral form is media dependent. The amine function is intended to lie in one of the RNA major or minor grooves and to complex with the RNA internucleotide phosphate diester through electrostatic and/or hydrogen bonding to RNA phosphate oxygens. Such complexation is intended to properly orient RNA cleaving moieties such as the imidazole residue and to directly enhance the rate of cleavage. Such rate enhancement is believed to be effected through polarization and weakening of RNA phosphorus-oxygen bonds, making the phosphorus atom more electrophilic and more reactive to attack by a 2'-oxygen atom. The amine function is also believed to stabilize the resulting transition states and intermediates, making the phosphate oxygens better proton acceptors.

In preferred embodiments, $R_E$ comprises an alkyl chain of up to about 3 carbon atoms and a further moiety known to assist RNA cleaving, $R_J$. Preferably, $R_J$ is a nitrogen heterocycle, more preferably an imidazole. This function is intended to pre-protonate one of the two non-ester linkage phosphoryl oxygens in an initial chemical step to make the phosphorus more electrophilic and reactive to attack by a 2' oxygen anion, $O^-$. It is particularly preferred that $R_J$ have one of the structures:

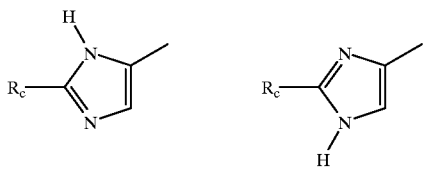

where $R_C$ is as defined above or is a group that can hydrogen bond with or electrostatically interact with phosphate oxygens. In other preferred embodiments, $R_J$ is guanidino or amidino. Such structures are selected for further electrophilic complexation of the phosphate backbone of a target nucleic acid. Guanidine and amidine structures are illustrated in structure (5c).

$R_F$ is a conformation-restricting moiety of variable size linking $R_A$ and the amine function. It can be mono- or polycyclic and/or acyclic, as well as saturated and/or unsaturated. $R_F$ preferably is $(CH_2)_n$ where n is 1–3.

Three representative imidazole-based, RNA-cleaving oligonucleotides according to the present invention are depicted by structures (11)–(13), wherein DMT is dimethoxytrityl, CEO is cyanoethoxy, and Bz is benzoyl. The latter are protective blocking groups of synthesis.

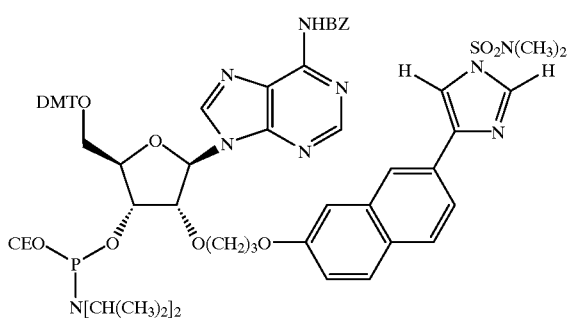
(11)

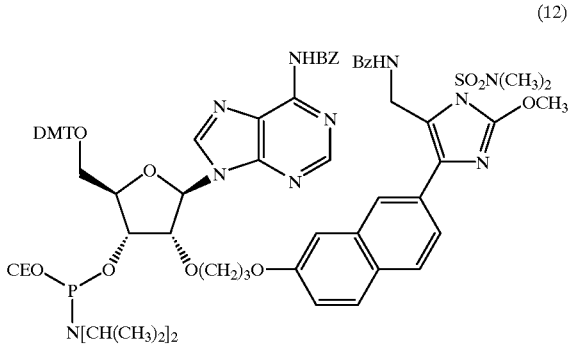
(12)

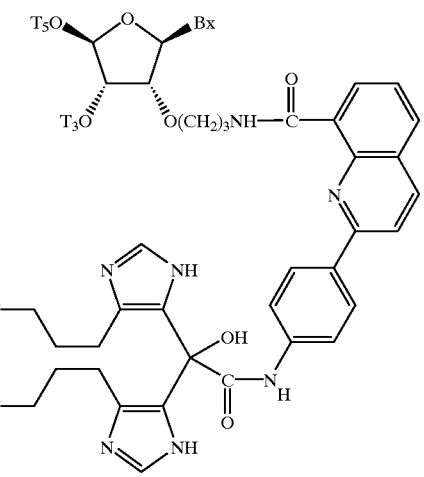
(13)

While not intending to be limited to any particular theory of the invention, it is believed that when the oligonucleotides of the present invention hybridize with RNA, the $R_A$ and, to a lesser extent, any imidazole subunits appended to the 2' positions thereof, intercalate with the RNA and thereby are constrained by the hybrid duplex to a fairly limited number of positions and conformations in comparison to designs lacking the intercalative moiety. By constraining the intercalative cleaver with the duplex in this manner, the specific RNA cleaving functionality is positioned for optimal delivery to hybridized RNA. It should be noted that limited local motion and positioning via the intercalative mode are allowed, such that the positively charged amine of structures (2b)–(5c) can optimally fine-tune the orientation of the entire composition by hydrogen bonding and electrostatic interactions with the phosphate groups while retaining an intercalative binding mode. Accordingly, it is intended that the present invention include as a preferred embodiment all compositions comprising a ribofuranosyl nucleotide which bears at its 2' position substituents capable of both intercalating and cleaving RNA. The same substituents capable of both intercalating and cleaving RNA also may be functionalized via a suitable linker to any of the bases or to the oligonucleotide backbone.

It will be recognized that structures (2a)–(5c) can be coupled with the sugar portion of a given nucleoside at a variety of positions including, but not limited to, the 2' hydroxyl group as shown, for example, in structures (14) and (15):

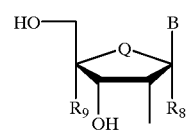
(14)

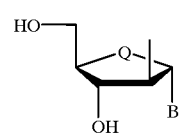
(15)

wherein:
Q is O, S or $CR_{11}$;
$R_8$ and $R_9$ are H, lower alkyl, substituted lower alkyl, a group which improves the pharmacokinetic properties of an oligonucleotide, a group which improves the pharmacodynamic properties of an oligonucleotide, or one of structures (2a)–(5c), absent the $R_B$ group;

$R_{11}$ is H, lower alkyl, substituted lower alkyl, an RNA cleaving moiety, a group which improves the pharmacokinetic properties of an oligonucleotide, or a group which improves the pharmacodynamic properties of an oligonucleotide; and Bx is a nucleoside base or blocked nucleoside base moiety.

Alkyl groups of the invention include but are not limited to $C_1$–$C_{12}$ straight and branched chained alkyls such as methyl, ethyl, propyl, butyl, pentyl, hexyl, heptyl, octyl, nonyl, decyl, undecyl, dodecyl, isopropyl, 2-butyl, isobutyl, 2-methylbutyl, isopentyl, 2-methyl-pentyl, 3-methylpentyl, 2-ethylhexyl and 2-propylpentyl. Alkenyl groups include but are not limited to unsaturated moieties derived from the above alkyl groups including but not limited to vinyl, allyl and crotyl. Alkynyl groups include unsaturated moieties having at least one triple bond that are derived from the above alkyl groups including but are not limited to ethynyl and propargyl. Aryl groups include but are not limited to phenyl, tolyl, benzyl, naphthyl, anthracyl, phenanthryl, pyrenyl, and xylyl. Halogens include fluorine, chlorine and bromine. Suitable heterocyclic groups include but are not limited to imidazole, tetrazole, triazole, pyrrolidine, piperidine, piperazine and morpholine. Amines include amines of all of the above alkyl, alkenyl and aryl groups including primary and secondary amines and "masked amines" such as phthalimide. Amines are also meant to include polyalkylamino compounds and aminoalkylamines such as aminopropylamine and further heterocycloalkylamines such as imidazol-1, 2 or 4-yl-propylamine. Substituent groups for the above include but are not limited to other alkyl, haloalkyl, alkenyl, alkoxy, thioalkoxy, haloalkoxy and aryl groups as well as halogen, hydroxyl, amino, azido, carboxy, cyano, nitro, mercapto, sulfides, sulfones and sulfoxides. Other suitable substituent groups also include rhodamines, coumarins, acridones, pyrenes, stilbenes, oxazolo-pyrido-carbazoles, anthraquinones, phenanthridines, phenazines, azidobenzenes, psoralens, porphyrins and cholesterols.

In a further embodiment of the invention one or more metal ions are utilized to effect catalysis of RNA cleavage. In cellular systems the metal ions are obtained in situ from the cellular system. For use as artificial restriction enzymes, the metal can be added with the compound of the invention as a preformed complex. In any event, the compounds of the inventions include one or more ligand tethers located in a selected geometry so as to coordinate, chelate or multidentate the metal ion in a defined position with respect to the target RNA of interest that is to be cleaved.

For in situ RNA cleavage, ligands are selected for preferably coordinating to magnesium. Other metals of interest include calcium and zinc. In a preferred embodiment, while we do not wish to be bound by theory, a total of eight ligands are provided to coordinate to two magnesium ions. Other coordination sites on the ions are taken up by water or they become exchanged with substrate oxygens. In providing eight ligands, each magnesium can be inner sphere coordinated to two equatorial ligands and to two axial ligands on the compound of the invention. Preferably the ligands of the compounds of the invention are selected to provide for co-planar positioning of the equatorial ligands. Preferably the ligands of the compounds of the invention are selected to position the metal ions such that the two metal ions can further share coordination to one water molecule at a remaining equatorial coordination site with the remaining equatorial site of each magnesium available to bind to free water. It is believed that the coordinated metal ions will have a strong template effect, will serve as general acids, general bases and will be potent electrophilic catalysts.

Preferably the ligands are tethered via linking arms that fix the ligands in space with respect to one another for forming the coordination complex with the metal. Particularly suitable for ligands are hetero atoms including oxygen, sulfur and nitrogen species. Presently, most preferred is oxygen. An appropriate organic group is used to position or tether the hetero atom in position for coordination with the metal. For an oxygen atom, preferred for such positioning groups are selected to be alcohols, ketones, aldehydes, ethers and acids. Corresponding like species are used for positioning nitrogen and sulfur species.

While we do not wish to be bound by theory, it is presently believed that a compound of the invention is best positioned on a carrier oligonucleotide or oligonucleoside such that there will be a mismatch on a target strand at a site proximal to the compound of the invention between the carrier oligonucleotide or oligonucleoside and the target strand. It is presently believed that this mismatch referably should be a single base mismatch. The positioning of the RNA cleaver portions of the compounds of the inventions resently is thought to be preferably in the minor groove in close approximation to the internucleoside phosphate 5'- to the single base mismatch and is facilitated by the presences of an intercalator forming an integral part of the compounds of the invention. It is further believed that the intercalator portion of the compounds of the invention will prevent intercalation of the mismatched base at the target, which will be forced outward, away from the duplex. This, together with separation of the base-pair above and below the mismatch by the intercalator is thought to position the internucleoside linkage 5'- to the mismatch. Such positioning is favorable both sterically and stereochemically.

A representative ligand based RNA-cleaving compound according to the invention is depicted by structure (16) wherein X and Y are groups for coordinating metal ions.

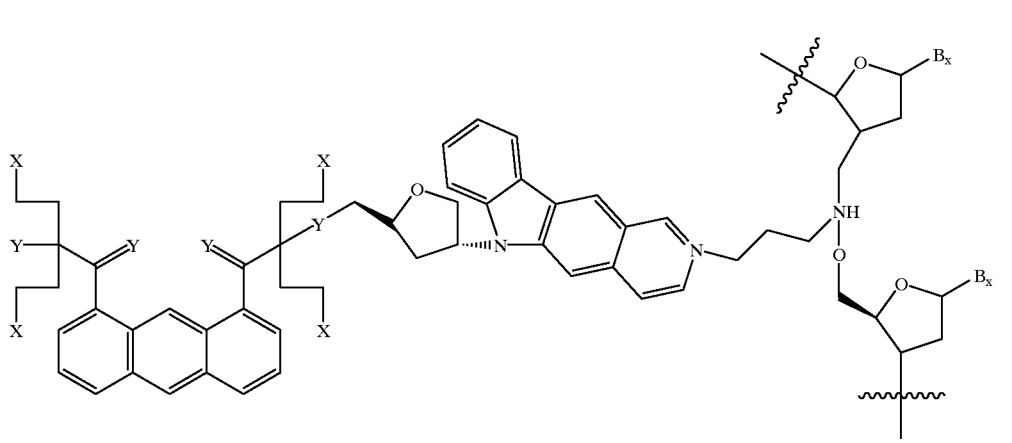

(16)

Preferably the X and Y groups will include at least one hetero atoms. Preferably such hetero atoms are selected from oxygen, sulfur and nitrogen with oxygen being the most preferred. Preferably the hetero atom of the X groups for compounds of structure (16) will form a part of an ether, alcohol or acid moiety. Preferably the hetero atom of the Y group of compounds of structure (16) will form a part of an ether, ketone or alcohol.

The tethers and other structures linking the X and Y groups to the remainder of the molecule are selected to position the X and Y groups in space to facilitate coordination with metal ions. Particularly preferred for these tethers are single or double covalent bonds or lower alkyl, alkenyl or alkynyl groups of from about 2 to about 12 carbon atoms in length, aryl or aralkyl rings, heterocyclic rings and alicyclic ring structures. Such structures can be joined in or form a part of larger skeletal structural features including multi-functional groups, multiple ring systems or linked ring systems that serves to support the X and Y coordinating hetero atoms and to position them in space to coordinate with one or more metal ions.

Compounds of the inventions of structure (16) preferably are attached to an oligonucleotide or oligonucleoside via the internucleoside linkage of such oligonucleotide or oligonucleoside, as for instance as shown in structure (16) by tethering to an internucleoside methyleneimino linkage linking two nucleosides of an oligonucleotide or oligonucleoside molecule. Such a methyleneimino linkage is described in the above referenced patent application Ser. No. 703,619. It has further been published in Vasseur, J.-J., Debart, F., Sanghvi, Y. S. and Cook, P. D., *J. Am. Chem. Soc.*, 1992 114, 4006.

In structure (16), a pyrido[4,3-b]carbazole ring serving as a $G_2$ intercalator is linked via a $G_1$ bivalent propyl tether that extends from a hetero atom in the internucleoside backbone of the oligonucleoside to a further hetero atom of the pyridine ring of the pyrido[4,3-b]carbazole ring. The $G_3$ RNA cleaving moiety consists of four X hetero atoms, preferably ether, alcohol or acid oxygen atoms, and four Y hetero atoms, preferably ether, keto or alcohol oxygen atoms that are arranged in space via four alkyl tethers connecting the X moieties and one alcohol, one ether and two keto groups connecting the Y moieties. A combination of an anthracene ring and a pentofuranose ring support and connect these to the intercalator $G_2$ moiety. The $G_2$ moiety in turn is connected via the $G_1$ tether to the internucleoside linkage of an oligonucleotide or oligonucleoside. The anthracene ring can include further substitution thereon as, for instance, a bulky group to inhibit intercalation of the anthracene ring between bases or base-pairs. If used, such bulky group, i.e. t-butyl or the like, preferably would be located distal from the 1,8 positions of the anthracene ring where the tethers connect to this ring as for instance at position 10 of the anthracene ring.

The nucleosidic sites to which functionality may be attached, and the design of any intervening linker group, are critical to the design of compositions for sequence-specific destruction or modulation of targeted RNA. The functionality must not interfere with Watson-Crick base pair hydrogen bonding rules, as this is the sequence-specific recognition/binding factor essential for selection of the RNA to be disrupted. The nucleosidic sites of functionalization also must not preclude optimal placement of the functionalized composition to best fulfill structural and functional goals.

Approaches to perfect complementation between the modified oligonucleotides and targeted RNA will result in the most stable heteroduplexes. This is desired because the heteroduplex must have a half-life sufficient to allow the reactive or non-reactive functionalities of this invention to initiate RNA cleavage or disruption of RNA function.

The half life of a perfectly formed duplex will be greatly affected by the positioning of the tethered functional group. Inappropriate positioning of functional groups, such as placement on the Watson/Crick base pair sites, would preclude duplex formation. Other attachment sites may allow sequence-specific binding but may be of such low stability that the reactive functionality will not have sufficient time to initiate RNA disruption.

For RNA inactivation, another important factor concerning the placement of the tethered functionality is that it must have optimized molecular recognition with the receptive substrate located in the targeted RNA, for example of a general base group with the 2'-hydroxyl group. A variety of structural studies such as X-ray diffraction, chemical reaction, and molecular modeling may aid in this placement.

Those positions on the nucleosides of double-stranded nucleic acids that are exposed in the minor groove may be substituted without affecting Watson-Crick base-pairing or duplex stability. Such sites are preferred for attachment of the reactive functionalities of the invention. The reactive functionalities attached to these positions in accordance with this invention may initiate cleavage and destruction of targeted RNA or interfere with its activity.

Reactive functionalities or pendant groups of oligonucleotides previously described in the literature have been almost exclusively placed on a phosphorus atom, the 5-position of thymine, or the 7-position of purines. A phosphorus atom attachment site can allow a reactive group to access both the major and minor grooves or to intercalate between base pairs. However, internal phosphorus modification can result in greatly reduced heteroduplex stability except with intercalator placement. Attachments at the 3' and/or 5' ends are limiting in that only one or two functional groups can be accommodated in the oligonucleotide. Even successful cleavage will not drive release of the cleaved moiety. Functionality placed in the 5-position or 7-position of heterocycles (bases) pyrimidine and purine respectively will reside in the major groove of the duplex and will not be in proximity to the RNA 2'-hydroxyl substrate. However, such functional placement may be used to link to an intercalator bound between base pairs. Further, such placement can interfere with Watson-Crick binding.

Pendant groups that do not cleave RNA also can be attached to the oligonucleotides of the invention. In certain embodiments, such groups do not possess a reactive functionality but serve to enhance the pharmacodynamic and/or pharmacokinetic properties of an oligonucleotide. In this context, pharmacodynamic property improvement means improved oligonucleotide uptake, enhanced oligonucleotide resistance to degradation, and/or strengthened sequence-specific hybridization with RNA. Pharmacokinetic property improvement means, in this context, improved oligonucleotide uptake, distribution, metabolism or excretion. Such pendant groups do not initiate chemical reactions. They preferably include alkyl chains, polyamines, ethylene glycols, polyamides, aminoalkyl chains, amphipathic moieties, points for reporter group attachment, and intercalators attached to any of the preferred sites for attachment.

It is possible that other positions will be found for attachment of the RNA cleaving moieties to nucleosides, nucleotides, or oligonucleotides, particularly when further modification of the purine or pyrimidine structure is undertaken or when backbone analogs suitable for functionalization are found, as may be done by persons of ordinary skill in the art without deviating from the spirit of the present invention. It will be understood that preferably one or at most a few RNA cleaving moieties generally should be employed. Thus, artisans in the field will have great latitude in selecting means of attachment of the RNA cleaving moieties, the pharmacodynamic improving groups or the pharmacokinetic improving groups in accordance with this invention.

The RNA cleaving moieties of the compositions of the present invention are designed in such a fashion that they can be effective in performing their proximate task, leading to the desired modulation of RNA activity. It is believed to be useful to employ heteroatomic substitutions in the RNA cleaving moieties of these molecules, especially amides and polyamides, and indeed some may be preferred in order to ensure even tighter binding between the target mRNA and the compositions of the invention.

The nucleosides of the invention are linked together and to the rest of the oligonucleotide through a sugar-linking group. The linking group may be any of those structures described herein that are capable of linking sugar moieties of oligonucleotides together to form the targeting portion of the compositions of this invention. These can comprise phosphodiester type linkages or derivatives thereof. Derivatives of the phosphodiester structure may include substitution of a sulphur, methyl, methyl oxide, or amine group for an oxygen. The sugar phosphate nucleic acid backbone may be modified as a phosphorothioate, phosphorodithioate, methylphosphonate, or phosphate alkylated moiety. The phosphodiester linkage may also be replaced other hetero atom backbones as discussed above.

Without desiring to be bound by any particular theory of operation, it is believed that the reactive RNA cleaving functionalities described in this invention work by mechanisms involving any or all of:

1. phosphodiester bond cleavage via general acid/base catalysis with or without assistance via H-bonding, electrostatic interactions, electrophilic catalysis or template effects;
2. backbone sugar cleavage;
3. base alkylation cleavage; or
4. sugar alkylation, i.e., 2'-hydroxyl cross-linking.

One important aspect of this invention is the position and orientation of an appropriate reactive functionality of the targeting portion of this invention and the target RNA.

Phosphodiester bond cleavage can be accomplished by strategically positioning either proton-accepting, proton-donating, or electron-accepting functional groups, represented by X, Y, and Z respectively, adjacent to such phosphodiester bonds, as shown in Scheme 1, wherein $B_1$ and $B_2$ are nucleoside base units. Additional placement of a proton-donating group, W—H, adjacent to one of the non-ester linkage phosphoryl oxygens may provide additional enhancement of cleavage.

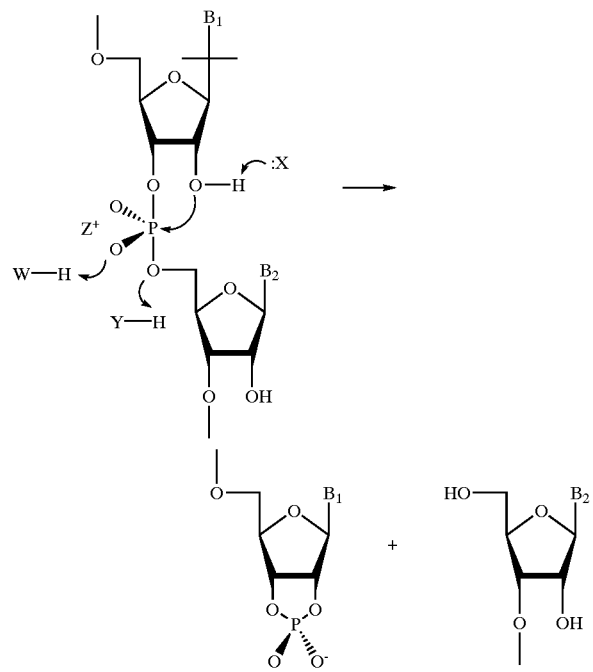

Scheme 1

In some applications, one of the chemical groups may be sufficient to catalyze RNA cleavage. However, in other applications of the invention, the combination of two or even three groups may be preferred. Artisans in the field will have great latitude in selecting the specific reactive functionalities W, X, Y, and/or Z. There is also great latitude in the election to use one or more reactive functionalities in the same molecule.

The present novel approach to obtaining stronger binding and better molecular recognition of cleavage groups with target reactive groups is to prepare antisense RNA mimics to bind to the targeted RNA. Therefore, a structure-activity relationship approach is undertaken to discover nuclease resistant antisense oligonucleotides that maintain appropriate hybridization properties.

A series of 2'-modified nucleosides of adenine, guanine, cytosine, thymidine and certain analogs of these bases are prepared and are inserted as the modified nucleosides into sequence-specific oligonucleotides via solid phase nucleic acid synthesis. The novel antisense oligonucleotides are assayed for their ability to resist degradation by nucleases and to possess hybridization properties comparable to the unmodified parent oligonucleotide. Initially, small electronegative groups are selected because these types are not likely to sterically interfere with required Watson-Crick base pair hydrogen bonding (hybridization). However, electronic changes due to the electronegativity of the atom or group in the 2'-position may profoundly effect the sugar conformation.

The oligonucleotides of this invention can be used in diagnostics, therapeutics, and as research reagents and kits. For therapeutic use, the oligonucleotide is administered to an animal suffering from a disease effected by a protein. Representative antisense approaches to one such disease, papillomavirus infection, are generally provided by U.S. patent application Ser. No. 445,196, filed Dec. 4, 1989, the contents of which are incorporated herein by reference.

Oligonucleotides can be formulated in a pharmaceutical composition, which can include carriers, thickeners, diluents, buffers, preservatives, surface active agents and the like in addition to the oligonucleotide. Pharmaceutical compositions also can include one or more active ingredients such as antimicrobial agents, anti-inflammatory agents, anesthetics, and the like in addition to oligonucleotide.

The pharmaceutical composition can be administered in a number of ways depending on whether local or systemic treatment is desired, and on the area to be treated. Administration can be topically (including opthalmically, vaginally, rectally, intranasally), orally, by inhalation, or parenterally, for example by intravenous drip, subcutaneous, intraperitoneal or intramuscular injection.

Formulations for topical administration can include ointments, lotions, creams, gels, drops, suppositories, sprays, liquids and powders. Conventional pharmaceutical carriers, aqueous, powder or oily bases, thickeners and the like may be necessary or desirable. Coated condoms may also be useful.

Compositions for oral administration include powders or granules, suspensions or solutions in water or non-aqueous media, capsules, sachets, or tablets. Thickeners, flavorings, diluents, emulsifiers, dispersing aids or binders may be desirable.

Formulations for parenteral administration can include sterile aqueous solutions which also can contain buffers, diluents and other suitable additives.

Dosing is dependent on severity and responsiveness of the condition to be treated, but will normally be one or more doses per day, with course of treatment lasting from several days to several months or until a cure is effected or a diminution of disease state is achieved. Persons of ordinary skill can easily determine optimum dosages, dosing methodologies and repetition rates.

The following procedures and examples illustrate the practice of this invention. These procedures and examples are not to be construed as limiting the invention.

Once nucleotides of the invention have been prepared, they can then subsequently be incorporated into oligonucleotides of the invention, which are synthesized by a standard solid phase, automated nucleic acid synthesizer such as the Applied Biosystems, Incorporated 380B or MilliGen/Biosearch 7500 or 8800. Triester, phosphoramidite, or hydrogen phosphonate coupling chemistries (see, e.g., M. Caruthers, *Oligonucleotides. Antisense Inhibitors of Gene Expression.*, pp. 7–24, J. S. Cohen, ed., CRC Press, Inc. Boca Raton, Fla., 1989) are used with these synthesizers to provide the desired oligonucleotides. The Beaucage reagent (see, e.g., *J. Am. Chem. Soc.* 1990, 112, 1253) or elemental sulfur (see, e.g., *Tetrahedron Letters* 1981, 22, 1859), is used with phosphoramidite or hydrogen phosphonate chemistries to provide substituted phosphorothioate oligonucleotides.

Fugitive masking groups are used in preparing certain of the compounds of the invention. Such masking groups allow for ease of synthesis of the compounds. The masking groups are subsequently converted to the desired functionality. Such conversion preferably occurs during a standard deblocking step for a later reaction. An example of this procedure is the use of a phthalimide group for the introduction of an amino functionality. Alkyl phthalimides are attached at the proper position in a compound of interest (e.g., a nucleoside) via a suitable intermediate such as an N-(haloalkyl)phthalimide. The derivatized compound is then used in standard oligonucleotide synthetic techniques on a nucleotide synthesizer. After the desired oligonucleotide is prepared, it is cleaved from the synthesizer support using a suitable reagent. The cleaving reagent also converts the alkylphthalimide to the desired alkylamine. Procedures of this type can be expanded to attach longer chain polyamino functionalities to the oligonucleotides of the invention. Nucleotides or oligonucleotides having a first alkylamino functionality are treated with a further N-(haloalkyl) phthalimide. The extended functionality then is treated to yield a terminal amine group. This can be repeated to further extend the polyamino functionality. Alternately, the extended polyamino functionality first is synthesized and reacted with the first alkylamino functionality to form the polyamino functionality.

Figure 1B:
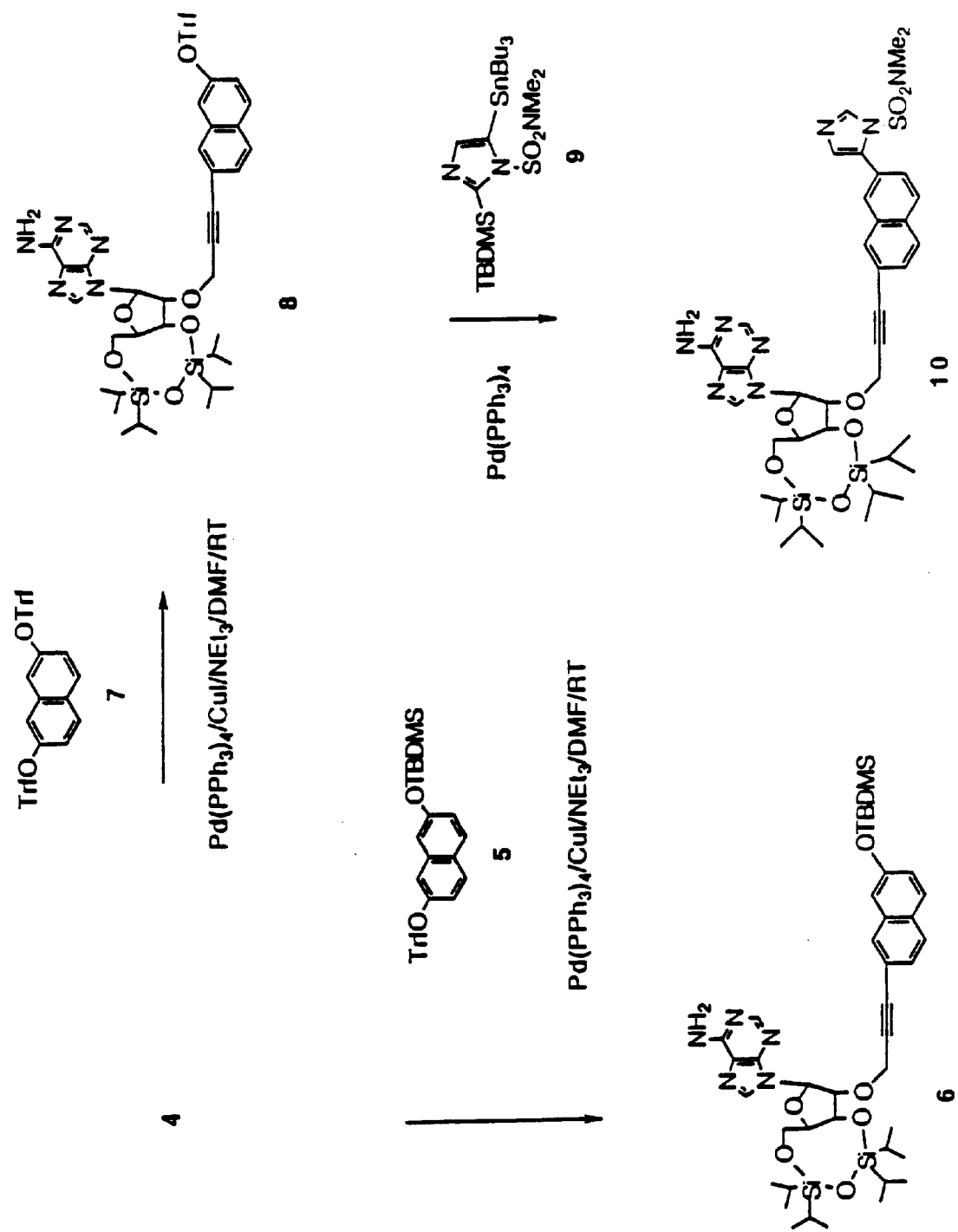
Figure 1C:
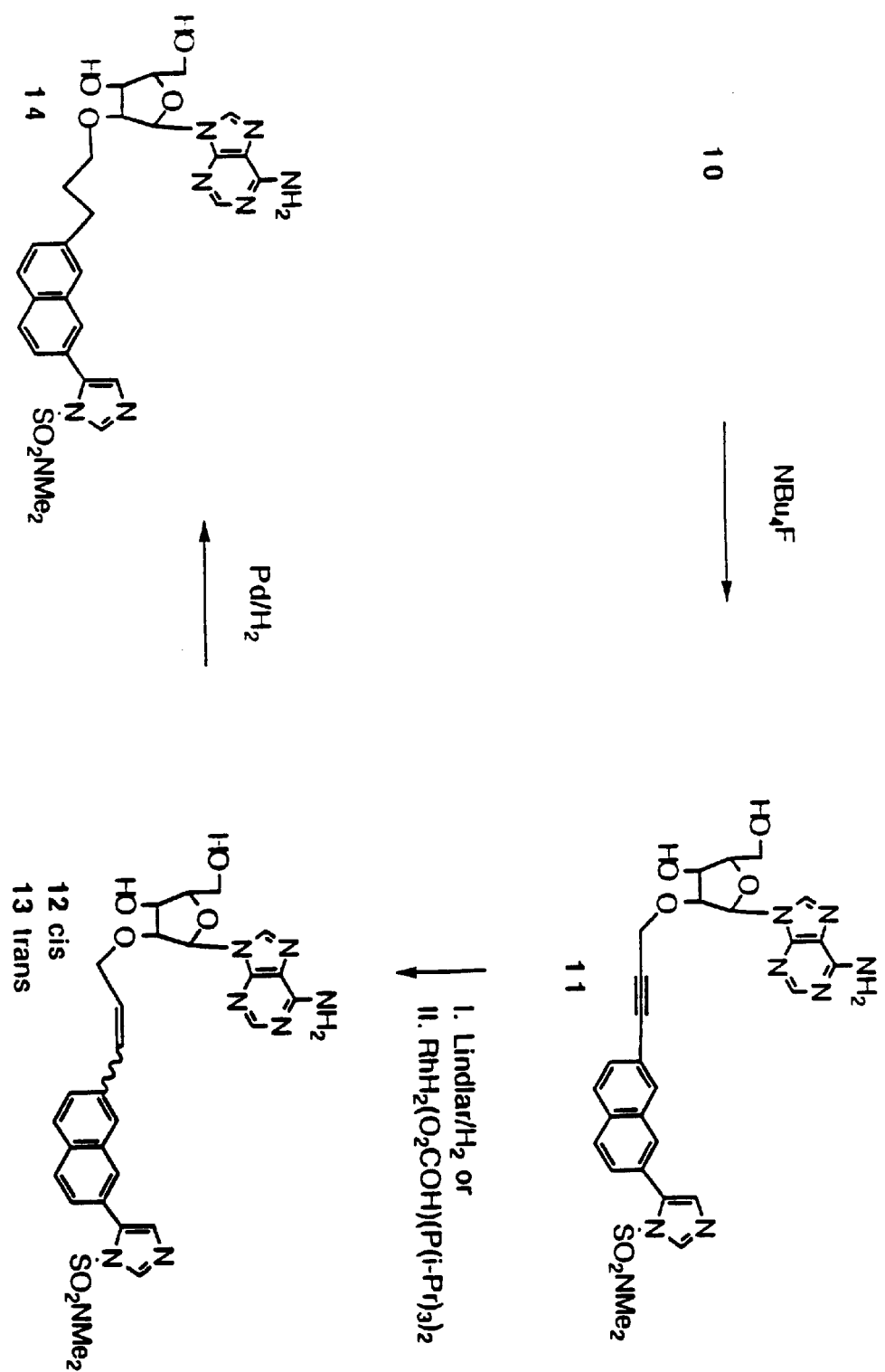

In one representative preparative example, shown in FIG. 1, adenosine was alkylated with propargyl bromide to give a mixture of the 2'- and 3'-regioisomers, 2 and 3, respectively. This mixture was not resolved but was treated with 1,3-dichlorotetraisopropyl disiloxane to afford the tetraisopropyl disiloxane (TPDS) derivatives. Purification at this stage yielded the novel 2'-propargyl protected nucleoside 4 in 54% yield from adenosine. Deprotection of 4 with nBu$_4$NH$_4$F provided the novel 2'-propargyl nucleoside of adenosine 2 in 90% yield. The TPDS-protected form of 3'-regioisomer 3 also can be separated from 4 and deprotected with nBu$_4$NH$_4$F to provide the novel nucleoside 3. A palladium catalyzed cross-coupling reaction of alkyne 4 and naphthyl triflate 5 furnished coupled nucleoside product 6 in 83% yield. Coupling of alkyne 4 and naphthyl ditriflate 7 provided the naphthyltriflate coupled nucleoside product 8 in 86% yield. Compound 8 was reacted by a Stille-type palladium-catalyzed coupling with imidazole organostannane 9 to afford the imidazoylnaphthyl coupled nucleoside 10 in 48% yield. Treatment of 10 with nBu$_4$NH$_4$F to provide unprotected imidazoylnaphthyl nucleoside 11, followed by selective hydrogenation with Lindlar catalyst, gives cis olefin derivative 12. The trans olefin 13 can also be afforded via selective hydrogenation of 11 with dihydrido (bicarbonato)bis-(triisopropylphosphine)rhodium (III). Further hydrogenation of 11, 12 or 13 with palladium will provide alkyl-tethered imidazoylnaphthyl nucleoside 14.

Figure 2A:
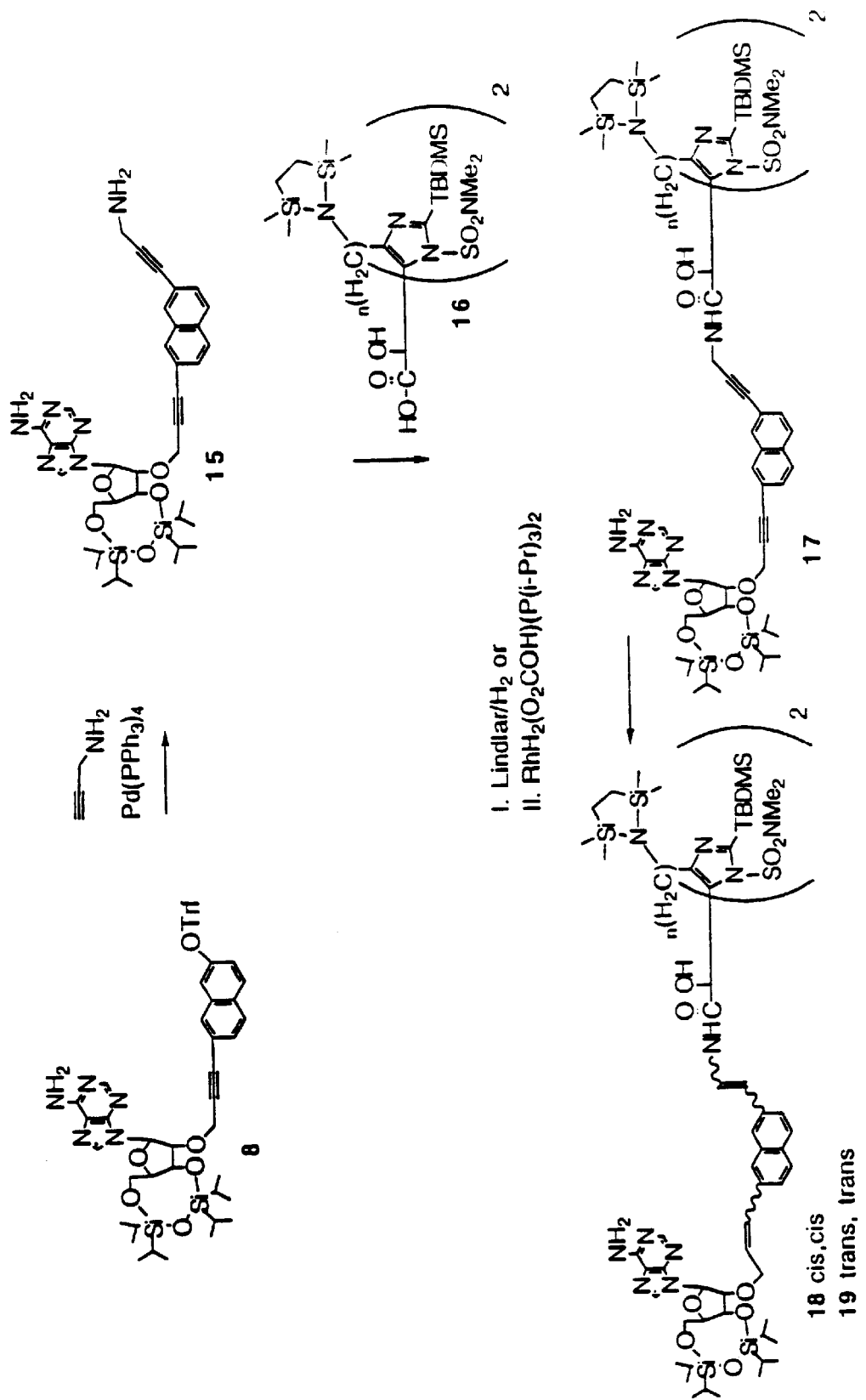
FIG. 2 provides a general synthetic scheme for compound 20.
Figure 2B:
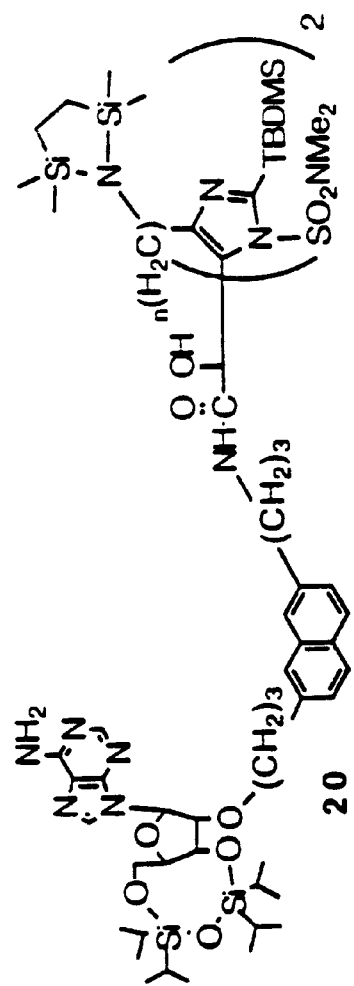
Figure 2B:

As shown in FIG. 2, the aminopropynyl naphthyl-tethered nucleoside 15 is prepared by effecting a palladium catalyzed coupling of 8 with propargylamine and a carbodiimide mediated condensation of 15 with the protected bis-aminopropyl imidazoyl glycolic acid 16. This affords bis-imidazoyl functionalized nucleoside 17. Stereoselective reduction of 17 as described for 10 will provide cis, cis- and trans, trans-derivatives, 18 and 19, respectively. Further reduction of 17, 18, or 19 will afford alkyl-tethered bis-imidazolyl-functionalized nucleoside 20.

Figure 3:
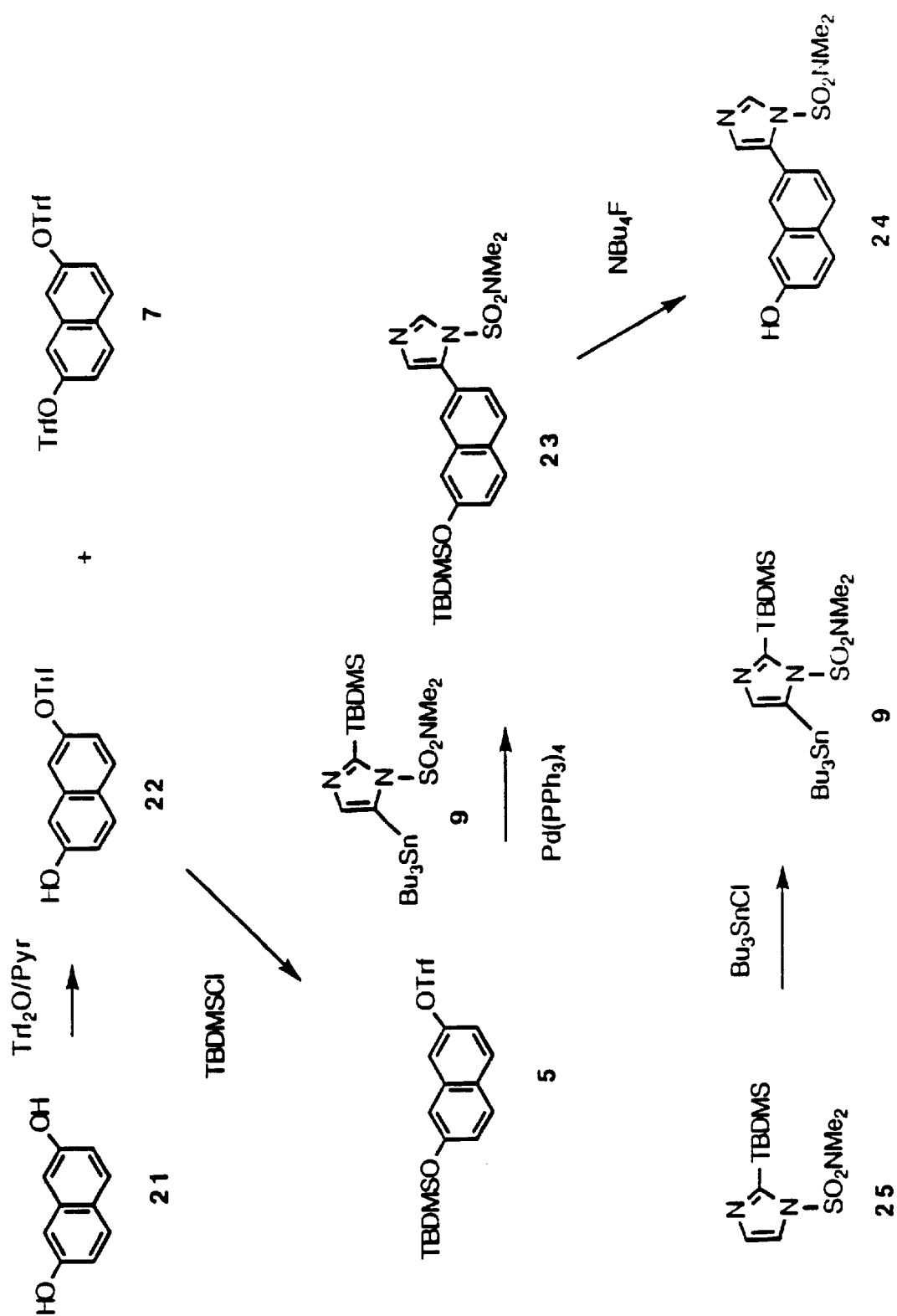
FIG. 3 provides general synthetic schemes for compounds 9 and 24.

The novel compound 7-hydroxy-2-O-triflyl naphthalene 22 was synthesized, as in FIG. 3, in 34% yield by treatment of the naphthalenediol 21 with trifluoromethanesulfonic anhydride. The 2,7-di-O-triflyl naphthalene 7 was afforded concomitantly in 26% yield. Compound 22 was protected with t-butyldimethysilyl to provide 5 in 73% yield. Palladium catalyzed coupling of 5 and organostannylimidazole 9 provided novel protected imidazoylnaphthalene derivative 23 in 38% yield. Deprotection of the t-butyldimethysilyl group gave the novel imidazoylnaphthalene compound 24 in 76% yield. The protected novel organostannylimidazole 9 was prepared by treatment of the reported protected imidazole 25 with tri-n-butyltin chloride to furnish 9 in 52% yield.

Figure 4A:
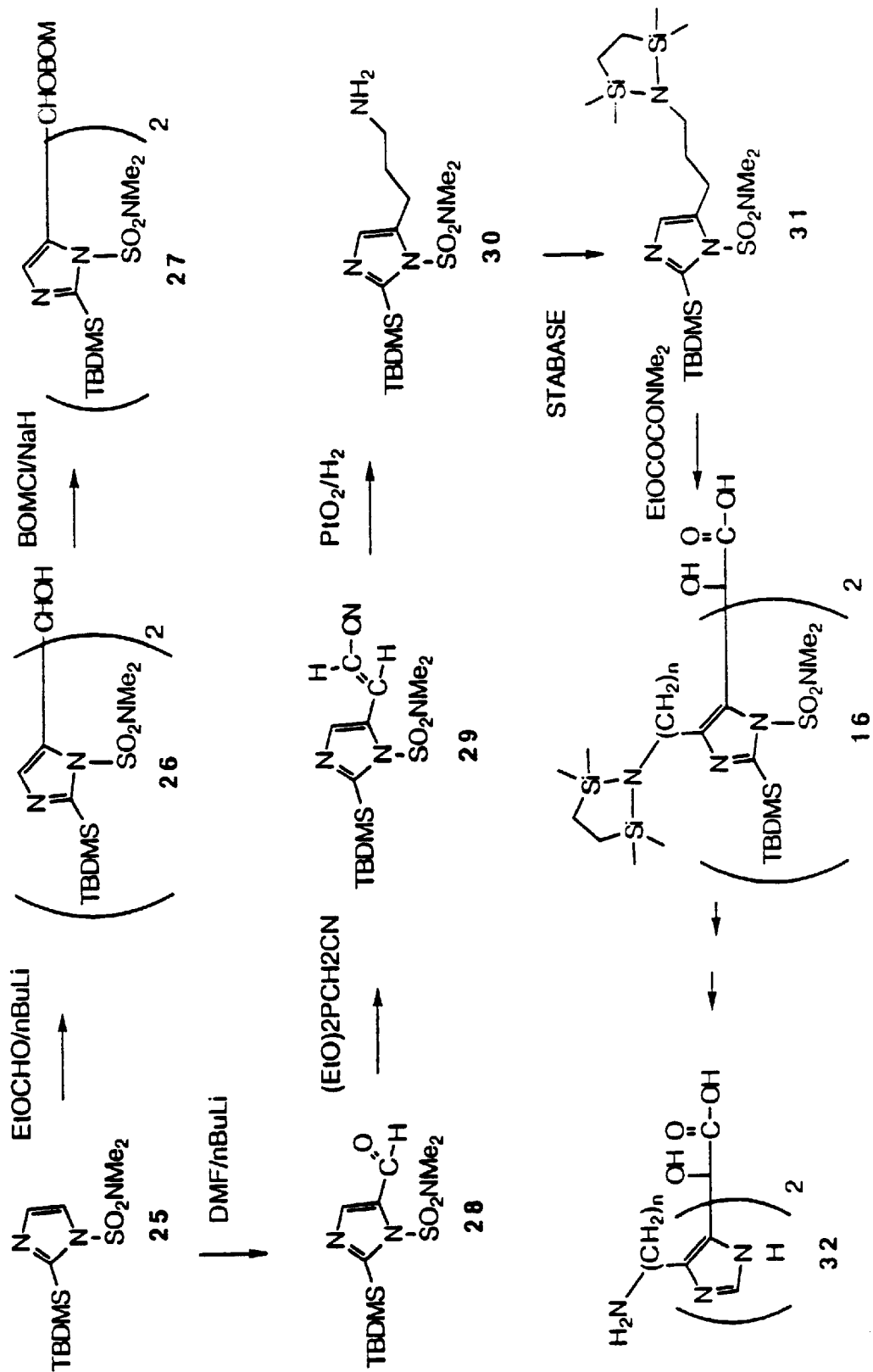
FIG. 4 provides a general synthetic scheme for compound 34.
Figure 4B:
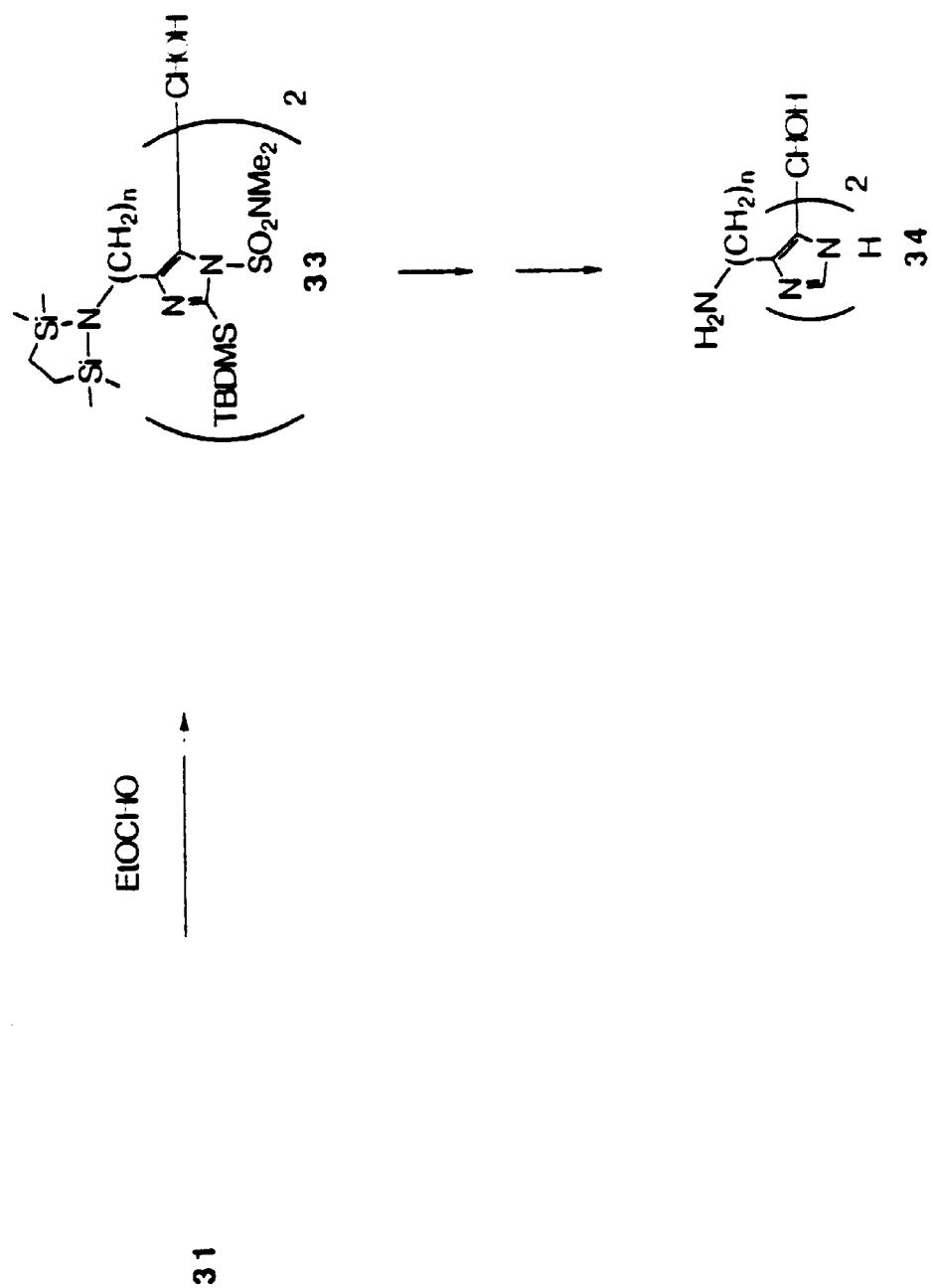

As shown in FIG. 4, protected bis-imidazoyl carbinol 26 was synthesized in 69% yield according to the literature procedure of Tang, et al., *J. Am. Chem. Soc.* 1978, 3918, by reaction of 25 with ethyl formate. Protection of the hydroxyl function was effected with benzylchloromethyl ether to afford 27 in 80% yield. The protected bis-aminopropyl imidazoyl glycolic acid 16 is synthesized by reaction of 25 with DMF and butyl lithium to provide 2-aldehydo derivative 28, which is treated with cyanomethyl diethylphosphonate to afford the modified Wittig product 29. Hydrogenation of 29 with $PtO_2$ furnishes the aminopropyl imidazole 30, which is protected with STABASE (1,1,4,4-tetramethyl-1,4-dichlorosilethylene) to give the amino-protected imidazole 31. Reaction of 31 with ethyl N,N-dimethyl oxamate provides the protected bis-aminopropyl imidazoyl glycolic acid 16, which is deprotected to give the bis-aminopropyl imidazoyl glycolic acid 32. The bis-aminopropyl imidazoyl carbinol 34 is afforded by treatment of 31 with ethylformate to give 33. Deprotection provides bis-aminopropylimidazoyl carbinol 34.

Figure 5A:
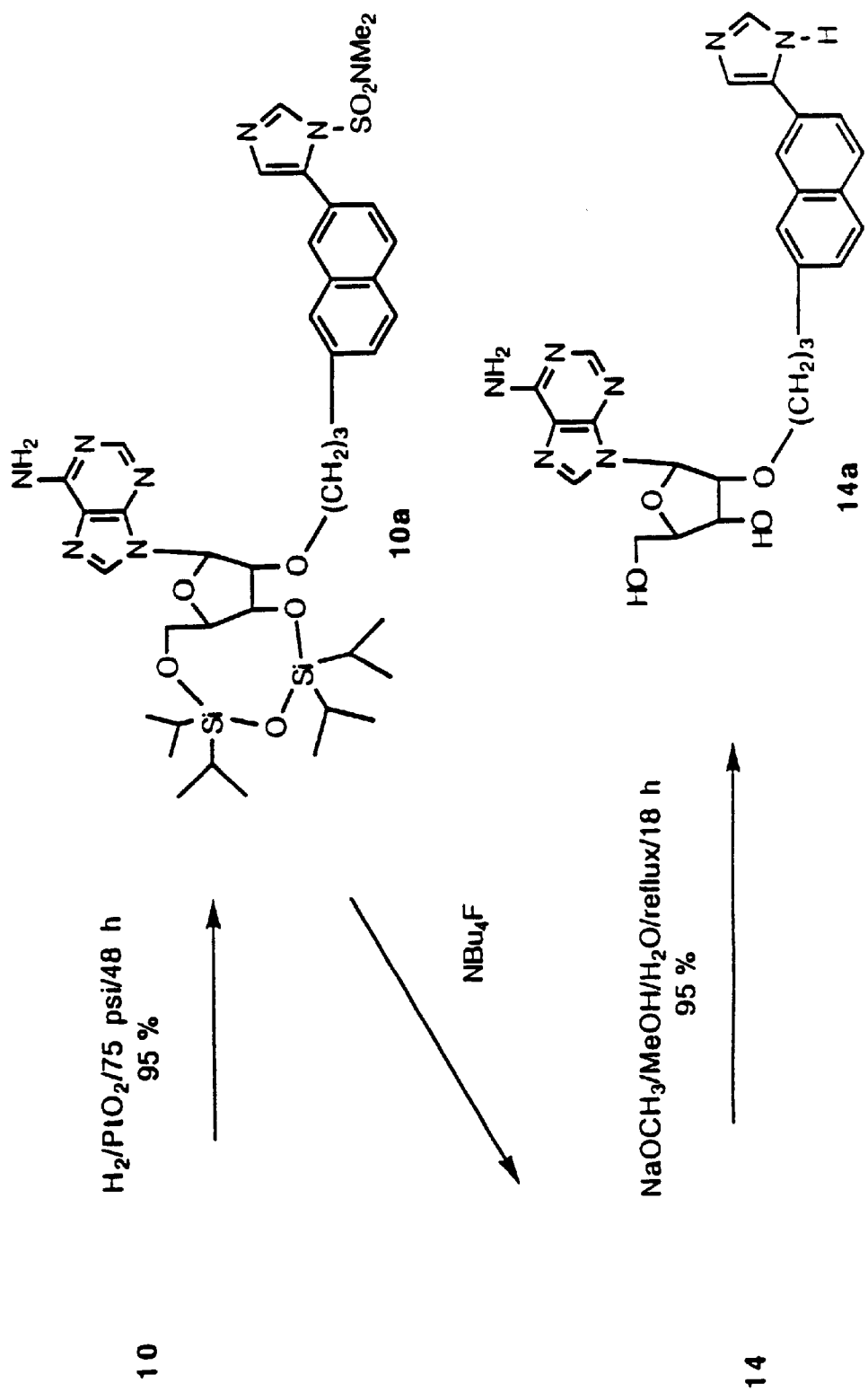
FIG. 5 provides an alternate synthetic scheme for compound 14.
Figure 5B:
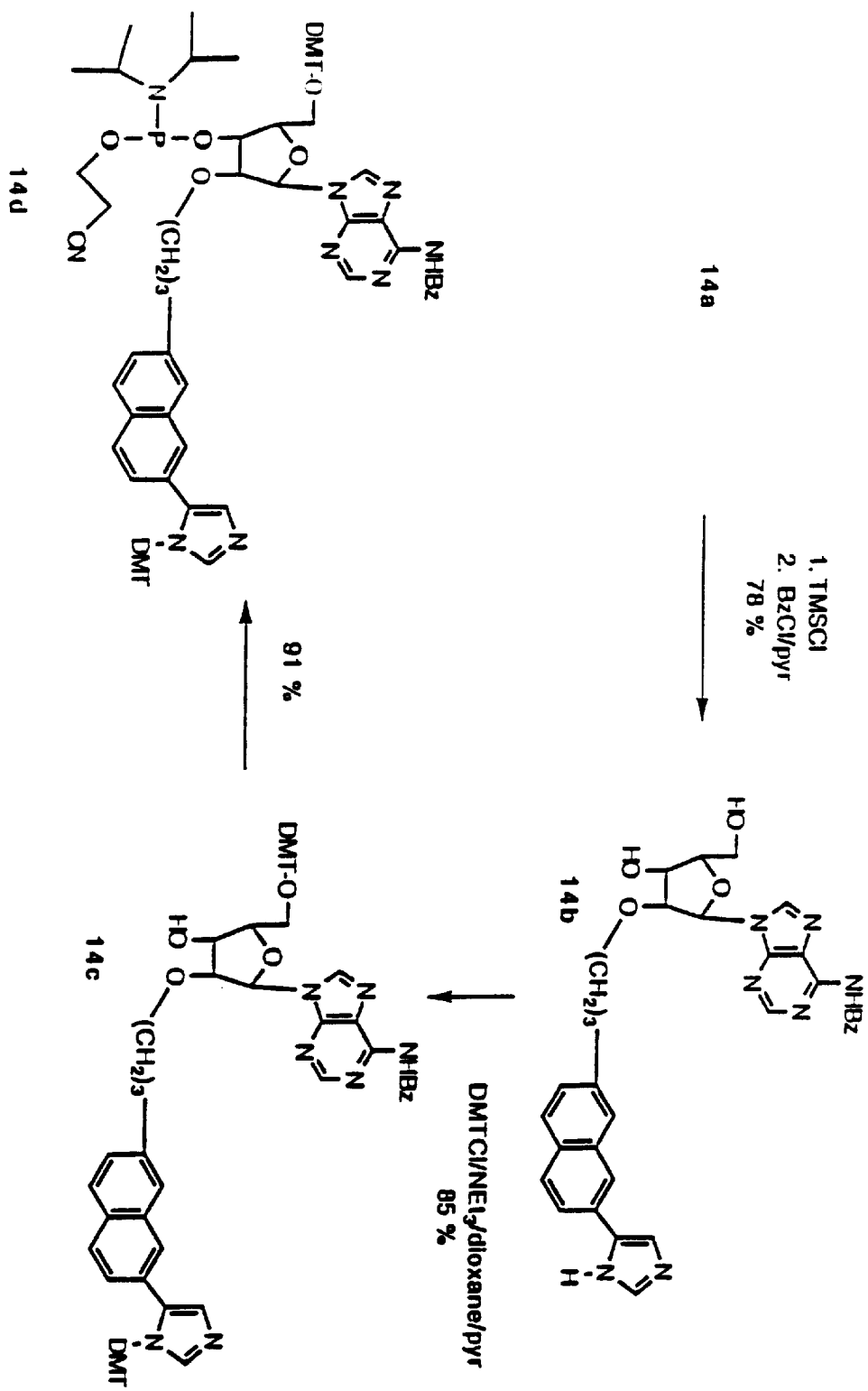
Figure 6A:
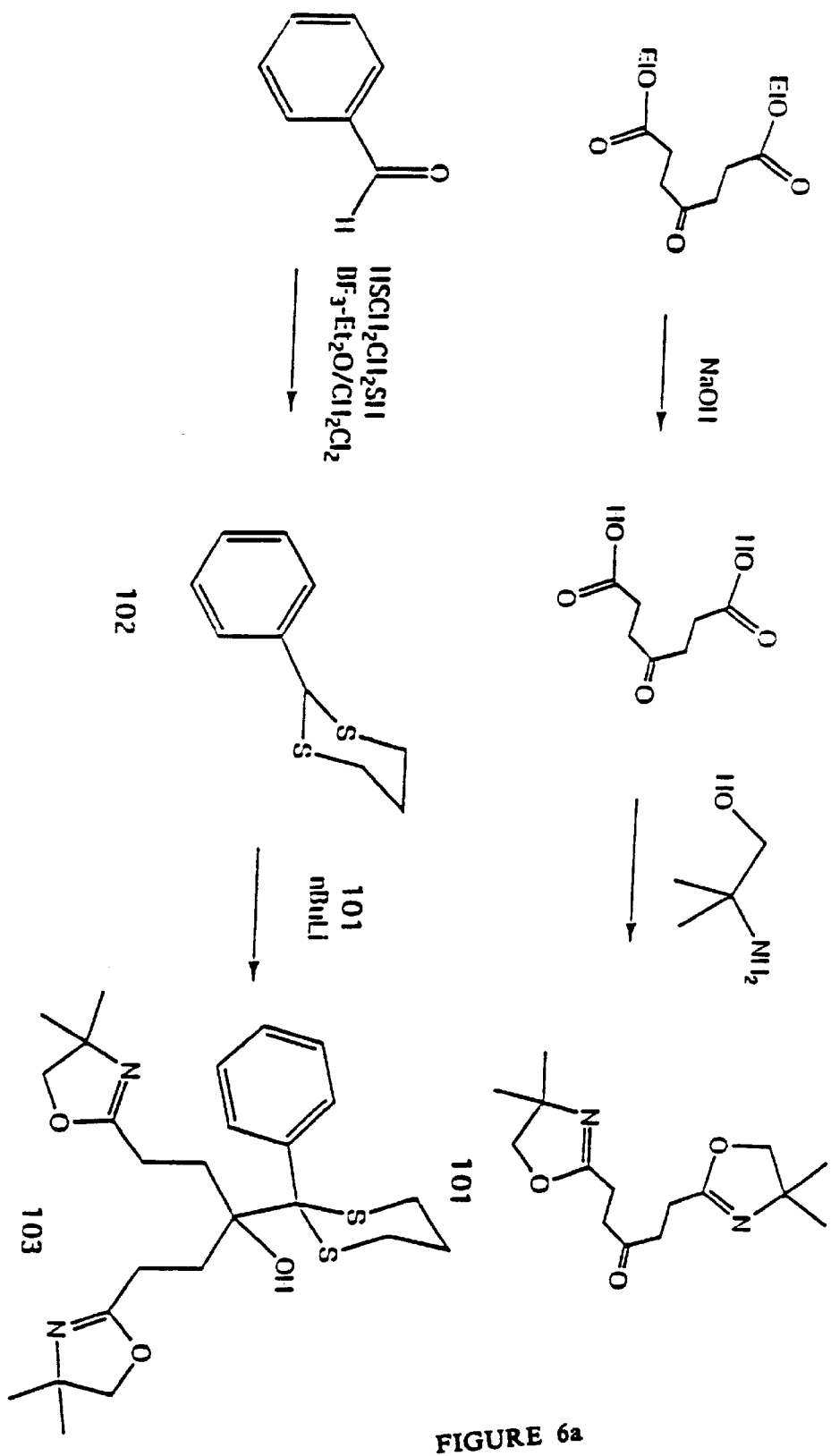
FIGS. 6 to 12 provide general synthetic schemes for compounds 134, 135 and 137.
Figure 6B:
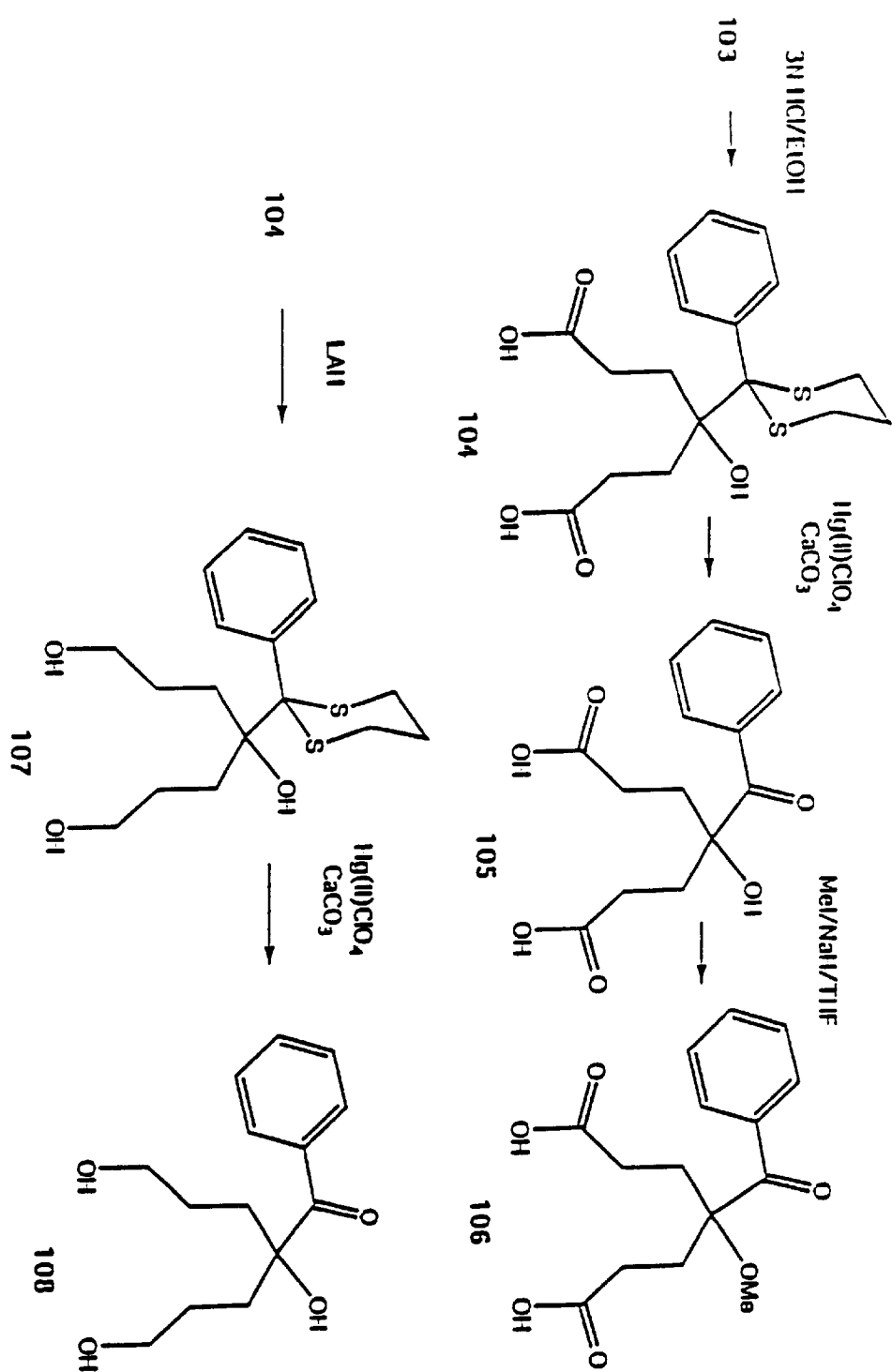
Figure 7A:
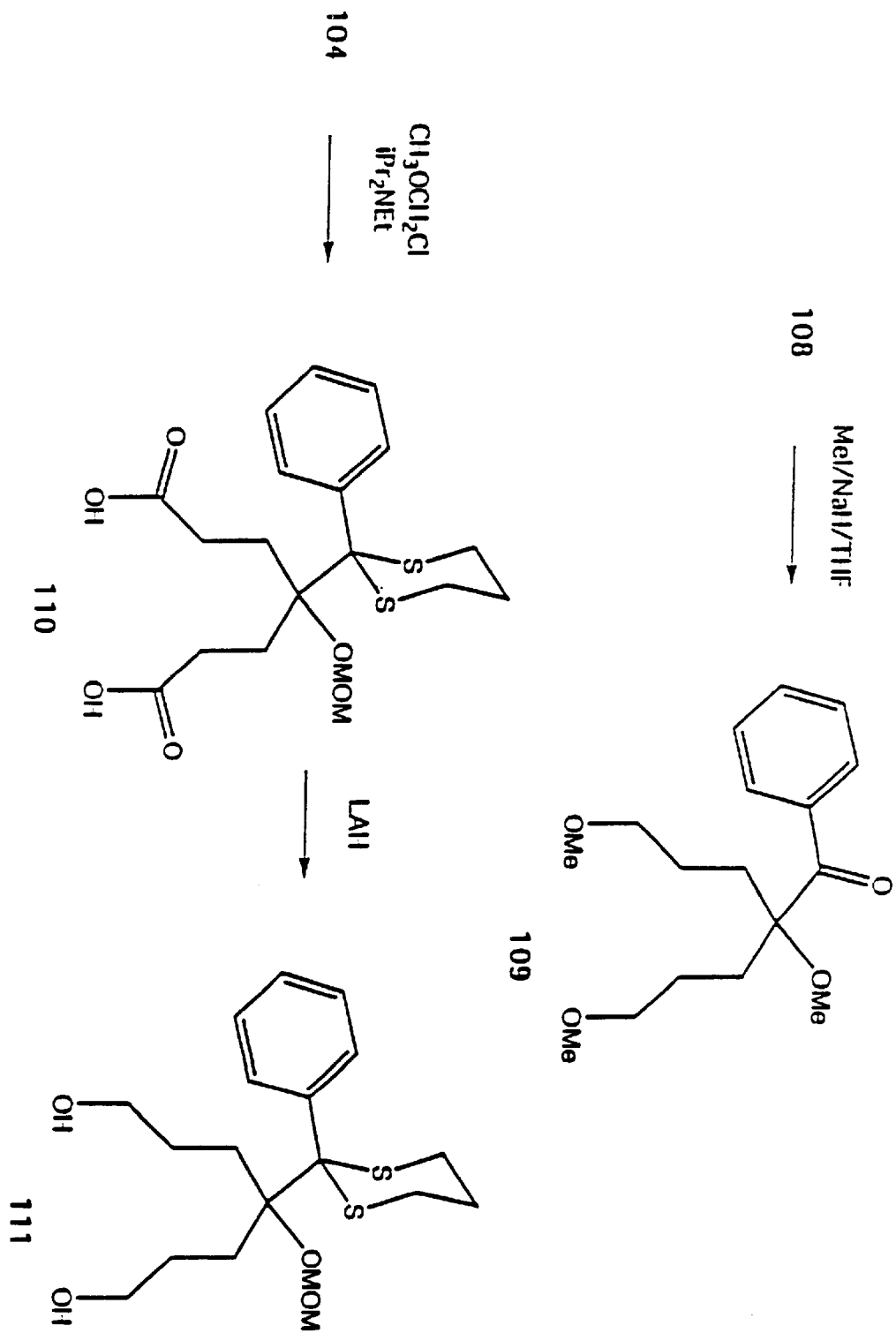
Figure 7B:
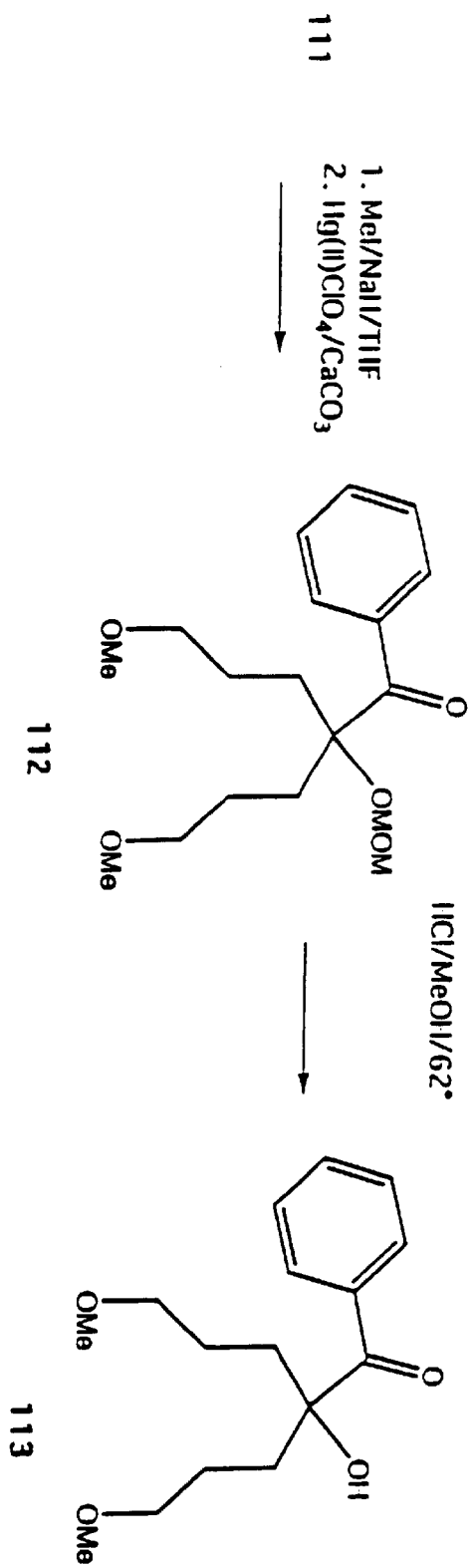
Figure 8A:
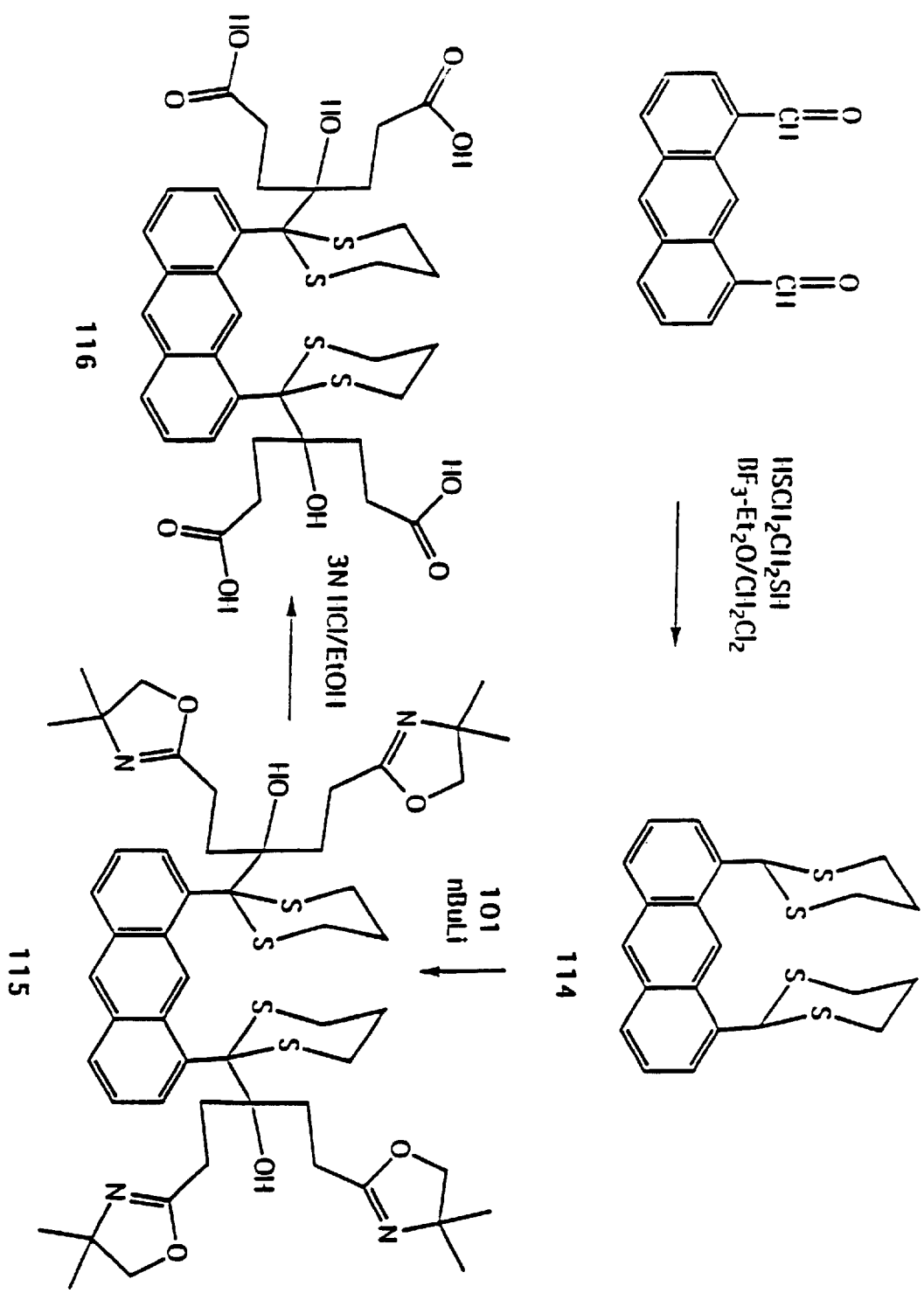
Figure 8B:
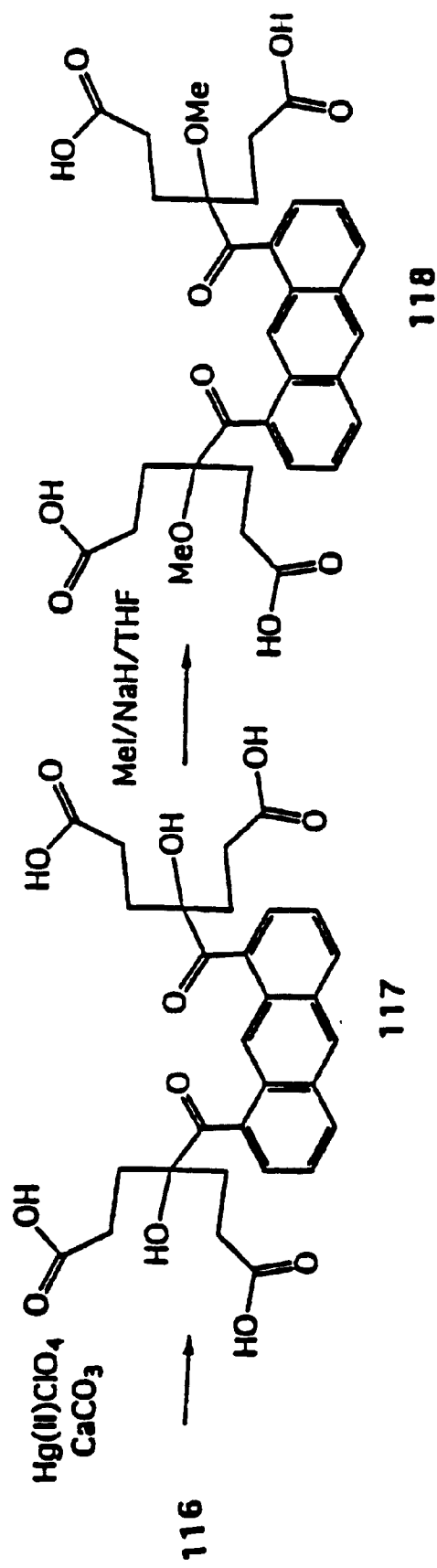
Figure 9A:
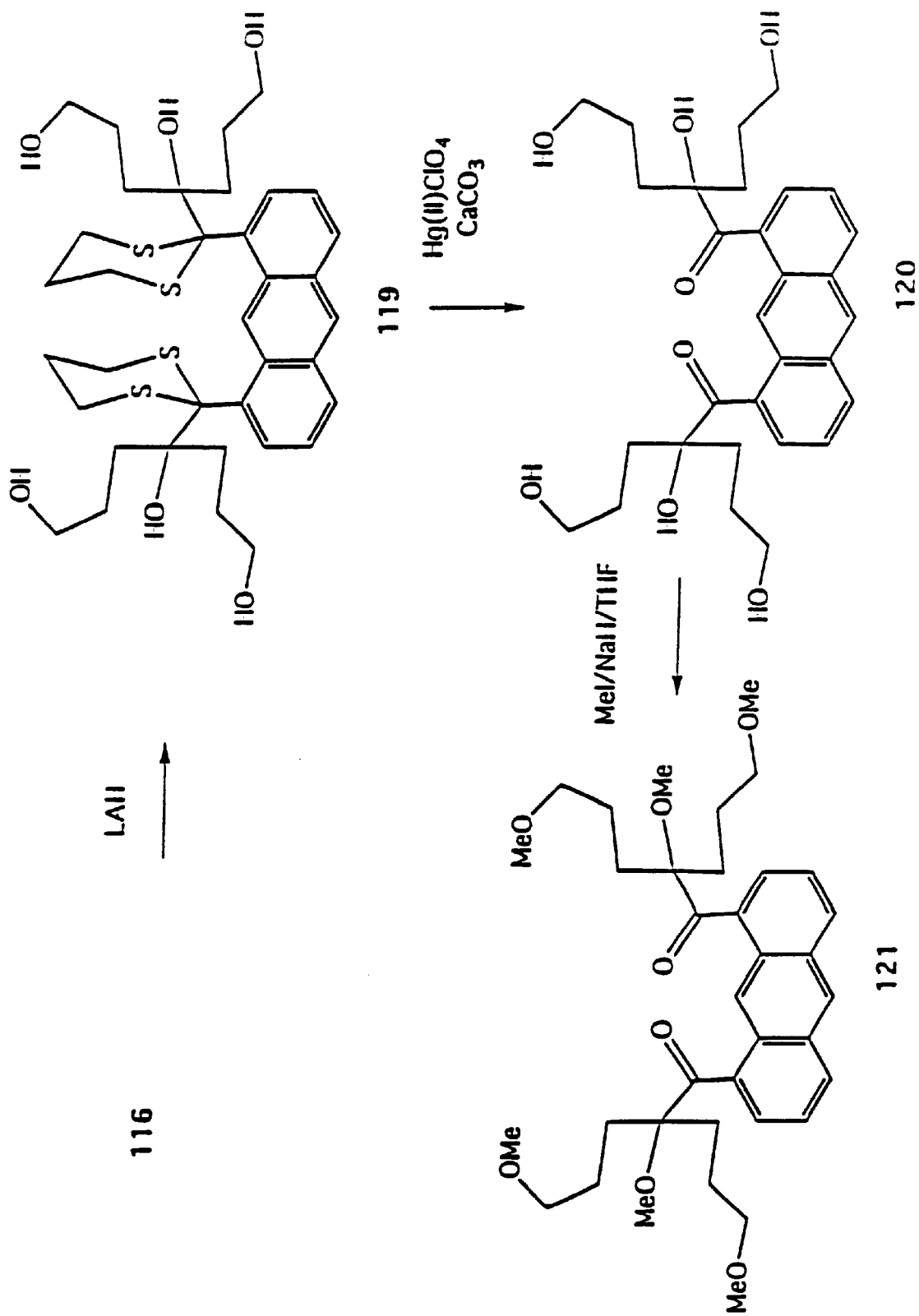
Figure 9B:
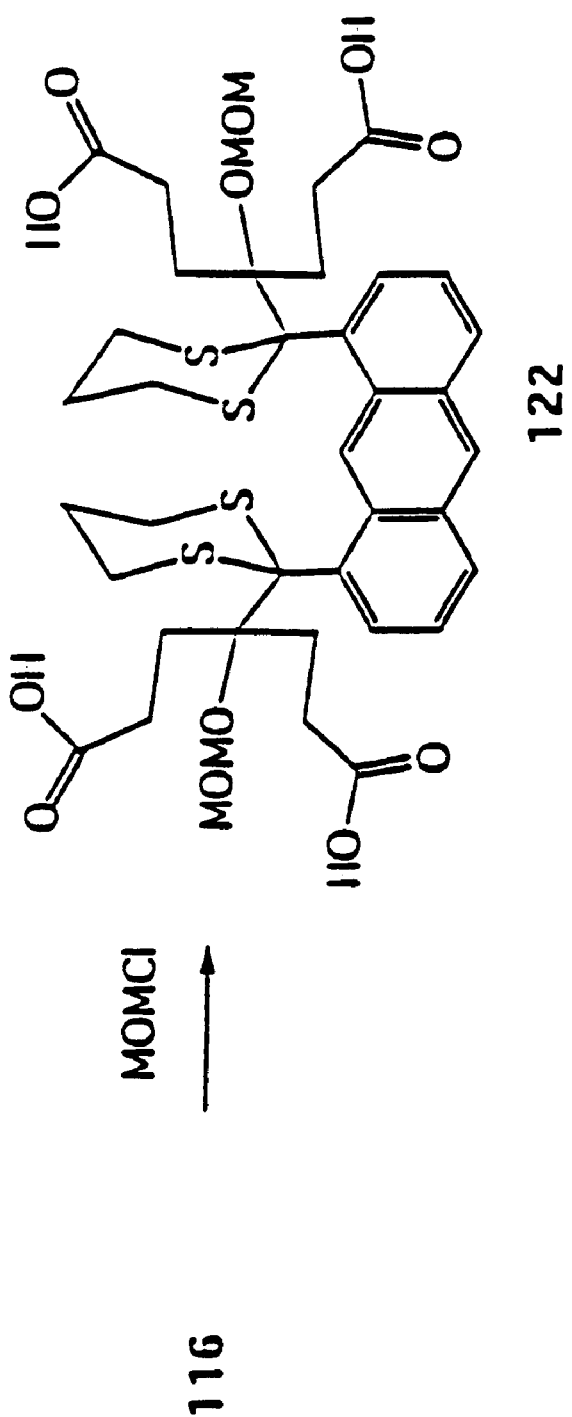
Figure 10:
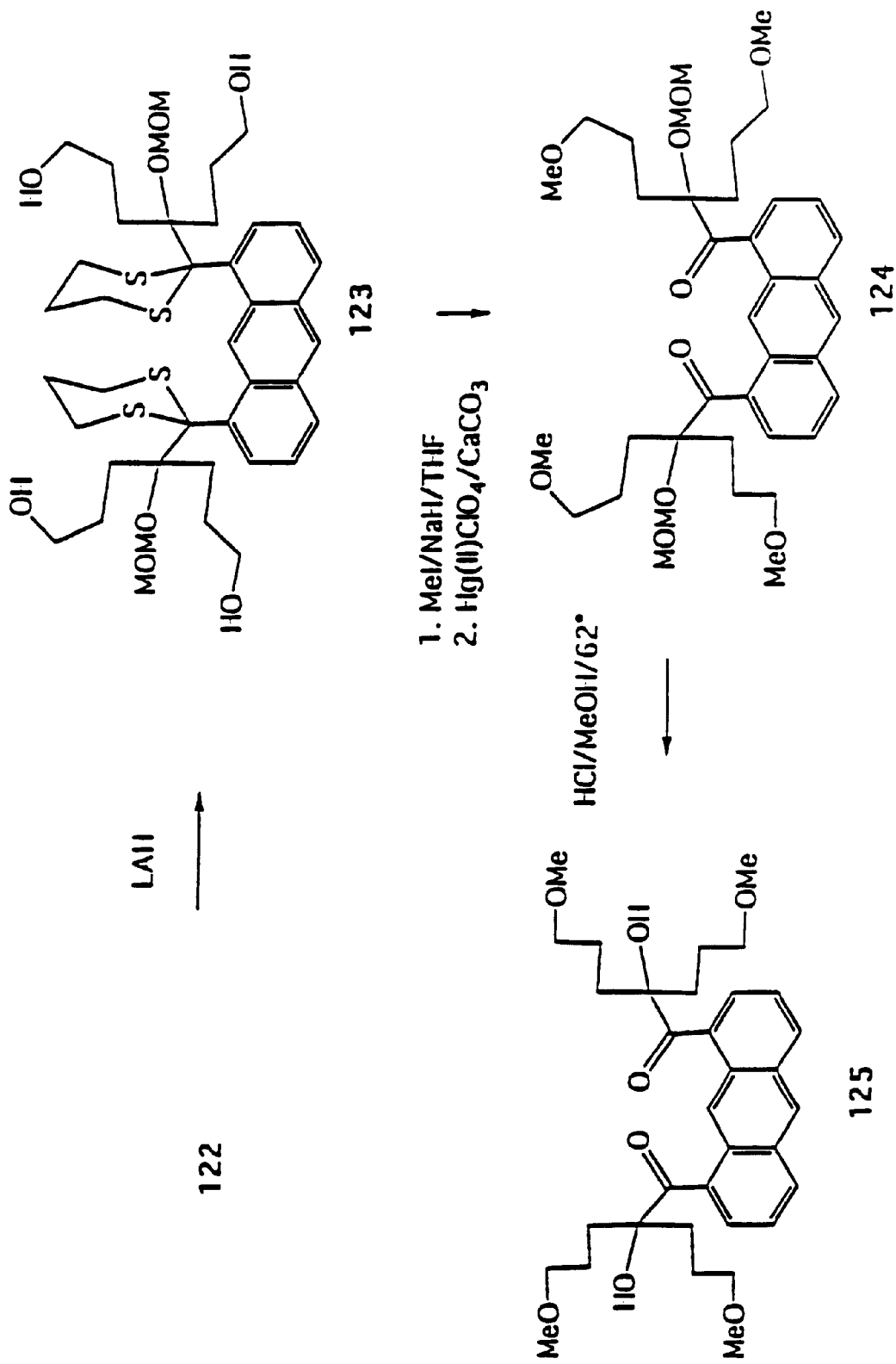
Figure 11A:
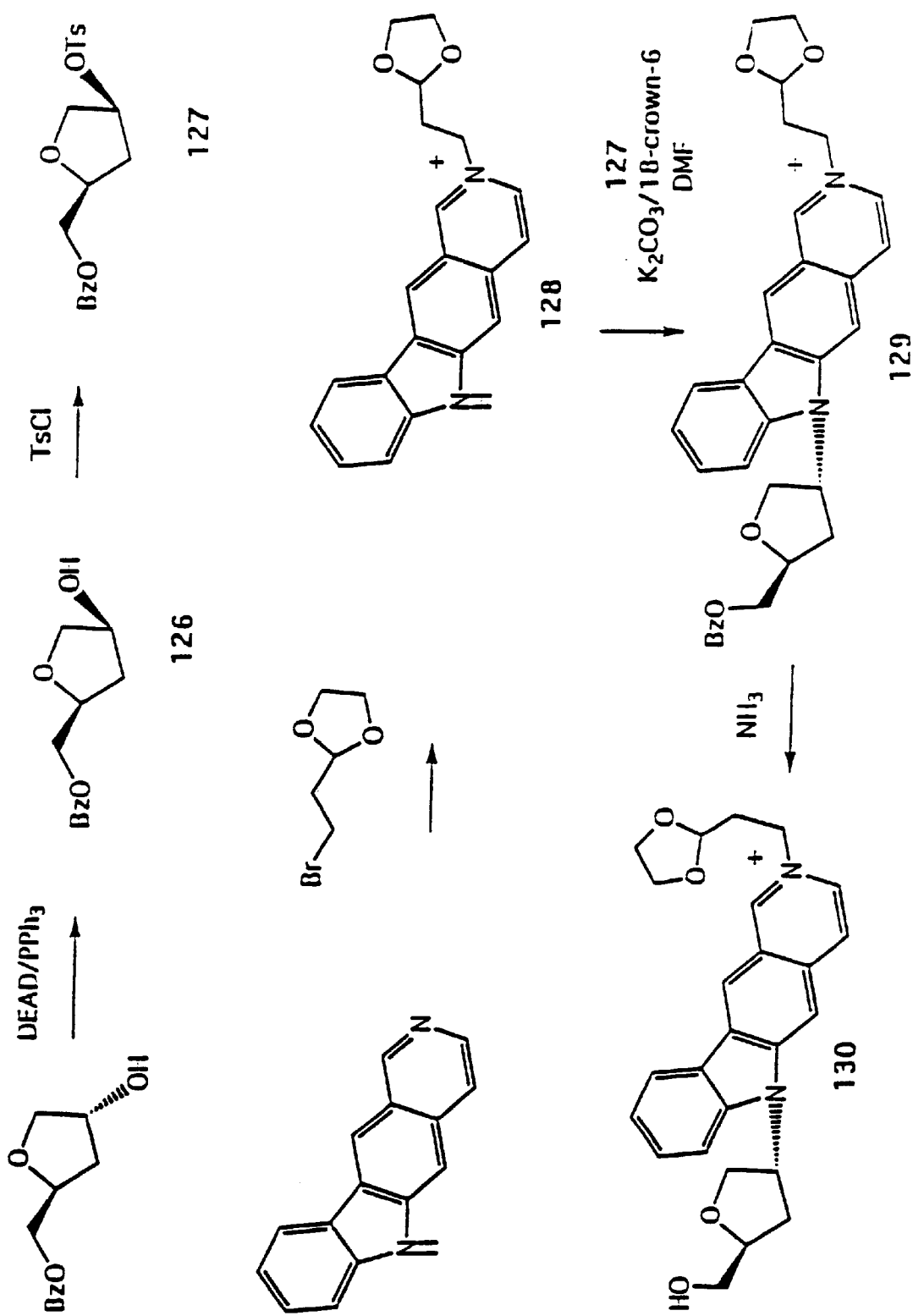
Figure 11B:
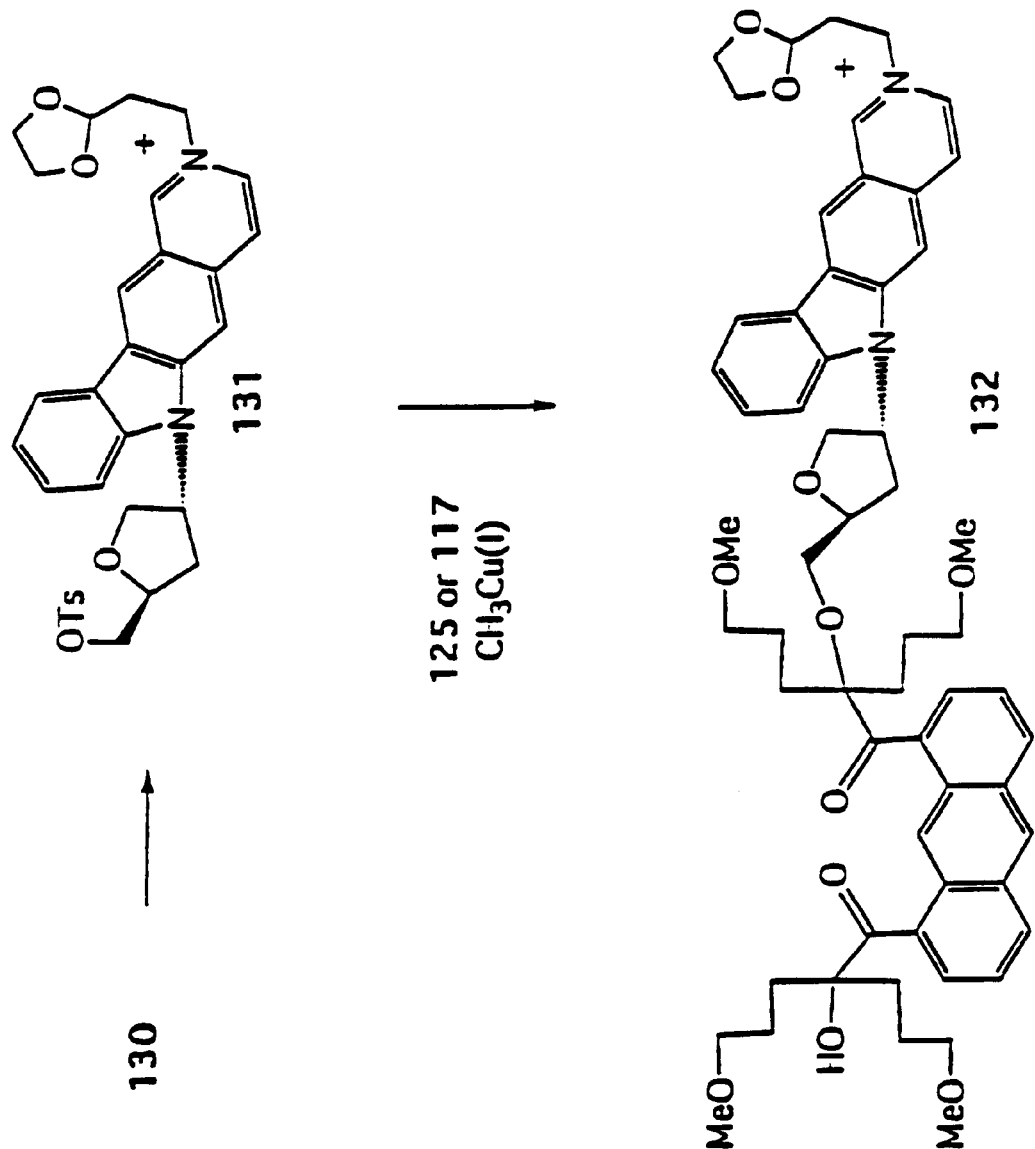
Figure 12A:
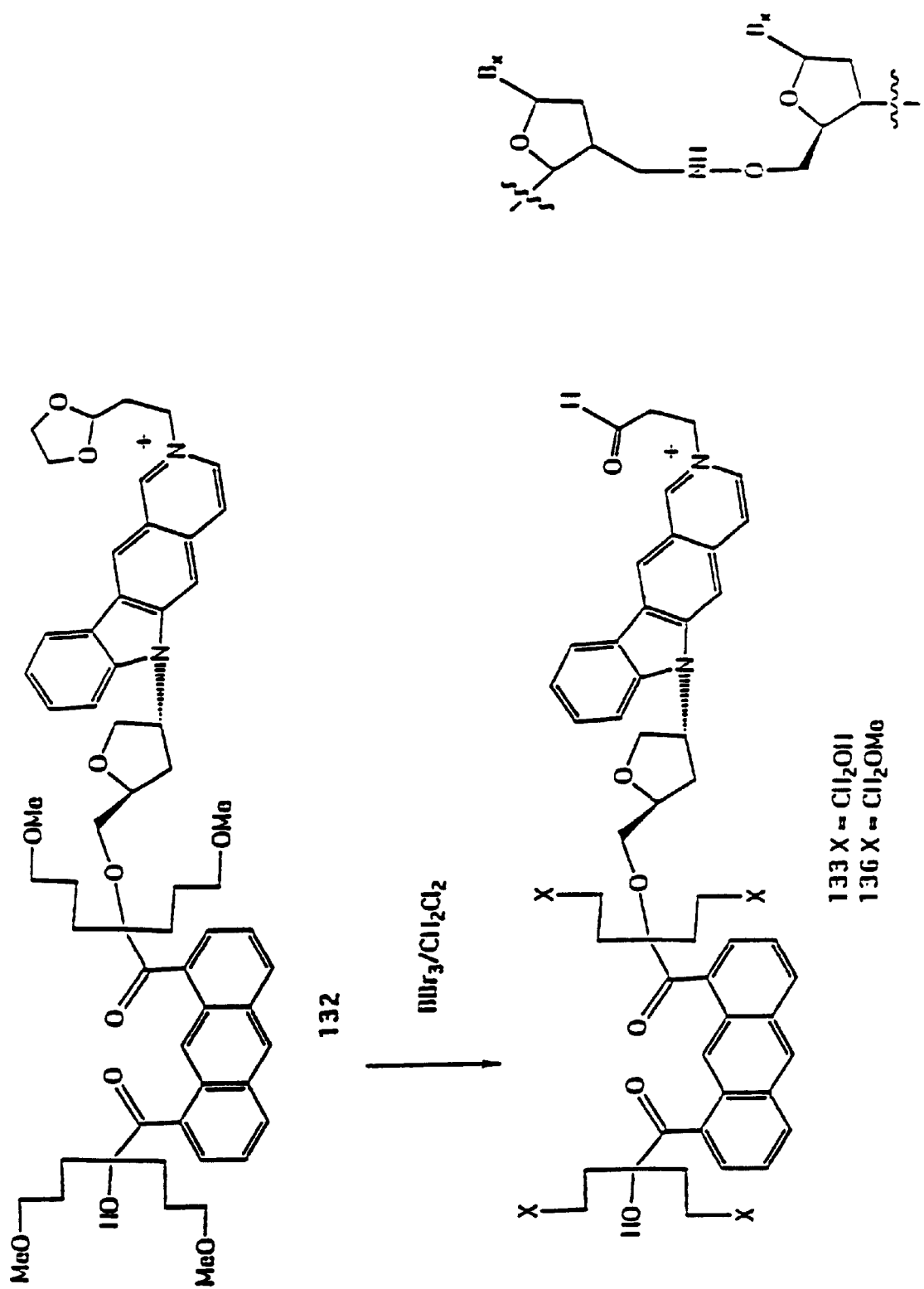
Figure 12B:
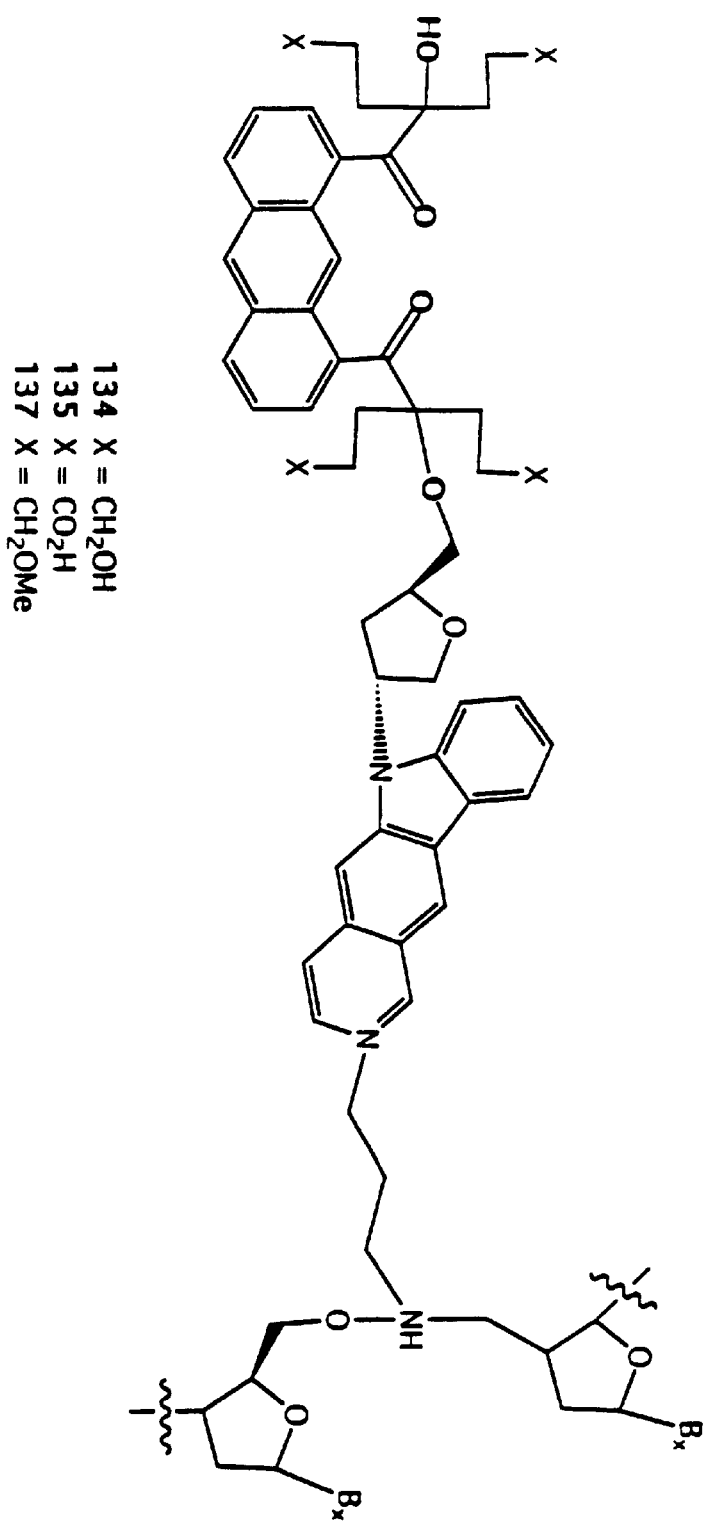

FIG. 5 shows an alternate synthesis of compound 14.

FIGS. 6 through 12 illustrate the synthesis of a further series of compounds of the invention. These include synthetic steps to prepare cleaver moieties that will coordinate with one metal ions as is illustrated by compounds 106, 109 and 113. These Figures also include the synthetic steps to prepare cleaver moieties that will coordinate with two metal ions as is illustrated by compounds 134, 135 and 137.

NMR spectra were obtained with the following instruments: $^1$H-NMR: Varian Gemini-200 (199.975 MHz), $^{13}$C-NMR: Varian Gemini-200 (50.289 MHz). NMR spectra were recorded using either deuteriochloroform (tetramethylsilane as internal standard) or dimethylsulfoxide-$d_6$ as solvent. The following abbreviations were used to designate the multiplicity of individual signals: s=singlet, d=doublet, t=triplet, q=quartet, ABq=ab quartet, m=multiplet, dd=doublet of doublets, br s=broad singlet. Mass spectra were acquired on a VG 70-SEQ instrument (VG Analytical (Fisons)), using fast atom bombardment ionization (7 kV Xe atoms). Solvent ratios for column chromatography are given as volume/volume. Evaporations of solvents were performed in vacuo (60 torr) at 30° C. unless otherwise specified.

EXAMPLE 1

9-(2-(O-2-propynyloxy)-β-D-ribofuranosyl)adenine, 2

Compound 4 was dissolved in THF (10 mL) under an argon atmosphere and 1M tetra-n-butylammonium fluoride (3.6 mL, 3.6 mmol) was added to the reaction mixture to give a turbid solution. After stirring the reaction for 3 hours, the solvent was evaporated in vacuo to give an oil which was purified by column chromatography using EtOAc-MeOH, 80:20, as eluent. Title compound 2 was isolated as a white solid (503 mg, 90%) which was crystallized from methanol at reflux temperature to give white crystals. mp 147–148° C. $^1$H-NMR (200 MHz, $Me_2SO$-$d_6$): 8.36 (s, 1, H8), 8.13 (s, 1, H2), 7.36 (br s, 2, NH), 6.00 (d, 1, H1', $J_{1',2'}$=6.2 Hz), 5.48 (m, 1, 5'OH), 5.35 (d, 1, 3'OH), 4.68 (m, 1, H2'), 4.32 (m, 1, H3'), 4.21 (ABq, 2, $OCH_2CC$, J=15.7 Hz), 3.98 (m, 1, H4'), 3.58 (m, 2, H5'a, H5'b), 3.27 (s, 1, CCH). FTIR (KBr): 2114 $cm^{-1}$ (w, CCH). Anal. Calcd. for $C_{13}H_{15}N_5O_4$: C, 51.14, N, 4.95, N, 22.94. Found: C, 50.98; H, 4.86; N, 22.81.

EXAMPLE 2

9-(2-(O-2-propynyloxy)-3,5-O-tetraisopropyldisiloxanyl-β-D-ribofuranosyl) adenine, 4

Adenosine (10.7 g, 40.0 mmol) was dissolved in hot anhydrous DMF (200 mL) under an argon atmosphere, the solution was cooled to 5° C., and NaH (1.76 g, 44 mmol) was added as a 60% dispersion in oil. The reaction mixture was stirred at ambient temperature for 30 min after which time propargyl bromide (4.90 mL, 44 mmol) as an 80% solution in toluene was added via syringe. After the reaction mixture was stirred for 24 hours the solvent was evaporated in vacuo (1 torr) at 40° C. to give a gum. This crude mixture was dried in vacuo (1 torr) at ambient temperature for 18 hours, evaporated with anhydrous pyridine twice, then partially dissolved in hot anhydrous pyridine (120 mL). 1,3-Dichlorotetraisopropyl disiloxane (14.35 mL, 45.6 mmol) was added and the reaction mixture was stirred at ambient temperature for 4 hours and the solvent was evaporated in vacuo (1 torr) at 40° C. to give a residue which was suspended in EtOAc (200 mL). The organic phase was washed with brine, separated and dried with $MgSO_4$. Evaporation of the solvent in vacuo gave an oil which was purified by column chromatography using hexane-EtOAc, 25:75, as eluent. The title compound was obtained as a white solid (11.8 g, 54%). $^1$H-NMR (200 MHz, $CDCl_3$): d 8.32 (s, 1, H8), 8.08 (s, 1, H2), 6.03 (s, 1, H1'), 5.69 (br s, 2, NH), 4.86 (dd, 1, H3'), 4.59 (ABq, 2, $OCH_2CC$, J=15.5 Hz), 4.53 (d, 1, H2', $J_{2',3'}$=4.70 Hz), 4.18 (m, 1, H4'), 4.12 (m, 2, H5'$_a$, H5'$_b$), 2.41 (t, 1, CCH, J=2.28 Hz), 1.08 (m, 28, $SiCHMe_2$). FTIR (NaCl): 2118 $cm^{-1}$ (w, CCH). Anal. Calcd. for $C_{25}H_{41}N_5O_5Si_2$: C, 54.82, H, 7.55, N, 12.79, Si, 10.22. Found: C, 54.94; H, 7.63; N, 12.67; Si, 10.13.

EXAMPLE 3

2-(7-t-Butyldimethylsilyloxy)naphthyl trifluoromethane-sulfonate, 5

Compound 22 (8.00 g, 27.4 mmol) was dissolved in anhydrous pyridine (120 mL) under an argon atmosphere and t-butyldimethylchlorosilane (5.37 g, 35.6 mmol) was added. The reaction mixture was stirred at ambient temperature for 24 hours, poured into water (120 mL), and extracted with ether (3×120 mL). The organic phase was separated and washed with water (120 mL), aqueous 10% HCl (120 mL), water (120 mL), and brine (120 mL). After separation, the organic phase was dried with MgSO$_4$ and the solvent was evaporated in vacuo to give an oil, which was purified by column chromatography using hexane-EtOAc, 90:10, as eluent. The title compound was obtained as an oil (8.10 g, 73%). $^1$H-NMR (200 MHz, CDCl$_3$): d 7.86 (m, 6, HAr), 1.02 (s, 9, Me$_3$), 0.26 (s, 6, CH$_3$).

EXAMPLE 4

9-((4-(7-(2-O-t-butyldimethylsilyloxy)naphthyl)-O-2-propynyloxy-)-3,5-O-tetraisopropyldisiloxanyl-β-D-ribofuranosyl))adenine, 6

Compound 4 (1.052 g, 1.92 mmol), compound 5 (780 mg, 1.92 mmol), tetrakis(triphenylphosphine)palladium(0) (222 mg, 0.192 mmol), CuI (73 mg, 0.384 mmol), and NEt$_3$ (0.54 mL, 3.84 mmol) were stirred in anhydrous DMF (10 mL) under an argon atmosphere at ambient temperature. After 3 hours the solvent was evaporated in vacuo (1 torr) at 40° C. to give an oil which was dissolved in EtOAc. The organic phase was washed with water, dried with MgSO$_4$, and the solvent was evaporated in vacuo to give a foam. The product was purified by column chromatography using hexane-EtOAc, 50:50, to give the title compound 6 as a foam (1.26 g, 83%). $^1$H-NMR (200 MHz, CDCl$_3$): d 8.28 (s, 1, H8), 8.10 (s, 1, H2), 7.72–7.04 (m, 6, HAr), 6.11 (s, 1, H1'), 5.60 (br s, 2, N H), 4.85 (ABq, 2, OCH$_2$CC, J=15.8 Hz), 4.83 (m, 1, H3'), 4.68 (d, 1, H2'), 4.21 (m, 1, H4'), 4.13 (m, 2, H5'a, H5'b), 1.06 (m, 28, SiCHMe$_2$), 1.01 (s, 9, (CH$_3$)$_3$), 0.24 (s, 6, CH$_3$—Si). FTIR (NaCl): 2253 cm$^{-1}$ (w, CCH). Anal. Calcd. for C$_{41}$H$_{61}$N$_5$O$_6$Si$_3$: C, 61.23, H, 7.64, N, 8.71. Found: C, 61.04; H, 7.78; N, 8.26.

EXAMPLE 5

2,7-Di-O-trifluoromethanesulfonyl naphthalene (7) and 2-(7-hydroxy)naphthyl trifluoromethanesulfonate, 22

2,7-Naphthalenediol (15.0 g, 93.6 mmol) was dissolved in anhydrous pyridine (225 mL) under an argon atmosphere, the solution was cooled to −20° C., and trifluoromethanesulfonic anhydride (17.3 mL, 103 mmol) was slowly added via syringe. The reaction mixture was stirred at −20° C. for 8 hours, poured into water (225 mL), and extracted with ether (3×225 mL). The organic phase was separated, washed with aqueous 10% HCl (225 mL), water (225 mL), and brine (225 mL). The organic phase was separated, dried with MgSO$_4$, and the solvent was evaporated to give an oil which was purified by column chromatography using hexanes-EtOAc, 75:25, as eluent to give the title compound 22 as an oil (9.31 g, 34%). $^1$H-NMR (200 MHz, Me$_2$SO-d$_6$): d 10.13 (s, 1, OH), 7.98–7.16 (m, 6, HAr). $^{13}$C-NMR (50 MHz, CDCl$_3$): d 154.9 (C2), 147.8 (C7), 134.9 (C8$_a$), 130.5, 130.0, 127.8 (C4$_a$), 119 (q, CF$_3$, J$_{C,F}$=320 Hz), 119.3, 117.7, 117.0, 109.7. Compound 7 was also obtained as an oil (10.34 g, 26%). $^1$H-NMR (200 MHz, Me$_2$SO-d$_6$): d 8.28(m, 4, HAr), 7.70(m, 2, HAr). $^{13}$C-NMR (50 MHz, Me$_2$SO-d$_6$): 147.8 (C2, C7), 133.3 (C8$_a$), 131.3 (C1, C8), 121.2 (C3, C6), 119.8 (C4, C5), 118.3 (q, CF, J$_{C,F}$=318 Hz), 115.1 (C4$_a$). Anal. calc. for C$_{12}$H$_6$O$_6$S$_2$F$_6$: C, 33.97, H, 1.42, S, 15.11, F, 26.87. Found: C, 34.00; H, 1.36; S, 15.11; F, 26.81.

EXAMPLE 6

9-((4-(7-(2-O-trifluoromethanesulfonyl)naphthyl)-O-2-propynyloxy-)-3,5-O-tetraisopropyldisiloxanyl-β-D-ribofuranosyl))adenine, 8

Compounds 4 (3.43 g, 6.27 mmol) and 7 (5.32 g, 12.5 mmol) were dissolved in anhydrous DMF (55 mL). Tetrakis (triphenylphosphine)palladium(0) (217 mg, 0.19 mmol), CuI (72 mg, 0.38 mmol), and NEt$_3$ (0.58 mL, 4.1 mmol) were added and the reaction mixture was stirred under an argon atmosphere at ambient temperature for 1 hour. Additional tetrakis(triphenylphosphine)palladium(0) (217 mg, 0.19 mmol), CuI (72 mg, 0.38 mmol), and NEt$_3$ (0.58 mL, 4.1 mmol) then were added, the reaction mixture was stirred at ambient temperature for another 2 hours, the reaction mixture was cooled to 5° C., and Et$_2$O (55 mL) and water (55 mL) were added. After stirring for 5 min the organic phase was separated, the aqueous phase was extracted with Et$_2$O (2×50 mL), the Et$_2$O extracts were combined, dried with MgSO$_4$, and the solvent was evaporated in vacuo to give an oil. The crude product was purified by column chromatography using hexanes-EtOAc, 50:50, to give the title compound 8 as a foam (4.48 g, 86%). $^1$H-NMR (200 MHz, Me$_2$SO-d$_6$): 8.23 (s, 1, H8), 8.05 (s, 1, H2), 8.16–7.44 (m, 6, HAr), 7.34 (br s, 2, NH), 6.07 (s, 1, H1'), 5.04 (m, 1, H2'), 4.81 (ABq, 2, OCH$_2$CC, J=15.9 Hz), 4.82 (m, 1, H3'), 4.04 (m, 1, H4'), 3.98 (m, 2, H5'a, H5'b), 1.02 (m, 28, TPDS). $^{13}$C-NMR (50 MHz, CDCl$_3$): 155.6, 153.0, 149.0, 147.5, 138.8, 132.8, 131.6, 131.5, 130.4, 129.7, 127.9, 127.6, 121.7, 120.3, 119.0, 118.7 (q, CF, J$_{C,F}$=320 Hz), 88.6, 86.4, 81.4, 80.1, 77.2, 69.6, 59.8, 59.1, 17.0 (CH$_3$), 12.7 (CH). $^{19}$F-NMR (188 MHz, CDCl$_3$): d 105.6. FTIR (NaCl): 2231 cm$^{-1}$ (w, CCH).

EXAMPLE 7

2-(t-Butyldimethylsilyl)-5-tri-n-butylstannyl-N,N,-dimethylimidazole-1-sulfonamide, 9

Compound 25 (20.6 g, 71.2 mmol) was dissolved in anhydrous THF (200 mL) under an argon atmosphere. The solution was cooled to −78° C., and 1.6 M nBuLi (49 mL, 78.4 mmol) was added. After stirring the reaction mixture for 25 min at −78° C., tributyltin chloride (21.26 mL, 78.4 mmol) was added via syringe and the mixture was allowed to warm to ambient temperature. After stirring at ambient temperature for 2 hours, the reaction mixture was poured into ice water (200 mL). Ether (200 mL) was added and the mixture was stirred. The organic phase was separated, dried with MgSO$_4$, and the solvent was evaporated to give an oil which was purified by column chromatography using hexanes followed by hexanes-EtOAc, 90:10, to give the title compound 9 as an oil (21.21 g, 52%). The product was protected from light and stored at 0° C. $^1$H-NMR (200 MHz, CDCl$_3$): d 7.16 (1, s, H4), 2.68 (s, 6, NCH$_3$), 1.5–0.8 (m, Bu), 0.94 (s, 9, Me$_3$), 0.40 (s, 6, SiCH$_3$).

EXAMPLE 8

9-((4-(7-(5-N,N,-dimethylimidazole-1-sulfonamide) naphthyl)-O-2-propynyloxy-)-3,5-O-tetraisopropyldisiloxanyl-β-D-ribofuranosyl)) adenine, 10

Compound 8 (1.00 g, 1.21 mmol), compound 9 (777 mg, 1.34 mmol), LiCl (149 mg, 3.51 mmol), tetrakis (triphenylphosphine)palladium(0) (140 mg, 0.12 mmol) and 2,6-di-t-butyl-4-methylphenol (few crystals) were mixed in anhydrous methoxyethylether (10 mL), and the reaction mixture was heated at 120° C. for 2 hours under an argon atmosphere. The reaction mixture was cooled to ambient temperature, Et$_2$O (10 mL) and water (10 mL) were added, and the mixture was stirred for several min. The organic phase was separated, the aqueous phase was extracted with Et$_2$O (2×10 mL), and the Et$_2$O extracts were combined and dried with MgSO$_4$. The solvent was evaporated in vacuo to give an oil which was purified by column chromatography using EtOAc to afford the title compound as a foam (473 mg, 48%). $^1$H-NMR (200 MHz, CDCl$_3$): 8.25 (s, 1, H8), 8.15 (s, 1, H2), 8.11 (s, 1, H2-Im), 7.90–7.44 (m, 8, HAr), 7.15 (s, 1, H4-Im), 6.34 (br s, 2, NH), 6.12 (s, 1, H1'), 4.88 (ABq, 2, OCH$_2$CC, J=16 Hz), 4.82 (d, 1, H2'), 4.68 (d, 1, H3', J$_{2',3'}$=4.5 Hz), 4.23 (m, 1, H4'), 4.15 (m, 2, H5'a, H5'b), 2.43 (s, 6, NCH$_3$), 1.07 (m, 28, TPDS). $^{13}$C-NMR (50 MHz, CDCl$_3$): 155.1 (C6, 152.3 (C2), 149.0 (C4), 140.3, 139.0 (C8, C2-Im), 132.5, 132.0, 131.8, 131.6, 131.4, 129.6, 129.4, 128.8, 127.7, 127.5, 126.4, 120.6, 120.2 (C5, C5-Im), 88.6 (C1'), 87.0 (CC), 85.6 (CC), 81.4 (C4'), 80.0 (C3'), 69.6 (C2'), 59.7, 59.1 (C5', OCH$_2$CC), 37.4 (NCH$_3$), 17.0 (m, CMe$_3$), 12.7 (m, SiCH$_3$). FTIR (KBr): 2230 cm$^{-1}$ (w, CC).

EXAMPLE 9

9-((4-(7-(5-N,N,-dimethylimidazole-1-sulfonamide) naphthyl)-O-2-propyloxy-)-β-D-ribofuranosyl)) adenine, 14

Method A

Compound 10 (1 mmol) is dissolved in THF (5 mL) and 1M nBu$_4$NH$_4$F (3 mL, 3 mmol) added to the reaction mixture. After stirring the reaction mixture for several hours the solvent is evaporated to an oil and the crude product purified by column chromatography to give compound 11, 9-((4-(7-(5-N,N,-dimethylimidazole-1-sulfonamide) naphthyl)-O-2-propynyloxy-)-β-D-ribofuranosyl))adenine. Palladium-on calcium carbonate catalyst (1 g) and benzene (30 mL) are placed in a reaction vessel attached to atmospheric pressure hydrogenation apparatus equipped with a side arm. The air in the system is replaced with hydrogen by evacuating the container and refilling with hydrogen three times. The catalyst suspension is stirred until no more gas is absorbed. Compound 11 (1.7 mmol) then is dissolved in benzene (30 mL) and added to the reaction vessel. The mixture is stirred under a hydrogen atmosphere as rapidly as possible until 207 mL (4.9 molar eq) of gas (22° C., 740 torr) are absorbed over about 5 min. The mixture is filtered through a scintered glass funnel, and the catalyst washed with benzene (3×20 mL). The solvent is evaporated in vacuo and the product purified by column chromatography using hexane-EtOAc as eluent to give compound 12, 9-((4-(7-(5-N,N,-dimethylimidazole-1-sulfonamide)naphthyl)-O-2-cis-propenyloxy-)-β-D-ribofuranosyl))adenine.

Compound 11 (1.06 mmol) is added to a toluene (10 mL) solution of dihydrido(bicarbonato)bis (triisopropylphosphine)rhodium (III) (0.17 g, 0.35 mmol). After the colorless solution turns orange-red and CO$_2$ has evolved, the concentrated residue of the reaction mixture is washed with hexanes-EtOAc. Evaporation of the washes gives an oil which is purified by column chromatography using hexanes-EtOAc as eluent to yield compound 13, 9-((4-(7-(5-N,N,-dimethylimidazole-1-sulfonamide) naphthyl)-O-2-trans-propenyloxy-)-β-D-ribofuranosyl)) adenine.

Compound 11 (0.47 mol), 12 (0.47 mol), or 13 (0.47 mol) are dissolved in absolute ethanol (125 mL) in a Parr bottle containing 5% palladium on carbon catalyst (0.2 g). The bottle is attached to Parr hydrogenation apparatus, and shaken at an initial pressure of 60 psi. After 2 hours hydrogen uptake ceases. The mixture is gravity-filtered twice and the solvent evaporated in vacuo to give an oil which is purified by column chromatography using hexanes-EtOAc as eluent to afford the title compound 14.

Method B

Compound 10 was hydrogenated (75 psi H$_2$) with using platinum (II) oxide as catalyst with ethanol as solvent at ambient temperature in a Parr apparatus to afford compound 10a, 9-((4-(7-(5-N,N,-dimethylimidazole-1-sulfonamide) naphthyl)-O-2-propyloxy-)-3,5-O-tetraisopropyldisiloxanyl-b-D-ribofuranosyl))adenine, in a 95% yield. $^1$H-NMR (200 MHz, CDCl$_3$): δ6.04 (s, 1H, H1'), 2.94 (m, 2H, CH$_2$-naph), 2.08 (m, 2H, CH$_2$-CH$_2$-naph).

Compound 10a was treated with tetrabutylammonium fluoride in the usual way to provide the title compound 14 in 85% yield.

EXAMPLE 10

9-((4-(7-(5-imidazoyl-1-H)naphthyl)-O-2-propyloxy-)-b-D-ribofuranosyl))adenine, 14a The imidazoyl group of compound 14 was deprotected by reaction with sodium methoxide in methanol-water to give the title compound 14a in 95% yield. $^1$H-NMR (200 MHz, Me$_2$SO-d$_6$): δ12.21 (br s, 1H, ImH), 8.42 (1H, s, HC2), 8.15 (s, 1H, HC8), 8.12 (s, 1H, H-Im), 7.9–7.0 (m, 6H, naph), 7.42 (s, 2H, NH2), 7.40 (s, 1H, Im-H), 6.06 (d, 1H, H1'), 5.45 (br s, 1, HO), 5.25 (br s, 1, HO), 3.2 (m, 2H, CH$_2$), 2.62 (m, 2H, CH$_2$), 1.79 (m, 2H, CH$_2$).

EXAMPLE 11

N6-benzoyl-9-((4-(7-(5-imidazoyl-1-H)naphthyl)-O-2-propyloxy)-b-D-ribofuranosyl))adenine, 14b Compound 14a was treated with trimethylsilyl chloride followed by reaction with benzoyl chloride to afford compound the title compound 14b in a 78% yield.

EXAMPLE 12

N6-benzoyl-9-((4-(7-(5-imidazoyl-1-(4',4"-dimethoxyltrityl))-naphthyl)-O-2-propyloxy-)5'-O-(4',4"-dimethoxyltrityl)-b-D-ribofuranosyl))adenine 3'-[b-cyanoethyl N,N-diisopropylphosphoramidite] (14d)

Compound 14b was reacted with dimethoxyltrityl chloride in the usual way to provide compound 14c, N6-benzoyl-9-((4-(7-(5-imidazoyl-1-(4',4"-dimethoxyltrityl))naphthyl)-O-2-propyloxy-)5'-O-(4',4"-dimethoxyltrityl)-b-D-ribofuranosyl))adenine, in 85% yield.

Compound 14c was treated with diisopropylamine hydrotetrazolide and bis(diisopropylamino)(b-cyanoethoxy)-phosphine to give the title compound 14d in 91% yield. $^{31}$P-NMR (80 MHz, CDCl$_3$): δ151.0 (d).

EXAMPLE 13

9-((4-(7-(2-(3-Amino-1-propynyl)naphthyl)-O-2-propynyloxy-)-3,5-O-tetraisopropyldisiloxanyl-β-D-ribofuranosyl))adenine, 15

Propargyl amine (1.92 mmol), compound 8 (1.92 mmol), tetrakis (triphenylphosphine)palladium(0) (222 mg, 0.192 mmol), CuI (73 mg, 0.384 mmol), and NEt$_3$ (0.54 mL, 3.84 mmol) are stirred in anhydrous DMF (10 mL) under an argon atmosphere at ambient temperature. After 3 hours, the solvent is evaporated in vacuo (1 torr) at 40° C. to give an oil which is dissolved in EtOAc. The organic phase is washed with water and dried with MgSO$_4$. The solvent is evaporated in vacuo to give a foam and the product is purified by column chromatography using hexane-EtOAc to give the title compound 15.

EXAMPLE 14

Bis[4-(2-(t-Butyldimethylsilyl)-5(3-(N,N-1,1,4,4-tetramethylsilethylene)aminopropyl)-N,N,-dimethylimidazole-1-sulfonamide)]glycolic acid, 16

Compound 31 (23 mmol) is dissolved in anhydrous THF (200 mL) and the reaction mixture cooled to −78° C. under an argon atmosphere. nBuLi (1M, 25 mL, 25 mmol) is added and the reaction mixture stirred for 20 min at −78° C. Ethyl N,N-dimethyl oxamate (11.5 mmol) is added and the reaction mixture allowed to slowly warm to ambient temperature. Water (100 mL) and then Et$_2$O (200 mL) are added. The organic phase is separated and evaporated in vacuo to give the product, which is purified by column chromatography to provide the title compound 16.

EXAMPLE 15

9-((4-(7-(2-(3-N-(bis-[(4-(3-aminopropyl))-5-imidazoyl glycolic acid amide)-1-propynyl)naphthyl)-O-2-propynyloxy-)-3,5-O-tetraisopropyldisiloxanyl-β-D-ribofuranosyl))adenine, 17

Compound 16 (1 mmol) is dissolved in anhydrous DMF (5 mL) and dicyclohexylcarbodiimide (1.1 mmol), and N-hydroxybenzotriazole-monohydrate (1.1 mmol) are added. The mixture is stirred under an argon atmosphere for 10 min. Compound 15 then is added, the reaction mixture stirred at ambient temperature for several hours, and water (5 mL) is added. After stirring for 5 min ether (10 mL) is added, the mixture is stirred, the organic phase separated and dried with MgSO$_4$. The solvent is evaporated to give a crude product which is purified by column chromatography using hexanes-EtOAc as eluent to afford the title compound 17.

EXAMPLE 16

9-((4-(7-(2-(3-N-(bis-[(4-(3-aminopropyl))-5-imidazoyl glycolic acid amide)-1-cis-propenyl)naphthyl)-O-2-cis-propenyloxy-)-3,5-O-tetraisopropyldisiloxanyl-β-D-ribofuranosyl))adenine, 18

Palladium-on-calcium carbonate catalyst (1 g) and benzene (30 mL) are placed in a reaction vessel attached to an atmospheric pressure hydrogenation apparatus equipped with a side arm. The air in the system is replaced with hydrogen by evacuating the container and refilling with hydrogen three times. The catalyst suspension is stirred until no more gas is absorbed. Compound 17 (1.7 mmol) is dissolved in benzene (30 mL) and the solution added to the reaction vessel. The mixture is stirred under a hydrogen atmosphere as rapidly as possible until 207 mL (4.9 molar eq) of gas (22° C., 740 torr) are absorbed over about 5 min. The mixture is filtered through a scintered glass funnel, and the catalyst washed with benzene (3×20 mL). The solvent is evaporated in vacuo and the product purified by column chromatography using hexane-EtOAc as eluent to give the title compound 18.

EXAMPLE 17

9-((4-(7-(2-(3-N-(bis-[(4-(3-aminopropyl))-5-imidazoylglycolic acid amide)-1-trans-propenyl)naphthyl)-O-2-transpropenyloxy)-3,5-O-tetraisopropyldisiloxanyl-β-D-ribofuranosyl))adenine, 19

Compound 17 (1.06 mmol) is added to a toluene (10 mL) solution of dihydrido(bicarbonato)bis(triisopropylphosphine)rhodium (III) (0.17 g, 0.35 mmol). After the colorless solution turns orange-red and CO$_2$ gas has evolved, the concentrated residue of the reaction mixture is washed with hexanes-EtOAc. Evaporation of the washes gives an oil which is purified by column chromatography using hexanes-EtOAc as eluent to yield the title compound 19.

EXAMPLE 18

9-((4-(7-(2-(3-N-(bis-[(4-(3-aminopropyl))-5-imidazoyl glycolic acid amide)-1-propyl)naphthyl)-O-2-propyloxy-)-3,5-O-tetraisopropyldisiloxanyl-β-D-ribofuranosyl))adenine, 20

Compound 17 (0.47 mol), 18 (0.47 mol), or 19 (0.47 mol) is dissolved in absolute ethanol (125 mL) in a Parr bottle containing 5% palladium on carbon catalyst (0.2 g). The bottle is attached to a Parr hydrogenation apparatus, and shaken at an initial pressure of 60 psi. After 2 hours, hydrogen uptake ceases and the mixture is gravity-filtered twice. The solvent is evaporated in vacuo to give an oil which is purified by column chromatography using hexanes-EtOAc as eluent to afford the title compound 20.

EXAMPLE 19

7-(5-(2-(t-Butyldimethylsilyl)-N,N,-dimethylimidazole-1-sulfonamide))naphthalene, 23

Compound 5 (12.65 g, 31.1 mmol), compound 9 (14.5 g, 25.2 mmol), LiCl (3.83 g, 90.2 mmol), tetrakis(triphenylphosphine)palladium(0) (3.60 g, 3.11 mmol) and 2,6-di-t-butyl-4-methylphenol (about 2 mg) were mixed in anhydrous methoxyethylether (130 mL) and the reaction mixture heated at 120° C. for 24 hours under an argon atmosphere. After cooling to ambient temperature pyridine (15 mL) was added, followed by addition of 1.4 M hydrogen fluoride-pyridine in THF (26 mL, 36.4 mmol). After stirring for 5 hours ether (500 mL) was added, the mixture was filtered through Celite and the organic phase was washed with water (500 mL), aqueous 10% HCl (500 mL), water (500 mL), and brine (500 mL). The organic phase was separated, dried with MgSO$_4$, and the solvent was evaporated to give an oil which was purified by column chromatography using hexane-EtOAc, 60:40. The title compound was obtained as an oil (4.15 g, 38%). $^1$H-NMR (200 MHz, Me$_2$SO-d$_6$): d 8.09 (s, 1, ImH2), 7.84–7.15 (m, 6, HAr), 7.12 (s, 1, ImH2), 2.42 (s, 6, NCH$_3$), 1.02 (s, 9, Me$_3$), 0.26 (SiCH$_3$). $^{13}$C-NMR (50 MHz, CDCl$_3$): d 154.2 (C2), 140.2, 134.0 (C7), 132.2 (C8$_a$), 131.1, 129.3, 129.0 (C4$_a$), 128.7, 127.7, 127.5, 125.9 (2, ImC5), 123.2, 115.1 (ImC4), 37.4 (NCH$_3$), 25.7 (Me$_3$), 18.2 (SiC), −4.3 (SiCH$_3$). Anal. Calc. for C$_{21}$H$_{29}$N$_3$O$_3$SSi: C, 58.44, H, 6.77, N, 9.74, Si, 6.51, S, 7.43. Found: C, 58.22; H, 6.78; N, 9.42; S, 7.44; Si, 6.47.

EXAMPLE 20

2-Hydroxy-7-(5-N,N,-dimethylimidazole-1-sulfonamide)naphthalene, 24

Compound 23 (4.15 g, 9.61 mmol) was deprotected employing methodology similar to that used for the synthesis of compound 2. A crude oil was obtained which was purified by column chromatography using EtOAc followed by EtOAc-MeOH, 80:20, to afford the title compound 24 as an oil (2.32 g, 76%). $^1$H-NMR (200 MHz, Me$_2$SO-d$_6$): d 9.83 (s, 1, OH), 8.21 (s, 1, ImH2), 7.84–7.11 (m, 6, HAr), 7.15 (s, 1, ImH4), 2.49 (s, 6, NCH$_3$). $^{13}$C-NMR (50 MHz, CDCl$_3$): d 154.2 (C7), 138.2 (ImC2), 132.5 (C2), 130.7 (C8a), 129.3, 127.6, 126.6, 126.2 (C4a), 125.8, 124.2 (ImC5), 123.2, 118.3, 107.7, 35.8 (NCH$_3$). Anal. calc. for C$_{15}$H$_{15}$N$_3$O$_3$S: C, 56.77, H, 4.76, N, 13.24. Found: C, 56.38; H, 4.88; N, 12.77.

EXAMPLE 21

Bis[5-(2-(t-butyldimethylsilyl)-N,N,-dimethylimidazole-1-sulfonamide)]carbinol, 26

Compound 25 (14.81 g, 51.2 mmol) was dissolved in anhydrous THF (530 mL) under an argon atmosphere, the solution was cooled to −78° C. and 1.6 M nBuLi (38.4 mL, 61.4 mmol) was added slowly via syringe. After stirring the reaction mixture at −78° C. for 25 min, ethylformate (2.07 mL, 25.6 mmol) was added, and the mixture was allowed to warm to ambient temperature. After stirring for 1 hour, glacial AcOH was added to pH 5, and the mixture was poured into aqueous saturated $NaHCO_3$ (530 mL). The organic phase was separated and the aqueous phase extracted with ether (3×530 mL). The extracts were combined and dried with $MgSO_4$ and the solvent was evaporated in vacuo to give an oil which was purified by column chromatography using $CH_2Cl_2$-acetone, 90:10, to afford the title compound 26 as a solid (10.65 g, 69%). $^1$H-NMR (200 MHz, $CDCl_3$): d 7.04 (s, 2, H4), 6.51 (d, 1, CH, $J_{H,OH}$=3.3 Hz), 3.79 (d, 1, OH), 2.78 (s, 12, $NCH_3$), 0.98 (s, 18, $Me_3$), 0.39 (s, 12, $CH_3$). $^{13}$C-NMR (50 MHz, $CDCl_3$): d 156.9 (C2), 134.8 (C5), 132.2 (C4), 59.6 (COH), 37.7 ($NCH_3$), 27.2 ($Me_3$), 18.3 (SiC), −3.6 ($SiMe_2$). Anal. calc. for $C_{23}H_{46}N_6O_5S_2Si_2$: C, 45.52, H, 7.64, N, 13.85, S, 10.57, Si, 9.26. Found: C, 45.32; H, 7.69; N, 13.93; S, 10.79; Si, 9.30.

EXAMPLE 22

Bis[5-(2-(t-butyldimethylsilyl)-N,N,-dimethylimidazole-1-sulfonamide)]-O-benzyloxymethylcarbinol, 27

Compound 26 (1.214 g, 2.0 mmol) was dissolved in anhydrous DMF (12 mL), NaH (96 mg, 2.4 mmol) as a 60% dispersion in oil was added at ambient temperature and the reaction mixture was stirred for 10 min under an argon atmosphere. Benzylchloromethyl ether (0.34 mL, 2.2 mmol) then was added. After 4 hours glacial AcOH was added to reach a pH 3, MeOH (2 mL) was added, and the mixture was stirred for 5 min. The solvent was evaporated in vacuo to give an oil which was purified by column chromatography using hexanes-EtOAc, 60:40, as eluent to give the title compound 27 as an oil (1.16 g, 80%). $^1$H-NMR (200 MHz, $CDCl_3$): d 7.33–7.17 (m, 5, HAr), 7.12 (s, 2, ImH4), 6.44 (s, 1, CHO), 4.94 (s, 2, $OCH_2O$), 4.55 (s, 2, $OCH_2Ph$), 2.71 (s, 12, $NCH_3$), 0.98 (s, 18, $Me_3$), 0.40 (s, 6, $SiCH_3$), 0.38 (s, 6, $SiCH_3$).

EXAMPLE 23

2-(t-Butyldimethylsilyl)-5-aldehydo-N,N,-dimethylimidazole-1-sulfonamide, 28

Compound 25 (1.0 mmol) is dissolved in anhydrous THF (10 mL), the reaction mixture cooled to −78° C., 1M nBuLi (1.1 mL, 1.1 mmol) added, and the reaction mixture stirred at −78° C. for 30 min under an argon atmosphere. Anhydrous DMF (1.1 mmol) then is added, the reaction mixture is stirred at −78° C. for 20 min then allowed to warm to ambient temperature. Ether (10 mL) and then water (5 mL) are added. The organic phase is separated, dried with $MgSO_4$ and the solvent evaporated in vacuo to give a product which is purified by column chromatography to give the title compound 28.

EXAMPLE 24

2-(t-Butyldimethylsilyl)-5-(2-cyanoethenyl)-N,N,-dimethylimidazole-1-sulfonamide, 29

Sodium amide (2.0 g, 51.3 mmol) is added under an argon atmosphere to a solution of diethylcyanomethyl-phosphonate (8.85 g, 50 mmol) in anhydrous THF (40 mL). The suspension is stirred at ambient temperature for 1 hour.

A solution of compound 28 (25 mmol) in anhydrous THF (60 mL) is added to the resulting reaction mixture. The mixture is heated at reflux temperature for 20 hours, cooled to ambient temperature, and water (100 mL) is added. After evaporation of the THF in vacuo, $CH_2Cl_2$ (400 mL) is added to the aqueous suspension. The organic phase is separated and the aqueous phase extracted with $CH_2Cl_2$ (2×50 mL). The organic extracts are combined and washed with water (2×50 mL), dried with $MgSO_4$ and evaporated in vacuo to yield a product which is purified by column chromatography to afford the title compound 29.

EXAMPLE 25

2-(t-Butyldimethylsilyl)-5-(3-aminopropyl)-N,N,-dimethylimidazole-1-sulfonamide, 30

Compound 29 (2.1 mmol) is dissolved in absolute ethanol (75 mL) and THF (25 mL). Chloroform (1.5 mL) and platinum oxide (70 mg) are added and the mixture subjected to hydrogenation at 5 atmospheres in a Parr hydrogenation apparatus. After 4 hours the mixture is filtered through celite and the celite bed washed with absolute ethanol (2×20 mL). The filtrate and washings are evaporated in vacuo to give a product which is purified by column chromatography to provide the title compound 30.

EXAMPLE 26

2-(t-Butyldimethylsilyl)-5-(3-(N,N-1,1,4,4-tetramethylsilethylene)aminopropyl)-N,N,-dimethylimidazole-1-sulfonamide, 31

A solution of 1,1,4,4-tetramethyl-1,4-dichlorosilethylene (1.8 g, 8 mmol) in anhydrous $CH_2Cl_2$ (3 mL) is added to a stirred solution of 30 (8 mmol) in $CH_2Cl_2$ (5 mL) containing $NEt_3$ (16 mmol). The mixture is stirred under argon atmosphere at ambient temperature for 2 hours and poured into aqueous sodium dihydrogen phosphate (5 mL). $Et_2O$ (10 mL) then is added. The organic phase is separated and the solvent evaporated in vacuo to give a product which is purified by column chromatography using neutral alumina to provide the title compound 31.

EXAMPLE 27

Bis[4-(5-(3-aminopropyl)-N,N,-dimethylimidazole-1-sulfonamide)]glycolic acid dihydrochloride, 32

Compound 16 (1 g) is dissolved in 70% aqueous ethanol (20 mL) with concentrated HCl (1 mL) and the mixture evaporated in vacuo to give a product that is crystallized from methanol-chloroform to provide the title compound 32 as the dihydrochloride.

EXAMPLE 28

Bis[4-(2-(t-Butyldimethylsilyl)-5-(3-(N, N-1,1,4,4-tetramethyl-silethylene)aminopropyl)-N,N,-dimethylimidazole-1-sulfonamide) ]carbinol, 33

Compound 31 (23 mmol) is dissolved in anhydrous THF (200 mL), the reaction mixture cooled to −78° C. under an argon atmosphere, and 1M nBuLi (25 mL, 25 mmol) added. After the reaction mixture is stirred for 20 min at −78° C., ethyl formate (11.5 mmol) is added and the reaction mixture allowed to slowly warm to ambient temperature. Water (100 mL) and then $Et_2O$ (200 mL) are added. The organic phase is separated and evaporated in vacuo to give a product which is purified by column chromatography to provide the title compound 33

EXAMPLE 29

Bis[4-(5-(3-aminopropyl)-N,N,-dimethylimidazole-1-sulfonamide)]carbinol dihydrochloride, 34

Compound 33 (1 g) is dissolved in 70% aqueous ethanol (20 mL) with concentrated HCl (1 mL) and the mixture heated at reflux temperature for 6 hours. The solvent is evaporated in vacuo to give a product which is crystallized from methanol-chloroform to provide the title compound 34 as the dihydrochloride.

EXAMPLE 30

1,5-bis-(4,4'-dimethyl-1,3-oxazoline-2-yl)-3-pentanone

The protected 4-oxopimelate 101 is prepared by the saponification (March, Adv. Org. Chem. 4th Ed., J. Wiley and Sons, N. Y., 1992, p. 378) of commercially available diethyl-4-oxopimelate (Aldrich Chemicals) to give 4-oxopimelate which is protected as the 2-alkyl-1,3-oxazoline derivative (Wehrmeister, *J. Org. Chem.* 1961, 26, 3821) to afford the title compound 101.

EXAMPLE 31

2-phenyl-1,3-dithiane

Benzaldehyde is reacted with propanedithiol with boron trifluoride as catalyst (Marshall, et al., *Tetrahedron Lett.* 1971, 871) to provide the 1,3-dithiane derivative title compound 102.

EXAMPLE 32

3-(2-phenyl-1,3-dithian-2-yl)-1,5-bis-(4,4'-dimethyl-1,3-oxazolin e-2-yl)-3-pentanol Treatment of 102 with n-butyllithium and compound 101 in an umpolung reaction (Hunig, et al., *Chem. Ber.* 1989, 122, 1329; T. A. Hase, Umpoled Synthons, J. Wiley and Sons, N. Y., 1987; Seebach, *Angew. Chem.* 1979, 18, 239) affords the title compound 103.

EXAMPLE 33

4-(2-phenyl-1,3-dithian-2-yl)-4-hydroxypimelic acid

Deprotection of the 2-alkyl-1,3-oxazoline protecting groups of 103 with HCl in ethanol (Meyers, et al. *J. Am. Chem. Soc.* 1970, 92, 6644) gives the title compound 104 as the dicarboxylic acid.

EXAMPLE 34

4-(benzoyl)-4-hydroxypimelic acid

The 1,3-dithiane group of 104 is hydrolyzed by reaction with mercury II perchlorate (Lipshutz, et al. *Tetrahedron Lett.* 1989, 30, 15) to yield the title compound 105 as the a-hydroxyketone.

EXAMPLE 35

4-(benzoyl)-4-methoxypimelic acid

The tertiary hydroxyl group of 105 is methylated by treatment with methyl iodide (Jung, et al. *Tetrahedron Lett.* 1989, 30, 641) to provide the title compound 106.

EXAMPLE 36

4-(1,3-dithian-2-yl)-1,4,7-heptanetriol

Reaction of 104 with lithium aluminum hydride (Ortiz, et al., *Tetrahedron Lett.* 1985, 2831) affords the title compound 107 as the triol.

EXAMPLE 37

4-(benzoyl)-1,4,7-heptanetriol

Hydrolysis of the dithiane group of 107 is effected by reaction with mercury II perchlorate (Lipshutz, et al., *Tetrahedron Lett.* 1989, 30, 15) to provide the title compound 108 as the a-hydroxyketone triol.

EXAMPLE 38

4-(benzoyl)-1,4,7-trimethoxyheptane

Methylation of compound 108 is effected by treatment with methyl iodide (Jung, et al., *Tetrahedron Lett.* 1989, 30, 641) to give the title compound 109 as the methyl ether derivative.

EXAMPLE 39

4-(2-phenyl-1,3-dithian-2-yl)-4-methoxymethoxypimelic acid

The tertiary hydroxyl group of 104 is protected by treatment with methoxymethyl chloride (Stork, et al., *J. Am. Chem.* 1977, 99, 1275) to afford the title compound 110.

EXAMPLE 40

4-(1,3-dithian-2-yl)-4-methoxymethoxy-1,7-heptanediol

Reaction of 110 with lithium aluminum hydride (Ortiz, et al., *Tetrahedron Lett.* 1985, 2831) effects the reduction of the carboxyl functions to provide the title compound 111 as the diol derivative.

EXAMPLE 41

4-(benzoyl)-4-methoxymethoxy-1,7-dimethoxyheptane

Treatment of 111 with methyl iodide (Jung, et al., *Tetrahedron Lett.* 1989, 30, 641) followed by reaction with mercury II perchlorate (Lipshutz, et al., *Tetrahedron Lett.* 1989, 30, 15) gives the target compound 112 as the keto derivative.

EXAMPLE 42

4-(benzoyl)-4-hydroxy-1,7-dimethoxyheptane

Deprotection of the tertiary hydroxyl function of 112 is performed by reaction with methanolic HCl (Auerbach, et al., *J. Chem. Soc., Chem. Commun.* 1974, 298) to afford the target compound 113 as the a-hydroxyketone.

EXAMPLE 43

1,8-bis-(1,3-dithian-2-yl)-anthracene

The bis-1,3-dithianyl title compound 114 is afforded by treatment of the reported anthracene-1,8-dicarboxaldehyde (Guilard, et al., *J. Am. Chem. Soc.* 1992, 114, 9877) with propane dithiol and boron trifluoride as catalyst (Marshall, et al., *Tetrahedron Lett.* 1971, 12, 871).

EXAMPLE 44

1,8-bis-(3-(1,5-bis-(4,4'-dimethyl-1,3-oxazoline-2-yl)-3-pentanol)-1,3-dithian-2,2'-yl)-anthracene Treatment of 114 with n-butyllithium and 101 effects an umpolung reaction to provide the target compound 115.

EXAMPLE 45

1,8-bis-(4-(4-hydroxypimelate)-1,3-dithian-2,2'-yl)-anthracene

Deprotection of the 2-alkyl-1,3-oxazoline protecting groups of 115 with HCl in ethanol (Meyers, et al., *J. Am. Chem. Soc.* 1970, 92, 6644) gives the title compound 116 as the dicarboxylic acid.

EXAMPLE 46

1,8-bis-(4-hydroxy-4-(3-propionate)-5-oxopentanoate-5-yl)anthracene

Removal of the 1,3-dithianyl groups of 116 is effected by reaction with mercury II perchlorate (Lipshutz, et al., *Tetrahedron Lett.* 1989, 30, 15) to yield the title compound 117 as the a-hydroxyketone.

EXAMPLE 47

1,8-bis-(4-methoxy-4-(3-propionate)-5-oxopentanoate-5-yl)-anthracene

The tertiary hydroxyl group of 117 is methylated by treatment with methyl iodide (Jung, et al., *Tetrahedron Lett.* 1989, 30, 641) to provide the title compound 118.

EXAMPLE 48

1,8-bis-(4-(1,4,7-heptanetriol)-1,3-dithian-2,2'-yl)-anthracene

Reaction of 116 with lithium aluminum hydride (Ortiz, et al., *Tetrahedron Lett.* 1985, 2831) effects the reduction of the carboxyl functions to provide the title compound 119 as the polyhydroxyl derivative.

EXAMPLE 49

1,8-bis-(4-hydroxy-4-(3-hydroxypropyl)-5-hydroxy-1-pentanal-1-yl) anthracene Removal of the 1,3-dithianyl groups of 119 is effected by reaction with mercury II perchlorate (Lipshutz, et al., *Tetrahedron Lett.* 1989, 30, 15) to yield the title compound 120 as the polyhydroxy-α-hydroxyketone.

EXAMPLE 50

1,8-bis-(4-methoxy-4-(3-methoxypropyl)-5-methoxy-1-pentanal-1-yl)-anthracene Methylation of compound 120 is effected by treatment with methyl iodide (Jung, et al., *Tetrahedron Lett.* 1989, 30, 641) to give the title compound 121 as the methyl ether derivative.

EXAMPLE 51

1,8-bis-(4-(4-methoxymethoxypimelate)-1,3-dithian-2,2'-yl)-anthracene

The tertiary hydroxyl group of 116 is protected by treatment with methoxymethyl chloride (Stork, et al., *J. Am. Chem.* 1977, 99, 1275) to afford the title compound 122.

EXAMPLE 52

1,8-bis-(4-methoxymethoxy-(1,7-heptanediol)-1,3-dithian-2,2'-yl)-anthracene Reaction of 122 with lithium aluminum hydride (Ortiz, et al., *Tetrahedron Lett.* 1985, 2831) effects the reduction of the carboxyl functions to provide the title compound 123 as the tetraol derivative.

EXAMPLE 53

1,8-bis-(2-methoxymethoxy-2-(3-methoxypropyl)-5-methoxypentanal-1-yl)anthracene Treatment of 123 with methyl iodide (Jung, et al., *Tetrahedron Lett.* 1989, 30, 641) followed by reaction with mercury II perchlorate (Lipshutz, et al., *Tetrahedron Lett.* 1989, 30, 15) gives the target compound 124 as the keto derivative.

EXAMPLE 54

1,8-bis(2-Hydroxy-2-(3-methoxypropyl)-5-methoxypentanal-1-yl)anthracene

Deprotection of the tertiary hydroxyl function of 124 is performed by reaction with methanolic HCl (Auerbach, et al., *J. Chem. Soc., Chem. Commun.* 1974, 298) to afford the target compound 125 as the a-hydroxyketone.

EXAMPLE 55

4(S)-hydroxytetrahydro-2(S)-benzoyloxymethylfuran

The title compound 126 is prepared by reaction of 4(R)-(hydroxyl)tetrahydro-2(S)-benzoyloxymethylfuran (Nair, et al., *J. Am. Chem. Soc.* 1992, 114, 7951) with diethyl azodicarboxylate and triphenylphosphine (Mitsunobu, Synthesis, 1981, 1) to effect an inversion of configuration at C4.

EXAMPLE 56

4(S)-4-methylphenylsulfonoxytetrahydro-2(S)-benzoyloxymethylfuran

Reaction of 126 with p-toluene sulfonyl chloride provides the title compound 127 as the 4-tosylate. (Nair, et al., *J. Am. Chem. Soc.* 1992, 114, 7951).

EXAMPLE 57

2-(2-ethyl-1,3-dioxolane)-6H-pyrido[4,3-b] carbazolium

The reported 6H-pyrido[4,3-b]carbazole (Takano, et al., *Tetrahedron Lett.* 1979, 369) is N-2 alkylated (Husson, et al., Eur. Pat. Appl. (EP 42348 AI Dec. 23, 1981) with 2-(2-bromoethyl)-1,3-dioxolane (Lancaster Synthesis) to afford the title compound 128.

EXAMPLE 58

N-6-(4(R)-tetrahydro-2(S)-benzoyloxymethylfuranyl)-2-(2-ethyl-1,3-dioxolane)-6H-pyrido[4,3-b]carbazolium Reaction of 128 with 127 in the presence of potassium carbonate and 18-crown-6 ether (Nair, et al., *J. Am. Chem. Soc.* 1992, 114, 7951) effects a stereoselective glycosylation to afford the title compound 129.

EXAMPLE 59

N-6-(4(R)-tetrahydro-2(S)-hydroxylmethylfuranyl)-2-(2-ethyl-1,3-dioxolane)-6H-pyrido[4,3-b] carbazolium Deprotection of the O-benzoyl function is effected by treatment with ammonia (Nair, et al., *J. Am. Chem . Soc.* 1992, 114, 7951) to provide the title compound 130.

EXAMPLE 60

N-6-(4(R)-tetrahydro-2(S)-4-methylphenylsulfonoxymethylfuranyl)-2-(2-ethyl-1,3-dioxolane)-6H-pyrido[4,3-b]carbazolium The hydroxyl group of 130 is tosylated by reaction with p-toluenesulfonyl chloride (Nair, et al., *J. Am. Chem. Soc.* 1992, 114, 7951) to give the title compound 131.

EXAMPLE 61

N-6-(4(R)-tetrahydro-2(S)-O-(1,8-bis(2-hydroxy-2-(3-methoxypropyl)-5-methoxypentanal-1-yl)anthracene)-2-(2-ethyl-1,3-dioxolane)-6H -pyrido[4,3-b]carbazolium Treatment of 125 (or in a like manner compounds 113 or 117) with methyl copper I (Whitesides, et al., *J. Am. Chem. Soc.* 1974, 96, 2829) provides the copper alkoxide of 125 (or 117) which is reacted with 131 to afford the title compound 132.

EXAMPLE 62

N-6-(4(R)-tetrahydro-2(S)-O-(1,8-bis(2-hydroxy-2-(3-hydroxypropyl)-5-hydroxypentanal-1-yl)anthracene)-2-(3-propanal)-6H-pyrido[4,3-b]carbazolium Deprotection of the methylether functions of 132 with concomitant deprotection of the acetal group is effected by reaction with boron tribromide (Grieco, et al., *J. Am. Chem. Soc.*, 1977, 99, 5773. Demuynck, et al., *J. Org. Chem.* 1979, 44 4863.) to provide the title compound 133.

EXAMPLE 63

N-6-(4(R)-tetrahydro-2(S)-O-(1,8-bis(2-hydroxy-2-(3-hydroxypropyl)-5-hydroxypentanal-1-yl)anthracene)-2-(3-"substituted" propyl)-6H-pyrido[4,3-b]carbazolium (wherein the "substituent moiety" on the propyl carbazolium propyl moiety is a methyleneiminooxymethylene backbone within an oligonucleoside)

Reductive amination of 133 is effected by reaction with the hydroxyl amine function which is incorporated in an oligonucleotide backbone (Vasseur, et al., *J. Am. Chem. Soc.* 1992 114, 4006) in the presence of sodium cyano borohydride to give the title compound 134.

EXAMPLE 64

N-6-(4(R)-tetrahydro-2(S)-O-(1,8-bis(2-hydroxy-2-(3-propionate)-5-hydroxypentanal-1-yl)anthracene)-2-(3-"substituted" propyl)-6H-pyrido[4,3-b]carbazolium (wherein the "substituent moiety" on the propyl carbazolium propyl moiety is a methyleneiminooxymethylene backbone within an oligonucleoside)

In a like manner to Examples 54, 55 and 56, compound 117 is substituted for compound 125 of Example 32 to give the title compound.

EXAMPLE 65

N-6-(4(R)-tetrahydro-2(S)-O-(1,8-bis(2-hydroxy-2-(3-methoxypropyl)-5-hydroxypentanal-1-yl)anthracene)-2-(3-propanal)-6H-pyrido[4,3-b]carbazolium Deprotection of the acetal group of 132 is effected without concurrent deprotection of methylether functions of 132 by reaction with pyridinium p-toluene sulfonate as per the procedure of Hagiwara, et. al., *J. Chem. Soc., Chem. Commun.* 1987, 1351 to provide the title compound.

EXAMPLE 66

N-6-(4(R)-tetrahydro-2(S)-O-(1,8-bis(2-hydroxy-2-(3-methoxypropyl)-5-hydroxypentanal-1-yl)anthracene)-2-(3-"substituted" propyl)-6H-pyrido[4,3-b]carbazolium (wherein the "substituent moiety" on the propyl carbazolium propyl moiety is a methyleneiminooxymethylene backbone within an oligonucleoside)

In a like manner to Example 34, compound 136 is substituted for compound 133 of the example to provide the title compound.

EXAMPLE 67

Blocked Base, 5'-O-DMT Blocked, 3'-Phosphoramidite Nucleosides

Appropriately blocked phosphoramidites are prepared utilizing standard reaction for blocking the bases, the 5'-hydroxyl group and adding the 3'-phosphoramidite. Standard blockers are utilized for the bases and the standard DMT (dimethoxytrityl) group utilized for 5' hydroxyl blocking. The procedures are described in various places in the literature as for instance in Gait, M. J. (ed.) *Oligonucleotide Synthesis: A Practical Approach* 1984, IRL Press Ltd., Oxford, UK; and Eckstein, F. (ed.) *Oligonucleotides and Analogues, A Practical Approach*, IRL Press Ltd. by Oxford University Press, New York, 1991.

EXAMPLE 68

Antisense Oligonucleotides

Antisense oligonucleotides according to the present invention possessing intercalating RNA cleavers are prepared by inserting, via standard phosphoamidite coupling chemistry (Gait, M. J. (ed.) *Oligonucleotide Synthesis: A Practical Approach* 1984, IRL Press Ltd., Oxford, UK), one or more nucleosides modified with an intercalator-substituted imidazole adduct into an antisense sequence. Automated nucleic acid synthesizers such as the Applied Biosystems, Inc. 380B can be used to provide the desired modified oligonucleotides, followed by purification trityl-on reverse phase HPLC.

EXAMPLE 69

Other Modifications

For compounds of the invention wherein the cleaver is attached to the 2' position of a nucleoside, the length and the nature of the coupler between the 2'-position of the sugar and the 2-position of the substituted naphthalene can be adjusted by employing a variety of available chemistries. The imidazole can be substituted at its 1-, 2-, and 4-positions to adjust the $pK_a$, hydrogen bonding, and nucleophilicity of the resultant compound. The naphthalene-imidazole adduct can be placed on any nucleic acid nucleoside. For compounds of the invention wherein the cleaver is attached to a linking group linking two nucleosides, again the length and nature of the coupler between the backbone and the intercalator can be adjusted employing a variety of available chemistries. Other intercalators might be substituted for the pyrido[4,3-b]carbazole utilized in the illustrative examples. Further other cleaver support rings other that the anthracene ring used in conjuction with a pentofuranose ring might be to support and position the metal ion coordination ligands.

EXAMPLE 70

Hybridization Analysis

A. Evaluation of the thermodynamics of hybridization of modified oligonucleotides.

The ability of the functionalized oligonucleotides of the invention to hybridize to their complementary RNA or DNA sequences is determined by thermal melting analysis. The RNA complement is synthesized from T7 RNA polymerase and a template-promoter of DNA synthesized with an Applied Biosystems, Inc. 380B nucleic acid synthesizer. The RNA species is purified by ion exchange using FPLC (LKB Pharmacia, Inc.) or by denaturing urea-PAGE. Natural antisense oligonucleotides or those containing functionalization at specific locations are added to either the RNA or DNA complement at stoichiometric concentrations to form hybrid duplexes. The absorbance (260 nm) hyperchromicity dependence on temperature upon duplex to random coil transition is monitored using a Gilford Response II spectrophotometer. These measurements are performed in a buffer of 10 mM Na-phosphate, pH 7.4, 0.1 mM EDTA, and NaCl to yield an ionic strength of either 0.1 M or 1.0 M. Data are analyzed by a graphic representation of $1/T_m$ vs ln[Ct], where [Ct] is the total oligonucleotide concentration. From this analysis the thermodynamic parameters are determined. Based upon the information gained concerning the stability of the duplex or hetero-duplex formed, the placement of modified pyrimidine into oligonucleotides is assessed for its effects on helix stability. Modifications that drastically alter the stability of the hybrid exhibit reductions or enhancements in the free energy (delta G) and decisions concerning their usefulness in antisense oligonucleotides are made.

B. Fidelity of hybridization of modified oligonucleotides.

The ability of the modified antisense oligonucleotides of the invention to hybridize with absolute specificity to the targeted mRNA is shown either by thermodynamic analysis (as above) with target sequences of varying sequence or by Northern blot analysis of purified target mRNA in the presence of total cellular RNA. Target mRNA is synthesized from a vector containing the cDNA for the target mRNA located downstream from a T7 RNA polymerase promoter. Synthesized mRNA is electrophoresed in an agarose gel and transferred to a suitable support membrane (i.e. nitrocellulose). The support membrane is blocked and probed using [$^{32}$P]-labeled antisense oligonucleotides. The stringency is determined by replicate blots and washing in either elevated temperatures or decreased ionic strength of the wash buffer. Autoradiography is performed to assess the presence of heteroduplex formation and the autoradiogram quantitated by laser densitometry (LKB Pharmacia, Inc.) or phosphorimaging (Molecular Dynamics, Inc.). Stringency is predetermined for the unmodified antisense oligonucleotides and the conditions used such that only the specifically targeted mRNA is capable of forming a heteroduplex with the 2'-modified oligonucleotide.

EXAMPLE 71

Nuclease Resistance

A. Evaluation of the resistance of modified oligonucleotides to serum and cytoplasmic nucleases.

Natural, phosphorothioate and modified oligonucleotides of the invention are assessed for their resistance to serum nucleases by incubation of the oligonucleotides in media containing various concentrations of fetal calf serum or adult human serum. Labeled oligonucleotides are incubated for various times, treated with protease K and then analyzed by gel electrophoresis on 20% polyacrylamide-urea denaturing gels and subsequent autoradiography or phosphor-imaging. Autoradiograms are quantitated by laser densitometry. Based upon the location of the modifications and the known length of the oligonucleotide it is possible to determine the effect of the particular modification on nuclease degradation. For the cytoplasmic nucleases, a HL60 cell line is used. A post-mitochondrial supernatant is prepared by differential centrifugation and the labeled oligonucleotides are incubated in this supernatant for various times. Following the incubation, oligonucleotides are assessed for degradation as outlined above for serum nucleolytic degradation. Autoradiography results are quantitated for comparison of the unmodified—i.e., phosphorothioate—and the modified oligonucleotides.

B. Evaluation of the resistance of modified oligonucleotides to specific endo- and exo-nucleases.

Evaluation of the resistance of natural and 2'-modified oligonucleotides to specific nucleases (i.e., endonucleases, 3',5'-exo-, and 5',3'-exonucleases) is performed to determine the exact effect of the modifications on degradation. Modified oligonucleotides are incubated in defined reaction buffers specific for various selected nucleases. Following treatment of the products with proteinase K, urea is added and analysis on 20% polyacrylamide gels containing urea is done. Gel products are visualized by staining using Stains All (Sigma Chemical Co.). Laser densitometry is used to quantitate the extent of degradation. The effects of the modifications are determined for specific nucleases and compared with the results obtained from the serum and cytoplasmic systems.

EXAMPLE 72

Screening Of Catalytic, RNA Hydrolytic Cleavage Moieties In A Bimolecular Reaction With HIV-1 TAR RNA Full length (59 mer) wt HIV-1 TAR (transactivation response) RNA is utilized. The TAR structure is prepared from an in vitro RNA T7 polymerase transcription off of a PCR-amplified ds DNA template containing the 17-bp T7 primer site and the 59-bp TAR coding sequence. CIP (calf intestinal phosphatase) is used to 5'-dephosphorylate. This is followed by 5'-kinase end labeling with 7000 Ci/mmol [$\gamma^{32}$P]dATP]. The bimolecular screening reaction mixture variables are: [$5'^{32}$p] TAR: 100 pM; Buffer species: typically sodium or potassium phosphate or MOPS; [Buffer]: 10–100 mM (higher if needed to maintain buffering capacity); EDTA: ±@ 0.1 mM; NaCl: ±about 100 mM; [Cleaver candidate]: 10 μM–50 mM; Exogenous imidazole: ±up to 1.0 mM; MgCl$_2$: ±@ 2×[Cleaver] or up to 50 mM; ZnCl$_2$: ±about 2×[Cleaver] or up to 50 mM; pH: 6.0, 7.0 and 8.0; Volume: 10–50 μL; Temperature 37° C.; Time 0–≧48 hours. Analysis is conducted via a denaturing sequencing PAGE analysis. At the appropriate time, an equal volume of 10 M urea is added to the reaction mixture. The reaction mixture is mixed and stored at −20° C. until all time points are collected. The samples are heated to 90° C. for 30 seconds and loaded on a pre-run, pre-heated (50–55° C.) sequencing gel with reference samples. The reference samples are authentic, untreated TAR RNA, limited base (HO$^-$) treatment laddered TAR, enzyme (i.e. RNase T1) limit digest of TAR and mixture of BB (bromophenol blue) and XC (xylene cyanol) tracking dyes. Urea PA sequencing gel is 12% (20:1 Acryl:Bis) & 50% urea. Electrophoresis is conducted at 70–75 W (about 1750–1950 V, depending on characteristics of gel rig) about 50–55° C. for about 2 hours until the BB and XC tracking dyes are separated from each other by 14 cm. The gels are developed by autoradiography and/or, for better quantitation, by phosphorimager. The sequence position is identified by counting base laddered TAR from the 3'- and/or 5'-ends and by confirmation via the enzyme digest pattern (i.e. T1 preference for single strand G's of the 6 base loop).

EXAMPLE 73

Screening Of Catalytic Antisense Oligonucleotides

An oligonucleotide is purified by HPLC or PAGE to yield a single chromatographic peaks or bands. About 0.1 to 0.2 $A_{260}$ absorbance units of RNA target strand (strands) and cleaver-conjugated complementary antisense DNA strand are utilized. The target and antisense strands are taken up in a 1:1 stoichiometry in component mixes A-C in 0.6 mL sterile, RNase free, silanized, snap cap tubes to a 10.0 μl final total volume.

|  | A | B | C |
|---|---|---|---|
| NaPi | 10 mM | 10 mM | — |
| Tris-HCl | — | — | 10 mM |
| EDTA | 0.1 mM | 0.1 mM | — |
| NaCl | 100 mM | 100 mM | 100 mM |
| Imidazole | — | 1.0 M | 1.0 M |
| $MgCl_2$; $ZnCl_2$; etc. | — | — | 50 mM |

Three sets of these reactions mixtures are utilized. Set 1 has a pH of 6.0, set 2 has a pH of 7.0, and set 3 has a pH of 8.0. Time points are taken for the 18 resulting test mixtures, i.e. 3 reaction mixture variants×3 pH variant mixtures×2 mixtures (experimental & control). Time points are samples from time 0 to 2 weeks. At each point, the experimental [DNA(+)·RNA] heteroduplex is compared to a control [DNA(−)·NA] heteroduplex. Temperature is maintained at 37° C. in an incubator during the course of the measurements. The results are analyzed by PAGE utilizing a standard vertical gel rig with approximately 19×19 cm plates (silanized or "Pledged") with 1.5 mm spacers and 20 well comb. Gel is 20% (20:1 Acryl:Bis) urea PAG (about 60 ml). The samples are prepared by addition of equal volumes (10 μl) of 10% glycerol. The samples are not denatured. The gels are pre-run, pre-heated to ≧55° C. and loaded while hot. All mixes are loaded for a single time point on a single 20 lane gel. The gel is run at 350–450 V (50–60°) until the bromophenol blue dye is approximated even with the top of the bottom buffer tray. The gel is removed from the plates and stained with Stains-All (over night gives darkest staining). The gels are de-stained and laser densitized and/or photographed. The RNA migrates slower than DNA of same length. DNA stains blue and RNA stains purple. Alternatively, the targeted RNA strand may be 5'-end labeled with [$^{32}$P], with subsequent cleavage analysis by autoradiography or phosphorimaging as in Example 72.

What is claimed is:

1. A method for modulating the activity of RNA, comprising contacting said RNA with a composition comprising:
   a targeting portion specifically hybridizable with a preselected nucleotide sequence of the RNA; and
   a portion which is capable of cleaving a phosphodiester bond in said RNA and which comprises a compound of the structure:

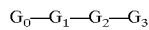

wherein:

$G_0$ is a nucleoside, a nucleotide or an oligonucleotide;

$G_1$ is a bivalent linking moiety;

$G_2$ is an aryl or heteroaryl moiety; and $G_3$ is an RNA cleaving moiety having at least general acid/base properties.

2. A method for modulating the activity of RNA, comprising contacting said RNA with a composition comprising:
   a targeting portion specifically hybridizable with a preselected nucleotide sequence of the RNA; and
   a portion which is capable of intercalating with and cleaving said RNA and which comprises a compound of the structure:

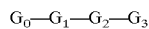

wherein:

$G_0$ is a nucleoside, a nucleotide or an oligonucleotide;

$G_1$ is a bivalent linking moiety;

$G_2$ is an aryl or heteroaryl moiety; and $G_3$ is an RNA cleaving moiety having at least general acid/base properties.

3. A method for modulating the activity of RNA, comprising contacting said RNA with with a composition comprising:
   a targeting portion specifically hybridizable with a preselected nucleotide sequence of the RNA; and
   a ribofuranosyl nucleotide which bears at its 2' site a reactive portion capable of intercalating and cleaving RNA.

4. The method of claim 1, wherein said —$G_2$—$G_3$ has one of the structures:

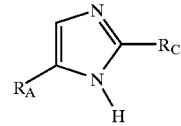

(2a)

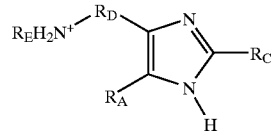

(2b)

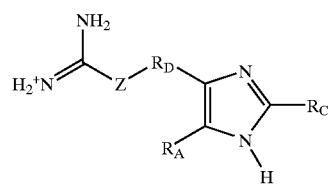

(2c)

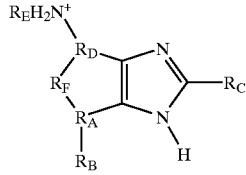

(3a)

-continued

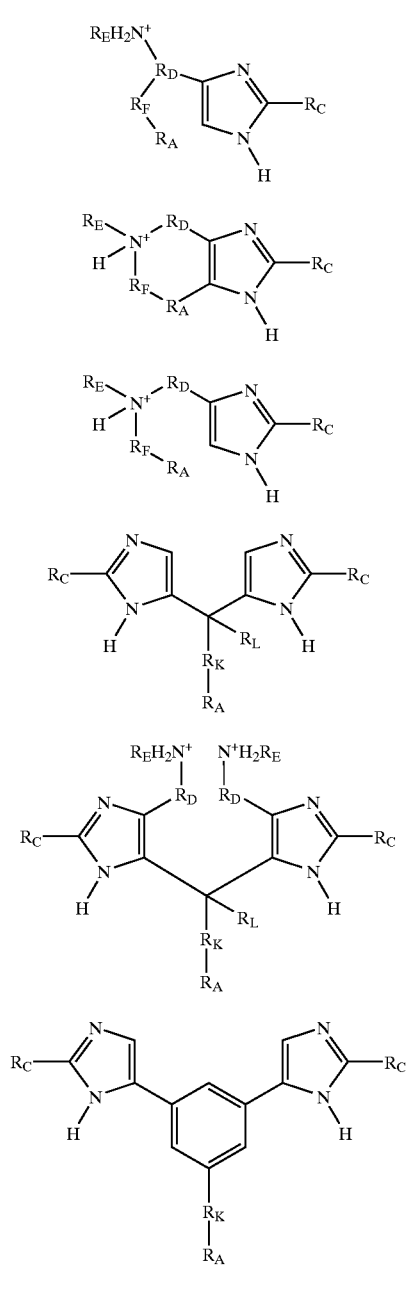

wherein:
- $R_A$ is aryl, substituted aryl, or nitrogen heterocyclic;
- $R_C$ is H, O⁻, COO⁻, $OR_G$, $NH_2$, $C(R_G)(R_H)(R_I)$, $N(R_G)(R_H)(R_I)$, Cl, Br, F, $CF_3$, $SR_G$, $NHC(O)R_G$, $OC(O)R_G$, NO, nitrogen heterocyclic or another electron donating group;
- $R_D$ is $(CH_2)_q$;
- $R_E$ is H, $(CH_2)_n$—$R_J$, or a chemical functional group comprising $R_J$;
- $R_F$ is $C_1$–$C_{20}$ alkyl, $C_2$–$C_{20}$ alkenyl or $C_2$–$C_{20}$ alkynyl, aryl, or cycloalkyl;
- $R_G$, $R_H$, and $R_I$ are, independently, H, $C_1$–$C_{10}$ alkyl, or substituted alkyl;
- $R_J$ is H, nitrogen heterocyclic, a positively charged group, or a phosphoryl hydrogen bond donating group;
- $R_K$ is alkyl, acyl or acyl-alkyl;

Z is $NH_2$ or $CH_2$;
$R_L$ is H or OH;
n is from about 1 to about 5; and
q is from about 0 to about 5.

5. The method of claim 2 wherein said —$G_2$—$G_3$ has one of the structures:

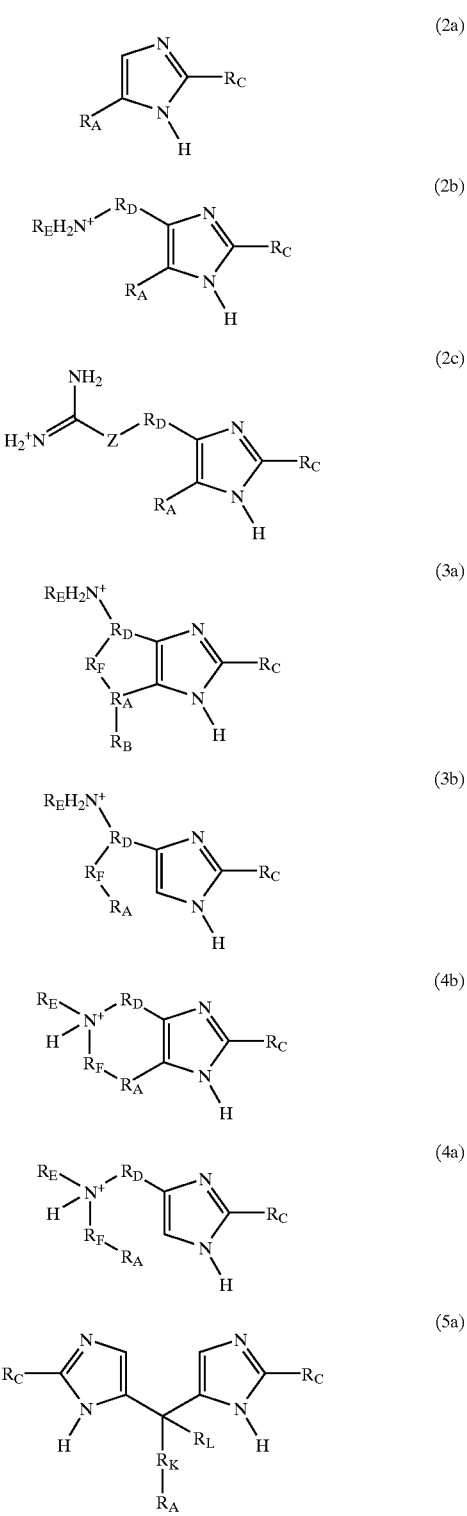

-continued

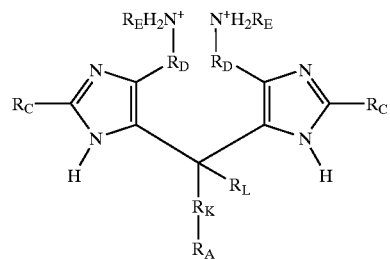
(5b)

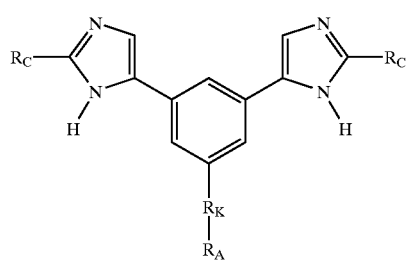
(5c)

wherein:

$R_A$ is aryl, substituted aryl, or nitrogen heterocyclic;

$R_C$ is H, O⁻, COO⁻, $OR_G$, $NH_2$, $C(R_G)(R_H)(R_I)$, $N(R_G)(R_H)(R_I)$, Cl, Br, F, $CF_3$, $SR_G$, $NHC(O)R_G$, $OC(O)R_G$, NO, nitrogen heterocyclic or another electron donating group;

$R_D$ is $(CH_2)q$;

$R_E$ is H, $(CH_2)_n$—$R_J$, or a chemical functional group comprising $R_J$;

$R_F$ is $C_1$–$C_{20}$ alkyl, $C_2$–$C_{20}$ alkenyl or $C_2$–$C_{20}$ alkynyl, aryl, or cycloalkyl;

$R_G$, $R_H$, and $R_I$ are, independently, H, $C_1$–$C_{10}$ alkyl, or substituted alkyl;

$R_J$ is H, nitrogen heterocyclic, a positively charged group, or a phosphoryl hydrogen bond donating group;

$R_K$ is alkyl, acyl or acyl-alkyl;

Z is $NH_2$ or $CH_2$;

$R_L$ is H or OH;

n is from about 1 to about 5; and q is from about 0 to about 5.

6. The method of claim 3 wherein said —$G_2$—$G_3$ has one of the structures:

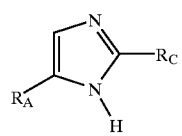
(2a)

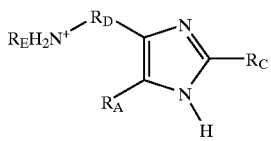
(2b)

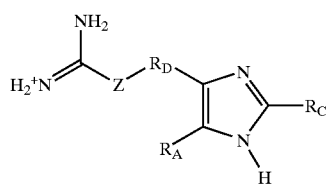
(2c)

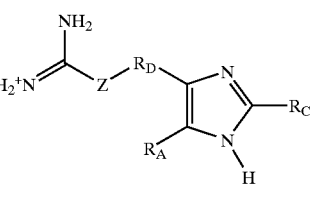
(3a)

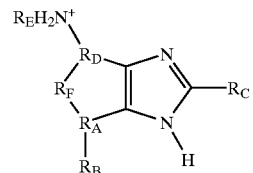
(3b)

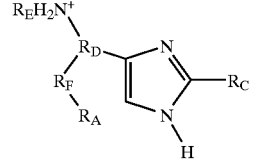
(4b)

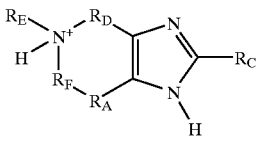
(4a)

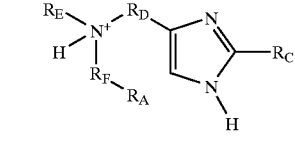
(5a)

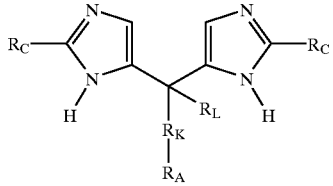
(5b)

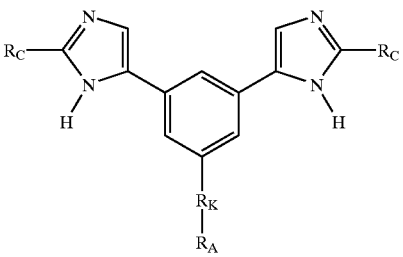
(5c)

wherein:

$R_A$ is aryl, substituted aryl, or nitrogen heterocyclic;

$R_C$ is H, O⁻, COO⁻, $OR_G$, $NH_2$, $C(R_G)(R_H)(R_I)$, $N(R_G)(R_H)(R_I)$, Cl, Br, F, $CF_3$, $SR_G$, $NHC(O)R_G$, $OC(O)R_G$, NO, nitrogen heterocyclic or another electron donating group;

$R_D$ is $(CH_2)q$;

$R_E$ is H, $(CH_2)_n$—$R_J$, or a chemical functional group comprising $R_J$;

$R_F$ is $C_1$–$C_{20}$ alkyl, $C_2$–$C_{20}$ alkenyl or $C_2$–$C_{20}$ alkynyl, aryl, or cycloalkyl;

$R_G$, $R_H$, and $R_I$ are, independently, H, $C_1$–$C_{10}$ alkyl, or substituted alkyl;

$R_J$ is H, nitrogen heterocyclic, a positively charged group, or a phosphoryl hydrogen bond donating group;

$R_K$ is alkyl, acyl or acyl-alkyl;

Z is $NH_2$ or $CH_2$;

$R_L$ is H or OH;

n is from about 1 to about 5; and q is from about 0 to about 5.

* * * * *

UNITED STATES PATENT AND TRADEMARK OFFICE
CERTIFICATE OF CORRECTION

PATENT NO. : 6,610,663 B2
DATED : August 26, 2003
INVENTOR(S) : Phillip Dan Cook et al.

It is certified that error appears in the above-identified patent and that said Letters Patent is hereby corrected as shown below:

Title page,
Item [56], References Cited, OTHER PUBLICATIONS, "Auchter" reference, please delete "pentinytriflat" and insert therefor -- pentinyltriflat --;
"Beaucage" reference, please delete "Intermeidates" and insert therefor
-- Intermediates --;
"Cazenave" reference, please delete "oligodexynucleotides" and insert therefor
-- oligodeoxynucleotides --;
"Constant" reference, please delete "Acids" and insert therefor -- Acid --;
"Dreyer" reference, please delete "Seqeunce-specific" and insert therefor -- Sequence-specific --;
"Hagiwara" reference, please delete "Am" and insert therefor -- A --;
"Kitajima" reference, please insert -- by -- between "mice" and "antisense";
"Kunitake" reference, please delete "p-Nitropheny" and insert therefor
-- p-Nitrophenyl --;

Signed and Sealed this

Twenty-fifth Day of January, 2005

JON W. DUDAS
*Director of the United States Patent and Trademark Office*